(12) United States Patent
Ratcliffe et al.

(10) Patent No.: US 7,939,715 B2
(45) Date of Patent: May 10, 2011

(54) PLANTS WITH IMPROVED YIELD AND STRESS TOLERANCE

(75) Inventors: Oliver J. Ratcliffe, Oakland, CA (US); Roderick W. Kumimoto, Norman, OK (US); Cai-Zhong Jiang, Fremont, CA (US); Jeffrey M. Libby, Cupertino, CA (US); Robert Creelman, Castro Valley, CA (US); Peter P. Repetti, Emeryville, CA (US); T. Lynne Reuber, San Mateo, CA (US); Neal I. Gutterson, Oakland, CA (US); Ganesh Kumar, Chesterfield, MO (US); Balasulojini Karunanandaa, Creve Coeur, MO (US); Karen Gabbert, St. Louis, MO (US)

(73) Assignee: Mendel Biotechnology, Inc., Hayward, CA (US)

( * ) Notice: Subject to any disclaimer, the term of this patent is extended or adjusted under 35 U.S.C. 154(b) by 101 days.

(21) Appl. No.: 11/981,733

(22) Filed: Oct. 30, 2007

(65) Prior Publication Data

US 2008/0301841 A1     Dec. 4, 2008

Related U.S. Application Data

(60) Continuation-in-part of application No. 10/669,824, filed on Sep. 23, 2003, which is a continuation-in-part of application No. 09/823,676, filed on Mar. 30, 2001, now Pat. No. 6,717,034, application No. 11/981,733, which is a continuation-in-part of application No. 11/728,567, filed on Mar. 26, 2007, now Pat. No. 7,635,800, which is a division of application No. 10/225,066, filed on Aug. 9, 2002, now Pat. No. 7,238,860, which is a continuation-in-part of application No. 09/837,944, filed on Apr. 18, 2001, now abandoned, and a continuation-in-part of application No. 10/171,468, filed on Jun. 14, 2002, now abandoned, application No. 11/981,733, which is a continuation-in-part of application No. 11/375,241, filed on Mar. 13, 2006, now Pat. No. 7,598,429, which is a continuation-in-part of application No. 10/225,067, filed on Aug. 9, 2002, now Pat. No. 7,135,616, which is a continuation-in-part of application No. 09/837,944, filed on Apr. 18, 2001, now abandoned, and a continuation-in-part of application No. 10/171,468, filed on Jun. 14, 2002, now abandoned, application No. 11/981,733, which is a continuation-in-part of application No. 10/374,780, filed on Feb. 25, 2003, now Pat. No. 7,511,190, which is a continuation-in-part of application No. 10/225,066, filed on Aug. 9, 2002, now Pat. No. 7,238,860, and a continuation-in-part of application No. 10/225,067, filed on Aug. 9, 2002, now Pat. No. 7,135,616, application No. 11/981,733, which is a continuation-in-part of application No. 10/546,266, filed as application No. PCT/US2004/005654 on Feb. 25, 2004, now Pat. No. 7,659,446, which is a continuation-in-part of application No. 10/374,780, filed on Feb. 25, 2003, now Pat. No. 7,511,190, application No. 11/981,733, which is a continuation-in-part of application No. 11/642,814, filed on Dec. 20, 2006, now Pat. No. 7,825,296, which is a division of application No. 10/666,642, filed on Sep. 18, 2003, now Pat. No. 7,196,245, application No. 11/981,733, which is a continuation-in-part of application No. 10/714,887, filed on Nov. 13, 2003, which is a continuation-in-part of application No. 10/666,642, filed on Sep. 18, 2003, now Pat. No. 7,196,245, application No. 11/981,733, which is a continuation-in-part of application No. 11/435,388, filed on May 15, 2006, now Pat. No. 7,663,025, which is a continuation-in-part of application No. PCT/US2004/037584, filed on Nov. 12, 2004, which is a continuation-in-part of application No. 10/714,887, filed on Nov. 13, 2003, application No. 11/981,733, which is a continuation-in-part of application No. 10/870,198, filed on Jun. 16, 2004, now Pat. No. 7,897,843, which is a continuation-in-part of application No. 10/669,824, filed on Sep. 23, 2003, which is a continuation-in-part of application No. 09/823,676, filed on Mar. 30, 2001, now Pat. No. 6,717,034, application No. 11/981,733, which is a continuation-in-part of application No. 11/705,903, filed on Feb. 12, 2007, now Pat. No. 7,868,229, which is a continuation-in-part of application No. PCT/US2006/034615, filed on Aug. 31, 2006.

(60) Provisional application No. 60/961,403, filed on Jul. 20, 2007, provisional application No. 60/310,847, filed on Aug. 9, 2001, provisional application No. 60/336,049, filed on Nov. 19, 2001, provisional application No. 60/338,692, filed on Dec. 11, 2001, provisional application No. 60/713,952, filed on Aug. 31, 2005, provisional application No. 60/434,166, filed on Feb. 17, 2002, provisional application No. 60/542,928, filed on Feb. 5, 2004, provisional application No. 60/565,948, filed on Apr. 26, 2004, provisional application No. 60/713,952, filed on Aug. 31, 2005.

(51) Int. Cl.
*C12N 15/82* (2006.01)
*A01H 5/00* (2006.01)
(52) U.S. Cl. ......... 800/290; 800/298; 800/281; 435/419
(58) Field of Classification Search ........................ None
See application file for complete search history.

(56) References Cited

U.S. PATENT DOCUMENTS

| | | |
|---|---|---|
| 5,659,026 A | 8/1997 | Baszczynski et al. |
| 5,831,060 A | 11/1998 | Wada et al. |
| 5,939,601 A | 8/1999 | Klessig et al. |
| 6,121,513 A | 9/2000 | Zhang et al. |
| 6,495,742 B1 | 12/2002 | Shinozaki et al. |
| 6,706,866 B1 | 3/2004 | Thomashow et al. |
| 6,717,034 B2 | 4/2004 | Jiang et al. |
| 6,835,540 B2 | 12/2004 | Broun et al. |
| 6,946,586 B1 | 9/2005 | Fromm et al. |
| 7,109,393 B2 | 9/2006 | Gutterson et al. |
| 7,135,616 B2 | 11/2006 | Heard et al. |
| 7,193,129 B2 | 3/2007 | Reuber et al. |

| | | | |
|---|---|---|---|
| 7,196,245 B2 | 3/2007 | Jiang et al. | |
| 7,223,904 B2 | 5/2007 | Heard et al. | |
| 7,238,860 B2 | 7/2007 | Ratcliffe et al. | |
| 7,345,217 B2 | 3/2008 | Zhang et al. | |
| 7,598,429 B2 | 10/2009 | Heard et al. | |
| 7,601,893 B2 | 10/2009 | Reuber et al. | |
| 7,635,800 B2 | 12/2009 | Ratcliffe et al. | |
| 2002/0023280 A1 | 2/2002 | Gorlach et al. | |
| 2002/0102695 A1 | 8/2002 | Silva et al. | |
| 2002/0142319 A1 | 10/2002 | Gorlach et al. | |
| 2003/0041356 A1 | 2/2003 | Reuber et al. | |
| 2003/0046723 A1 | 3/2003 | Heard et al. | |
| 2003/0061637 A1 | 3/2003 | Jiang et al. | |
| 2003/0093837 A1 | 5/2003 | Keddie et al. | |
| 2003/0101481 A1 | 5/2003 | Zhang et al. | |
| 2003/0121070 A1 | 6/2003 | Adam et al. | |
| 2003/0131386 A1 | 7/2003 | Samaha et al. | |
| 2003/0188330 A1 | 10/2003 | Heard et al. | |
| 2004/0006797 A1 | 1/2004 | Shi et al. | |
| 2004/0010821 A1 | 1/2004 | McCourt et al. | |
| 2004/0019927 A1 | 1/2004 | Sherman et al. | |
| 2004/0031072 A1 | 2/2004 | La Rosa et al. | |
| 2004/0098764 A1 | 5/2004 | Heard et al. | |
| 2004/0128712 A1 | 7/2004 | Jiang et al. | |
| 2005/0086718 A1 | 4/2005 | Heard et al. | |
| 2005/0097638 A1 | 5/2005 | Jiang et al. | |
| 2005/0155117 A1 | 7/2005 | Century et al. | |
| 2005/0172364 A1 | 8/2005 | Heard et al. | |
| 2006/0008874 A1 | 1/2006 | Creelman et al. | |
| 2006/0015972 A1 | 1/2006 | Heard et al. | |
| 2006/0162018 A1 | 7/2006 | Gutterson et al. | |
| 2006/0242738 A1 | 10/2006 | Sherman et al. | |
| 2006/0272060 A1 | 11/2006 | Heard et al. | |
| 2007/0022495 A1 | 1/2007 | Reuber et al. | |
| 2007/0101454 A1 | 5/2007 | Jiang et al. | |
| 2007/0199107 A1 | 8/2007 | Ratcliffe et al. | |
| 2007/0226839 A1 | 9/2007 | Gutterson et al. | |
| 2008/0010703 A1 | 1/2008 | Creelman et al. | |
| 2008/0155706 A1 | 6/2008 | Riechmann et al. | |
| 2008/0163397 A1 | 7/2008 | Ratcliffe et al. | |
| 2008/0229448 A1 | 9/2008 | Libby et al. | |
| 2008/0301836 A1 | 12/2008 | Century et al. | |
| 2008/0301839 A1* | 12/2008 | Ravanello | 800/289 |
| 2008/0301840 A1 | 12/2008 | Gutterson et al. | |
| 2008/0301841 A1 | 12/2008 | Ratcliffe et al. | |
| 2008/0313756 A1 | 12/2008 | Zhang et al. | |
| 2009/0049566 A1 | 2/2009 | Zhang et al. | |
| 2009/0138981 A1 | 5/2009 | Repetti et al. | |
| 2009/0151015 A1 | 6/2009 | Adam et al. | |
| 2009/0192305 A1 | 7/2009 | Riechmann et al. | |
| 2009/0205063 A1 | 8/2009 | Zhang et al. | |
| 2009/0265807 A1 | 10/2009 | Kumimoto et al. | |
| 2009/0265813 A1 | 10/2009 | Gutterson et al. | |
| 2009/0276912 A1 | 11/2009 | Sherman et al. | |

FOREIGN PATENT DOCUMENTS

| | | |
|---|---|---|
| CA | 2442496 | 3/2010 |
| EP | 0803572 A2 | 10/1997 |
| EP | 1033405 A2 | 9/2000 |
| EP | 1601758 | 4/2007 |
| JP | 2000041685 A2 | 2/2000 |
| WO | WO93/22342 | 11/1993 |
| WO | WO98/07842 | 2/1998 |
| WO | WO98/37184 | 8/1998 |
| WO | WO98/37755 | 9/1998 |
| WO | WO98/48007 | 10/1998 |
| WO | WO98/58069 | 12/1998 |
| WO | WO99/24573 | 5/1999 |
| WO | WO99/53016 | 10/1999 |
| WO | WO99/55840 | 11/1999 |
| WO | WO00/53724 | 9/2000 |
| WO | WO01/35727 A1 | 5/2001 |
| WO | WO01/36598 A1 | 5/2001 |
| WO | WO02/08410 | 1/2002 |
| WO | WO02/08411 | 1/2002 |
| WO | WO02/16655 | 2/2002 |
| WO | WO02/057439 | 7/2002 |
| WO | WO02/079245 | 10/2002 |
| WO | WO03/012116 | 2/2003 |
| WO | WO03/014327 | 2/2003 |
| WO | WO2004/031349 | 4/2004 |
| WO | WO2004/076638 | 9/2004 |
| WO | WO2005/030966 | 4/2005 |
| WO | WO2005/047516 | 5/2005 |
| WO | WO 2005/098015 | * 10/2005 |
| WO | WO2005/098015 | 10/2005 |

OTHER PUBLICATIONS

U.S. Appl. No. 09/532,591, filed Mar. 22, 2000, Samaha, R. et al.
U.S. Appl. No. 09/533,648, filed Mar. 22, 2000, Riechmann, Jose Luis et al.
U.S. Appl. No. 10/290,627, filed Nov. 7, 2002, Riechmann, Jose Luis et al.
U.S. Appl. No. 09/713,994, filed Nov. 16, 2000, Keddie, James et al.
U.S. Appl. No. 09/837,944, filed Apr. 18, 2001, Creelman, Robert et al.
U.S. Appl. No. 09/594,214, filed Jun. 14, 2000, Jones, J. et al.
U.S. Appl. No. 10/456,882, filed Jun. 6, 2003, Riechmann, Jose Luis et al.
U.S. Appl. No. 10/171,468, filed Jun. 14, 2002, Creelman, Robert et al.
U.S. Appl. No. 12/376,569, filed Aug. 3, 2007, Creelman, Robert et al.
U.S. Appl. No. 09/394,519, filed Sep. 13, 1999, Zhang, J. et al.
U.S. Appl. No. 12/573,311, filed Oct. 5, 2009, Heard, J. et al.
U.S. Appl. No. 12/577,662, filed Oct. 12, 2009, Reuber, T. et al.
U.S. Appl. No. 12/557,449, filed Sep. 10, 2009, Repetti, P. et al.
U.S. Appl. No. 09/627,348, filed Jul. 28, 2000, Thomashow, Michael et al.
U.S. Appl. No. 09/489,376, filed Jan. 21, 2000, Heard, J. et al.
U.S. Appl. No. 09/489,230, filed Jan. 21, 2000, Broun, P. et al.
U.S. Appl. No. 09/506,720, filed Feb. 17, 2000, Keddie, James et al.
U.S. Appl. No. 09/533,030, filed Mar. 22, 2000, Keddie, James et al.
U.S. Appl. No. 09/533,392, filed Mar. 22, 2000, Jiang, C-Z. et al.
U.S. Appl. No. 12/526,042, filed Feb. 7, 2008, Repetti, Peter R. et al.
U.S. Appl. No. 12/638,750, filed Dec. 15, 2009, Ratcliffe. O. et al.
Riechmann and Meyerowitz (Jun. 1998) The AP2/EREBP Family of Plant Transcription Factors, J. Biol. Chem. 379:633-646.
Martin and Paz-Ares (Feb. 1997) MYB transcription factors in plants, Trends in Genetics Trends Genet. 13:67-73.
Riechmann and Meyerowitz (Oct. 1997) MADS Domain Proteins in Plant Development, Biol. Chem. 378:1079-1101.
Ishiguro and Nakamura (Sep. 28, 1994).Characterization of cDNA encoding a novel DNA-binding protein, SPF1, that . . . , Mol. Gen. Genet. Mol. Gen. Genet. 244:563-571.
Zhang et al. (1992) Expression of Antisense or Sense RNA of an Ankyrin Repeat-Containing Gene..Plant Cell 4:1575-1588.
Kim et al. (Jun. 1997). Isolation of a novel class of bZIP transcription factors that interact with ABA-responsive and embryo-specific elements . . . , The Plant J. 11:1237-1251.
Klug and Schwabe (1995) FASEB J. 9:597-604.
Buerglin in: Duboule (1994) Guidebook to the Homeobox Genes, Oxford University Press, Oxford, UK pp. 27-71.
Forsburg and Guarente (Aug. 1989). Identification and characterization of HAP4: a third component of the . . . Genes Dev. 3:1166-1178.
Klein et al. (Jan. 15, 1996). A new family of DNA binding proteins includes putative transcriptional regulators of . . . , Mol. Gen. Genet. 250:7-16.
Rouse et al. (Feb. 1998). Changes in Auxin Response from Mutations in an AUX/IAA Gene, Science 279:1371-1373.
Littlewood and Evan (1994) Prot. Profile 1:635-709.
Tucker et al. (Jul. 1, 1994). Crystal structure of the adenovirus DNA binding protein reveals a hook-on model . . . , EMBO J. 13:2994-3002.
Foster et al. (Feb. 1994). Plant bZIP proteins gather at ACGT elements, FASEB J. 8:192-200.
da Costa E Silva et al. (Jul. 1993). BPF-1, a pathogen-induced DNA-binding protein involved in the plant defense response, The Plant J. 4:125-135.
Hall et al. (Jun. 1998). Golden 2: A Novel Transcriptional Regulator of Cellular Differentiation in the Maize Leaf. The Plant Cell 10:925-936.

Stemmer (1994) Nature 370:389-391.
Stemmer (1994) Proc. Natl. Acad. Sci. USA 91:10747-10751.
Moore et al. (1998) Proc. Natl. Acad. Sci. USA 95: 376-381.
Aoyama et al. (1995) Plant Cell 7:1773-1785.
Ma and Ptashne (1987) Cell 51; 113-119.
Giniger and Ptashne, (1987) Nature 330:670-672.
Odell et al. (Feb. 28, 1985). Identification of DNA sequences required for activity of the cauliflower mosaic virus 35S promoter. Nature 313:810-812.
An et al. (May 1988). Organ-Specific and Developmental Regulation of the Nopaline Synthase Promoter in Transgenic Tobacco Plants. Plant Physiol 88:547-552.
Fromm et al. (Oct. 1989). An Octopine Synthase Enhancer Element Directs Tissue-Specific Expression and Binds ASF-1, a Factor from Tobacco Nuclear Extracts. Plant Cell 1:977-984.
Bird et al. (1988).The tomato polygalacturonase gene and ripening-specific expression in transgenic plants, Plant Mol Biol 11:651-662.
Ringli and Keller (Aug. 1998). Specific interaction of the tomato bZIP transcription factor VSF-1 with a non-palindromic DNA sequence that controls vascular gene expression, Plant Mol. Biol. 37:977-988.
Kaiser et al. (May 1995). Cis-acting elements of the CHS1 gene from white mustard controlling . . . , Plant Mol. Biol. 28:231-243.
Baerson et al. (Dec. 1994). Identification of domains in an *Arabidopsis* acyl carrier protein gene . . . , Plant Mol. Biol. 26:1947-1959.
Ohl et al. (Sep. 1990). Functional Properties of a Phenylalanine Ammonia-Lyase Promoter from *Arabidopsis*, The Plant Cell 2:837-848.
Baerson et al. (May 1993). Developmental regulation of an acyl carrier protein gene promoter in vegetative and reproductive tissues, Plant Mol. Biol. 22:255-267.
Van Der Kop et al. (Mar. 1999). Selection of *Arabidopsis* mutants overexpressing genes driven by the promoter . . . , Plant Mol. Biol. 39:979-990.
Baumann et al. (Mar. 1999). The DNA Binding Site of the Dof Protein NtBBF1 Is Essential for Tissue-Specific . . . , The Plant Cell 11:323-334.
Guevara-Garcia (Nov. 1998). A 42 bp fragment of the pmas1 containing an ocs-like element confers a development, wound- and chemically . . , Plant Mol. Biol. 38:743-753.
Shi et al. (Dec. 1998). Gibberellin and abscisie acids regulate GAST1 expression at the level of transcription, Plant Mol. Biol. 38:1053-1060.
Willmott et al. (Nov. 1998). Dnase1 footprints suggest the involvement of at least three types of transcription factors in the regulation . . . , Plant Mol. Biol. 38:817-825.
Ainley et al. (Apr. 1993).Regulatable endogenous production of cytokinins up to 'toxic' levels in transgenic plants and plant tissues, The Plant Mol. Biol. 22: 13-23.
Kuhlemeier et al. (Apr. 1989). The Pea rbcS-3A Promoter Mediates Light Responsiveness but not Organ Specificity, The Plant Cell 1:471-478.
Schaffner and Sheen (Sep. 1991).Maize rbcS Promoter Depends on Sequence Elements Not Found in Dicot recS Promoters, The Plant Cell 3: 997-1012.
Siebertz et al. (Oct. 1989). cis-Analysis of the Wound-Inducible Promoter wun1 in Transgenic Tobacco Plants and Histochemical Localization of its Expression, The Plant Cell 1: 961-968.
Buchel et al. (1999) Plant Mol. Biol. 40:387-396.
Manners et al. (1998) Plant Mol. Biol. 38:1071-80.
Gatz et al. (Jun. 1997). Chemical Control of Gene Expression, Annu. Rev. Plant Physiol. Plant Mol. Biol. 48: 89-108.
Gan and Amasino (Dec. 1995) Inhibition of Leaf Senescence by Autoregulated Production of Cytokinin, Science 270: 1986-1988.
Odell et al. (Oct. 1994). Seed-Specific Gene Activation Mediated by the Cre/lox Site-Specific Recombination System, Plant Physiol. 106:447-458.
Lee, J.H. et al. (Oct. 1995) Derepression of the activity of genetically engineered heat shock factor causes constitutive synthesis of heat shock proteins . . . Plant J. 8: 603-612.

Prandl, R. et al. (May 1998). HSF3, a new heat shock factor from *Arabidopsis thaliana*, derepresses the heat shock response and confers thermotolerance . . . Molec. Gen. Genet. 258: 269-278.
Berger, F. et al. (1998) Positional information in root epidermis is defined during embyogenesis and acts in domains with strict boundaries. Current Biol. 8: 421-430.
Casimiro, I. et al. (Apr. 2003) Dissecting *Arabidopsis* lateral root development. Trends Plant Sci. 8: 165-171.
Costa, S., and Dolan., L. (Jul. 2003) Epidermal patterning genes are active during embryogenesis in *Arabidopsis*. Development 130: 2893-2901.
Lee, M., and Schiefelbein, J. (Nov. 24, 1999) WEREWOLF, a MYB-related protein in *Arabidopsis*, is a position-dependent regulator of cell patterning. Cell 99: 473-483.
Schaffer, R. et al. (1998) The late elongated hypocotyl mutation of *Arabidopsis* disrupts circadian rhythyms and the photoperiodic control of flowering. Cell 93: 1219-1229.
Schellmann, S., et al. (Oct. 1, 2002) TRIPTYCHON and CAPRICE mediate lateral inhibition during trichome and root hair patterning in *Arabidopsis*. EMBO J. 21: 5036-5046.
Schiefelbein, J. (Feb. 2003) Cell-fate specification in the epidermis: a common patterning mechanism in the root and shoot. Curr. Opin. Plant Biol. 6: 74-78.
Schnittger et al. (Jun. 1999) Generation of a spacing pattern: the role of TRIPTYCHON in trichome patterning in *Arabidopsis*. Plant Cell 11: 1105-1116.
Wada, T. (Mar. 1997) Epidermal cell differentiation in *Arabidopsis* determined by a Myb homolog, CPC. Science 277: 1113-1116.
Goff, S. (May 1992) Functional analysis of the transcriptional activator encoded by the maize B gene: evidence for a direct functional interaction between two classes of regulatory proteins. Genes Dev. 6: 864-875.
Hung C-Y., et al. (May 1998) A common position-dependent mechanism controls cell-type patterning and GLABRA2 regulation in the root and hypocotyl epidermis of *Arabidopsis*: Plant Physiol. 117: 73-84.
Wada, T. et al. (Dec. 2002) Role of a positive regulator of root hair development, CAPRICE, in *Arabidopsis* root epidermal cell differentiation. Development 129: 5409-5419.
Wang, H. et al. (2002) Regulation of the cell expansion gene RHD3 during *Arabidopsis* development. Plant Physiol. 129: 638-649.
Zhang, F. et al. (Oct. 2003) A network of redundant bHLH proteins function sin all TTG1-dependent pathways of *Arabidopsis*. Development 130: 4859-4869.
Kwong R.W. et al. (Jan. 15, 2003). LEAFY COTYLEDON1-LIKE defines a class of regulators essential for embryo development. Plant Cell (1):5-18.
Ma, et al. (1998) Seed-specific expression of the isopentenyl transferase gene (ipt) in transgenic tobacco. Aust. J. Plant Physiol. 25: 53-59.
Urao T. et al. (Nov. 1993) An *Arabidopsis* myb homolog is induced by dehydration stress and its gene product binds to the conserved MYB recognition sequence. Plant Cell 5: 1529-1539.
Allen, et al. (Sep. 15, 1998) A novel mode of DNA recognition by a beta-sheet revealed by the solution structure of the GCC-box binding domain in complex with DNA. EMBO J. 17: 5484-5496.
Avila J. et at.( Apr. 3, 1993) *Petunia hybrida* genes related to the maize regulatory C1 gene and to animal myb proto-oncogenes. Plant J. (4):553-62.
Borevitz, et al.(Dec. 2000) Activation Tagging Identifies a Conserved MYB Regulator of Phenylpropanoid Biosynthesis. Plant Cell 12:2383-2394.
Chao, et al. (Jun. 27, 1997) Activation of the Ethylene Gas Response Pathway in *Arabidopsis* by the Nuclear Protein Ethylene-Insensitive3 and related proteins. Cell 89:1133-1144.
Chen et al. (Mar. 2002) Expression profile matrix of *Arabidopsis* transcription factor genes suggests their putative functions in response to environmental stresses. Plant Cell 14: 559-574.
Di Cristina, et al. (Sep. 1996) The *Arabidopsis* Athb-10 (GLABRA2) is an HD-Zip protein required for regulation of root hair development. Plant J. 10: 393-402.

Di Laurenzio, et al. (Aug. 9, 1996) The SCARECROW gene regulates an asymmetric cell division that is essential for generating the radial organization of the *Arabidopsis* root. Cell 86:423-433.

Duckett, et al. (1994) Dye-coupling in the root epidermis of *Arabidopsis* is progressively reduced during development. Development 120, 3247-3255.

Eisen (Mar. 1998) Phylogenomics: Improving Functional Predictions for Uncharacterized Genes by Evolutionary Analysis. Genome Res. 8: 163-167.

Fu, et al. (2001) Expression of *Arabidopsis* GAI in transgenic rice represses multiple gibberellin responses. Plant Cell 13: 1791-802.

Gampala, et al. (1991) ABA INSENSITIVE-5 transactivates abscisic acid-inducible gene expression in rice protoplasts. At Am. Soc. Plant Biol. meeting, 1991, abstract 714.

Giraudat, et al. (Oct. 1992) Isolation of the *Arabidopsis* ABI3 Gene by Positional Cloning. Plant Cell 4: 1251-1261.

Hollung et al. (Jun. 1997) Developmental stress and ABA modulation of mRNA levels for bZIP transcription factors and Vp1 in barley embryos and embryo-derived suspension cultures, Plant Mol. Biol. 35: 561-571.

Hülskamp, et al. (Feb. 11, 1994) Genetic dissection of trichome cell development in *Arabidopsis*. Cell 76: 555-566.

Jin et al. (Nov. 15, 2000) Transcriptional repression by AtMYB4 controls production of UV-protecting sunscreens in *Arabidopsis*. EMBO J. 19:6150-6161.

Kasuga, M. et al. (1999) Improving plant drought, salt, and freezing tolerance by gene transfer of a single stress-inducible transcription factor. Nature Biotechnol. 17: 229-230.

Kim, et al. (1991) Regulated expression of transcription factors in transgenic rice confers stress tolerance. At the Am. Soc. Plant Physiol. meeting, 1991, abstract 394.

Kranz, et al. (Oct. 1998) Towards functional characterization of the members of the R2R3-MYB gene family from *Arabidopsis thaliana*. Plant J. 16:263-276.

Lee and Schiefelbein. (Mar. 2002) Cell pattern in the *Arabidopsis* root epidermis determined by lateral inhibition with feedback. Plant Cell 14, 611-618.

Liu, Q. et al. (Aug. 1998) Two transcription factors, DREB1 and DREB2, with an EREBP/AP2 DNA binding domain separate two cellular signal transduction pathways in drought and low-temperature . . . Plant Cell 10:1391-1406.

Mayer, et al. (Dec. 16, 1999) Sequence and analysis of chromosome 4 of the plant *Arabidopsis thaliana*. Nature 402: 769-777.

Ogas, et al. (Jul. 4, 1997) Cellular differentiation regulated by gibberellin in the *Arabidopsis thaliana* pickle mutant. Science 277: 91-94.

Ogas, et al. (Nov. 23, 1999) Pickle is a CHD3 chromatin-remodeling factor that regulates the transition from embryonic to vegetative development in *Arabidopsis*. Proc. Natl. Acad. Sci. U.S.A. 96: 13839-13844.

Oppenheimer et al. (Nov. 1, 1991) A myb gene required for leaf trichome differentiation in *Arabidopsis* is express in stipules. Cell 67: 483-493.

Payne, et al. (Nov. 2000) GL3 encodes a bHLH protein that regulates trichome development in *Arabidopsis* through interaction with GL1 and TTG1. Genetics 156: 1349-1362.

Peng et al. (Dec. 1, 1997) The *Arabidopsis* GAI gene defines a signaling pathway that negatively regulates gibberellin responses. Genes Dev. 11: 3194-3205.

Quattrocchio et al. (Feb. 1998) Analysis of bHLH and MYB domain proteins: species-specific regulatory differences are caused by divergent evolution of target anthocyanin genes. Plant J. 13: 475-489.

Riechmann et al. (Dec. 2000) *Arabidopsis* Transcription Factors: Genome-Wide Comparative Analysis Among Eukaryotes. Science 290: 2105-2110.

Suzuki et al. (Nov. 2001) Maize VP1 complements *Arabidopsis* abi3 and confers a novel ABA/auxin interaction in roots. Plant J. 28: 409-418.

Tamagnone et al. (Feb. 1998) The AmMYB308 and AmMYB330 transcription factors from antirhinum regulate phenylpropanoid and lignin biosynthesis in transgenic tobacco. Plant Cell 10: 135-154.

Tanimoto, et al. (Dec. 1995) Ethylene is a positive regulator of root hair development in *Arabidopsis thaliana*. Plant J. 8: 943-948.

Wang et al. (Apr. 1997) A Myb-related transcription factor is involved in the phytochrome regulation of an *Arabidopsis* Lhcb gene. Plant Cell 9: 491-507.

Wang et al. (Jun. 26, 1998) Constitutive Expression of the Circadian Clock Associated 1 (CCA1) Gene Disrupts Circadian Rhythms and Suppresses Its Own Expression. Cell 93: 1207-1217.

Bowie et al. (Mar. 1990). Deciphering the message in protein sequences: tolerance to amino acid substitutions. Science 247:1306-1310.

McConnell et al. (Jun. 2001). Nature 411 (6838):709-713.

Levee et al (1999, Molecular Breeding 5:429-440).

Bohmert et al. (Jan. 2, 1998), AGO1 defines a novel locus of *Arabidopsis* controlling leaf development, EMBO J. 17:170-180.

Bork, P. (2000), Powers and Pitfalls in Sequence Analysis: The 70% Hurdle. Genome Research, vol. 10, pp. 398-400.

Bowman et al. (Jun. 1999), CRABS CLAW, a gene that regulates carpel and nectary developments in *Arabidopsis*, encodes a novel protein . . . , Development 126:2387-2396.

Broun, et al. (Jan. 1998), A bifunctional oleate 12-hydroxylase: desaturase from *Lesquerella fendleri*. Plant J. 13(2):201-10.

Buttner M. and Singh K. (May 27, 1997), "*Arabidopsis thaliana* ethylene-responsive element biding protein (AtEBP), an ethylene-inducible, GCC box DNA-binding protein interacts with an ocs element binding protein," Proc. Nat'l Acad Sciences, vol. 94, No. 11, pp. 5961-5966.

Edwards et al. (1998), Multiple Genes Encoding the Conserved CCAAT—Box Transcription Factor Complex Are Expressed in *Arabidopsis*, Plant Physiol. 117, pp. 1015-1022.

Egea-Cortines and Weiss (Mar. 19, 2001), A rapid coming of age in tree biotechnology. Nat. Biotechnol. (3):215-6.

Elomaa et al. (1996), Transformation of antisense constructs of the chalcone synthase gene superfamily into *Gerbera hybrida*: differential effect on the expression of family members, Molecular Breeding 2:41-50.

Grace and Logan (Oct. 29, 2000), Energy dissipation and radical scavenging by the plant phenylpropanoid pathway, Philos Trans R Soc Lond B Biol Sci 355(1402):1499-1510.

He et al.( Jun. 9, 2000), Transformation of rice with the *Arabidopsis* floral regulator LEAFY causes early heading. Transgenic Res. (3):223-7.

Hurley, et al. (Jan. 2002), Structural genomics and signaling domains. Trends in Biochemical Sciences vol. 27 No. 1 pp. 48-53.

Jin et al., (Nov. 1999) Multifunctionality and diversity within the plant MYB-gene family. Plant Mol Biol 41(5); 577-585.

Kater, et al. (Feb. 1998). Multiple AGAMOUS Homologs from Cucumber and Petunia Differ in Their Ability to Induce Reproductive Organ Fate. Plant Cell 10:171-182.

King, et al. (Oct. 2001), Gibberellins are not required for normal stem growth in *Arabidopsis thaliana* in the absence of GAI and RGA. Genetics 159(2):767-76.

Kwak, S.H., Shen, R., and Schiefelbein, J. (Feb. 2005). Positional signaling mediated by a receptor-like kinase in *Arabidopsis*. Science 307, 1111-1113.

Kyozuka et al. (Nov. 1997), Eucalyptus has functional equivalents of the *Arabidopsis* AP1 gene. Plant Mol. Bio. 35 573-584.

Mandel et al. (Oct. 2, 1992). Manipulation of flower structure in transgenic tobacco, Cell 71-133-143.

Marchler-Bauer, et al. (Jan. 1, 2002), CDD: a database of conserved domain alignments with links to domain three-dimensional structure. Nucleic Acids Res. vol. 30, No. 1 pp. 281-283.

Mena et al. (Nov. 29, 1996), Diversification of C-function activity in maize flower development. Science. ; 274(5292):1537-40.

Schnittger et al. (Jun. 1998), Tissue layer and organ specificity of trichome formation are regulated by GLABRA1 and TRIPTYCHON in *Arabidopsis*. Development 125:2283-2289.

Shewmaker C. K. et al (Nov. 1999): "Seed-specific overexpression of phytoene synthase: increase in carotenoids and other metabolic effects," Plant Journal vol. 20, No. 4 pp. 401-412.

Smalle, Jan et al. (Mar. 17, 1998), The trihelix DNA-binding motif in higher plants is not restricted to the transcription factors GR-1 and GT-2, Proc. Nat'l. Acad. Sci., USA, vol. 95, pp. 3318-3322, 3.

Song, et al. (Apr. 30, 1998). Isolation and mapping of a family of putative zinc-finger prtein cDNAs from rice. DNA Res. 5(2):95-101.

Souer et al. (Apr. 19, 1996), The No Apical Meristem Gene of Petunia is Required for Pattern Formation in Embryos and . . . , Cell 85: 159-170.

Spelt, et al. (Sep. 2000), Anthocyanin1 of petunia encodes a basic helix-loop-helix protein that directly activates transcription of structural anthocyanin genes, Plant Cell 12(9):1619-32.

Sundberg, et al., ALBINO3, an *Arabidopsis* Nuclear Gene Essential for Chloroplast Differentiation, Encodes a Chloroplast Protein That Shows Homology to Proteins Present in Bacterial Membranes and Yeast Mitochondria. The Plant Cell (May 1997) vol. 9, 717-730.

Theologis, A., et al., Sequence and analysis of chromosome 1 of the plant *Arabidopsis thaliana*. Nature (Dec. 14, 2000) 408(6814), pp. 816-820.

Thompson, et al. (Nov. 11, 1994), CLUSTAL W:Improving the sensitivity of progressive multiple sequence alignment through sequence weighting, position-specific gap penalties and weight matrix choice. Nucleic Acids Res. 22(22):4673-80.

Amaya et al.(Aug. 1999), Expression of CENTRORADIALIS (CEN) and CEN-like genes in tobacco reveals a conserved mechanism controlling phase change in diverse species. Plant Cell. 11(8):1405-18.

Ambrose et al.(Mar. 2000), Molecular and genetic analyses of the silky1 gene reveal conservation in floral organ specification between eudicots and monocots. Mol. Cell.; 5(3):569-79.

The Cold Spring Harbor Laboratory, Washington University Genome Sequencing Center, and PE Biosystems *Arabidopsis* Sequencing Consortium (Feb. 4, 2000). The complete sequence of a heterochromatic island from a higher eukaryote. Cell 100(3), 377-386.

Chern et al.(Jul. 2001), Evidence for a disease-resistance pathway in rice similar to the NPR1-mediated signaling pathyway in *Arabidopsis*. Plant J.; 27(2):101-13.

Coupland (Oct. 12, 1995). Flower development. LEAFY blooms in aspen. Nature 377:482-483.

Daly et al. (Dec. 2001). Plant Systematics in the Age of Genomics. Plant Physiology 127:1328-1333.

Duggleby, Identification of an acetolatate synthase small subunit gene in two eukaryotes. (May 6, 1997) Gene 190:245-249.

Huang, et al., Cloning and Functional Characterization of an *Arabidopsis* Nitrate Transporter Gene That Encodes a Constitutive Component of Low-Affinity Uptake. The Plant Cell (Aug. 1999) vol. 11, 1381-1392.

Jaglo-Ottosen, K., et al., *Arabidopsis* CBF1 Overexpression Induces COR Genes and Enhances Freezing Tolerance, Science (Apr. 3, 1998) vol. 280, pp. 104-106.

Kirik, V., Simon, M., Huelskamp, M., and Schiefelbein, J. (Apr. 15, 2004a). The Enhancer of TRY and CPC1 gene acts redundantly with TRIPTYCHON and CAPRICE in trichome and root hair cell patterning in *Arabidopsis*. Dev Biol 268, 506-513.

Kirik, V., Simon, M., Wester, K., Schiefelbein, J., and Hulskamp, M. (May 2004b). Enhancer of TRY and CPC 2 (ETC2) reveals redundancy in the region-specific control of trichome development of *Arabidopsis*. Plant Mol Biol 55, 389-398.

Kirik V. et al (1998).: 'Two novel MYB homologues with changed expression in late embryogenesis-defective *Arabidopsis* mutants' Plant Mol. Biol. vol. 37, pp. 819-827, XP002938168.

Koziel, M.G. et al (Oct. 1996), "Optimizing expression of transgenes with an emphasis on post-transcriptional events." Plant Molecular Biology, vol. 32, pp. 393-405.

Li,, Zhongsen et al., "PEI1, an embryo-specific zinc finger protein gene required for heart-stage embryo formation in *Arabidopsis*," Plant Cell vol. 10, No. 3, Mar. 1998.

Lin, Xlaoying, et al., Sequence and analysis of chromosome 2 of the plant *Arabidopsis thaliana*, Nature (Dec. 16, 1999) vol. 402, pp. 761-768.

Mitsuhara, I., et al., Efficient Promoter Cassettes for Enhanced Expression of Foreign Genes in Dicotyledonous and Monocotyledonous Plants, Plant Cell Physiol. (Jan. 1996) 37(1):49-59.

Mouradov et al., NEEDLY, a *Pinus radiata* ortholog of FLORICAULA/LEAFY genes, expressed in both reproductive and vegetative meristems. Proc. Natl. Acad. Sci. U.S.A. May 1998; 95(11):6537-42.

Nandi et al., A conserved function for *Arabidopsis* SUPERMAN in regulating floral-whorl cell proliferation in rice, a monocotyledonous plant. Curr. Biol. Feb. 24, 2000; 10(4):215-8.

Ohme-Takagi et al., Ethylene-Inducible DNA Binding Proteins that interact with an ethylene-responsive element. The Plant Cell, vol. 7, 173-182, Feb. 1995.

Pena et al., Constitutive expression of *Arabidopsis* LEAFY or APETALA1 genes in citrus reduces their generation time. Nat. Biotechnol. Mar. 2001; 19(3):263-7.

Peng et al. (Jul. 15, 1999). 'Green revolution' genes encode mutant gibberellin response modulators, Nature 400:256-261.

Peng et al. (Apr. 1999), Extragenic suppressors of the *Arabidopsis* gai mutation alter the dose-response relationship of diverse gibberellin responses. Plant Physiol. 119(4):1199-208.

Razik and Quatrano, Effect of the Nuclear Factors EmBP1 and Viviparous1 on the Transcription of the Em Gene in HeLa Nuclear Extracts. The Plant Cell (Oct. 1997) vol. 9, pp. 1791-1803.

Rigola et al., CaMADS1, a MADS box gene expressed in the carpel of hazelnut. Plant Mol. Biol. Dec. 1998; 38(6):1147-60.

Rolland, et al., Sugar Sensing and Signaling in Plants. The Plant Cell (2002) Supplement 2002, S185-S205.

Rottmann et al., Diverse effects of overexpression of LEAFY and PTLF, a poplar (Populus) homolog of LEAFY/FLORICAULA, in transgenic poplar and *Arabidopsis*. Plant J. May 2000; 22(3):235-45.

Samach and Gover, Photoperiodism: The consistent use of CONSTANS. Curr. Biol. Aug. 21, 2001; 11(16):R651-4.

Sasaki, et al., The genome sequence and structure of rice chromosome 1. Nature (Nov. 21, 2002) 420 (6913), 312-316.

van der Valk et al., reported in EMBO Workshop. JIC Jul. 2001. Genetic transformation of perennial ryegrass with the *Arabidopsis* homeobox gene 1 (ath1) inhibits flowering.

Weigel and Nilsson (Oct. 12, 1995). A developmental switch sufficient for flower initiation in diverse plants. Nature 377:495-500.

White, J.A. et al., A new set of *Arabidopsis* expressed sequence tags from developing seed, Plant Physiol. 124(4) pp. 1582-1594 (Dec. 2000).

Winicov I, "New molecular approaches to improving salt tolerance in crop plants," Annals of Botany, vol. 82, No. 6 (Dec. 1998), pp. 705-710.

Winicov Ilga et al, "Transgenic overexpression of the transcription factor Alfin1 enhances expression of the endogenous MsPRP2 gene in alfalfa and improves salinity tolerance of the plants," Plant Physiology vol. 120, No. 2 (Jun. 1999) pp. 473-480.

Wu et al., The *Arabidopsis* 14-3-3 Multigene Family, Plant Physiol. (Aug. 1997) 114:1421-1431.

Yano et al. (Dec. 12, 2000), Hd1, a major photoperiod sensitivity quantitative trait locus in rice, is closely related to the *Arabidopsis* flowering time gene CONSTANS. Plant Cell. (12):2473-2484.

Yuan, L. and Knauf, V.C. "Modification of plant components." (Apr. 1, 1997) Current Opinion in Biotechnology, vol. 8, pp. 227-233.

Zhang, Y., Brown, G., Whetten, R., Loopstra, C.A., Neale, D., Kieliszewski, M.J., and Sederoff, R.R. (May 2003). An arabinogalactan protein associated with secondary cell wall formation in differentiating xylem of loblolly pine. Plant Mol Biol 52, 91-102.

Li S.F. et al.: 'A novel MYB-related gene from *Arabidopsis thaliana*' FEBS Letters vol. 379, 1996, pp. 117-121, XP002938163.

Suzuki A. et al.: 'Cloning and expression of five MYB-related genes from rice seed' Gene vol. 198, 1997, pp. 393-398, XP002938166.

Loguercio L.L. et al.: 'Differential regulation of six novel MYB-domain genes defines tow distinct expression in allotraploid cotton (*Gossypium hitsutum* L.)' Mol. Gen. Genet. vol. 261, 1999, pp. 660-671, XP002938167.

Hiei Y. et al. Efficient transformation of rice (*Oryza sativa* L.) mediated by *Agrobacterium* and sequence analysis of the boundaries of the T-DNA. Plant J. Aug. 1994;6(2):271-82.

Pang and Duggleby, Expression, purification, characterization, and reconstitution of the large and small subunits of yeast acetohydroxyacid synthase. Biochemistry (Apr. 20, 1999) 38(16):5222-31.

Larkin, J.C., Brown, M.L., and Schiefelbein, J. (2003). How do cells know what they want to be when they grow up? Lessons from epidermal patterning in *Arabidopsis*. Annu Rev Plant Biol 54, 403-430.

Graf, T. (Apr. 1992). Myb: a transcriptional activator linking proliferation and differentiation in hematopoietic cells. Curr Opin Genet Dev 2, 249-255.

Frampton, J., Gibson, T.J., Ness, S.A., Doderlein, G., and Graf, T. Dec. 1991). Proposed structure for the DNA-binding domain of the Myb oncoprotein based on model building and mutational analysis. Protein Eng 4, 891-901.

Elo et al., Three MADS-box genes similar to APETALA1 and FRUITFULL from silver birch (*BEtula pendula*). Physiol. Plant May 2001; 112(1):95-103.

Chandler and Bartels, Structure and function of the vp1 gene homologue from the resurrection plant *Craterostigma plantagineum* Hochst, Mol. Gen Genet (Nov. 1997) 256(5):539-46.

Merzlyak and Chivkunova (Apr. 2000), Light-stress-induced pigment changes and evidence for anthocyanin photoprotection in apples, J. Photochem Photobiol. B. 55(2-3):155-163.

Accession No. AB025613(Apr. 7, 1999). *Arabidopsis thaliana* genomic DNA, chromosome 5, TAC clone: K2I5, complete sequence.

Accession No. BG543096 (May 1, 2002). E0571 Chinese cabbage etiolated seedling library *Brassica rapa* subsp. pekinensis cDNA clone E0571, mRNA sequence.

Accession No. BH480897 (Dec. 13, 2001). BOGRA01TF BOGR *Brassica oleracea* genomic clone BOGRA01, genomic survey sequence.

Accession No. BG647027 (Apr. 24, 2001). EST508646 HOGA *Medicago truncatula* cDNA clone pHOGA-15O24 5- end, mRNA sequence.

Accession No. AAAA01000383 (Apr. 4, 2002). *Oryza sativa* (indica cultivar-group) scaffold000383, whole genome shotgun sequence.

Accession No. AP005755 (Sep. 19, 2002). *Oryza sativa* (japonica cultivar-group) chromosome 9 clone OSJNBb0019B14.

Accession No. BU023570 (Aug. 23, 2002). QHF11M19.yg.abl QH_EFGHJ sunflower RHA280 *Helianthus annuus* cDNA clone QHF11M19, mRNA sequence.

Accession No. BI426899 (Aug. 16, 2001). sag08g12.y1 Gm-c1080 *Glycine max* cDNA clone Genome Systems Clone ID: Gm-c1080-696 5- similar to TR:O22130 O22130 Putative PD1-Like DNA-Binding Protein. ;, mRNA sequence.

Accession No. BZ412041 (Dec. 4, 2002). OGACG56TC ZM_0.7_1.5_KB *Zea mays* genomic clone ZMMBMa0028J15, genomic survey sequence.

Accession No. AP004020 (Aug. 9, 2001). *Oryza sativa* (japonica cultivar-group) chromosome 2 clone OJ1119_A01.

Accession No. BM064716 (Sep. 11, 2002). KS01070D12 KS01 *Capsicum annuum* cDNA, mRNA sequence.

Accession No. AI965992.1 (Aug. 23, 1999). sc25a12.y1 Gm-c1013 *Glycine max* cDNA clone Genome Systems Clone ID: Gm-c1013-1655 5- similar to TR:O22130 O22130 Putative PD1-Like DNA-Binding Protein. ;, mRNA sequence.

Accession No. DT572760 (Oct. 31, 2005). EST1083400 GH_TMO *Gossypium hirsutum* cDNA, mRNA sequence.

Accession No. DR915235 (Aug. 2, 2005). EST1106774 *Aquilegia* cDNA library *Aquilegia formosa* × *Aquilegia pubescens* cDNA clone CO1LI40, mRNA sequence.

Accession No. DT574931 (Oct. 31, 2005). EST1085571 GH_TMO *Gossypium hirsutum* cDNA, mRNA sequence.

Accession No. AW647786 (Apr. 4, 2002). EST326240 tomato germinating seedlings, TAMU *Solanum lycopersicum* cDNA clone cLEI2C22 5-, mRNA sequence.

Accession No. BX901346 (Dec. 31, 2003). BX901346 *Oryza sativa* library (Han B) *Oryza sativa* cDNA clone p510d05p3, mRNA sequence.

Accession No. DT479592 (Aug. 29, 2005). WS02526.BR_F14 PT-MB-N-A-15 *Populus trichocarpa* cDNA clone WS02526_F14 5-, mRNA sequence.

Accession No. CK255678 (Dec. 12, 2003). EST739315 potato callus cDNA library, normalized and full-length *Solanum tuberosum* cDNA clone POCCN28 5- end, mRNA sequence.

Accession No. CN006086 (Mar. 26, 2004). CSECS128F04_CELu0001 CabSau Cell Culture (CELu0001) *Vitis vinifera* cDNA clone CSECS128F04 3-, mRNA sequence.

Accession No. CA920464 (Dec. 27, 2002). EST638182 MTUS *Medicago truncatula* cDNA clone MTUS-28E12, mRNA sequence.

Accession No. AV422959 (May 12, 2000). AV422959 *Lotus japonicus* young plants (two-week old) *Lotus japonicus* cDNA clone MWM020h01_r 5-, mRNA sequence.

Accession No. AJ831911 (Sep. 23, 2004). AJ831911 West Virginia 106 fruit 8 days post anthesis *Solanum lycopersicum* var. cerasiforme cDNA clone LE08DD12, mRNA sequence.

Accession No. CO167050 (Jun. 18, 2004). FLD1_66_A12.g1_A029 Root flooded *Pinus taeda* cDNA clone FLD1_66_A12_A029 5-, mRNA sequence.

Accession No. CK253622 (Dec. 12, 2003). EST737259 potato callus cDNA library, normalized and full-length *Solanum tuberosum* cDNA clone POCC687 5- end, mRNA sequence.

Accession No. BG510489 (Mar. 28, 2001). sac78f02.y1 Gm-c1072 *Glycine max* cDNA clone Genome Systems Clone ID: Gm-c1072-1420 5- similar to TR:Q9SZ70 Q9SZ70 Putative DNA-Binding Protein. ;, mRNA sequence.

Accession No. NM_124348 (TAIR No. AT5G49700) (May 2, 2003). *Arabidopsis thaliana* DNA-binding protein-related (AT5G49700) mRNA, complete cds . . . .

Accession No. NP_199781 (Aug. 21, 2001). DNA-binding protein-related [*Arabidopsis thaliana*].

Accession No. BAH30621 (Mar. 30, 2009). hypothetical protein [*Arabidopsis thaliana*].

Accession No. NP.172901 (Aug. 21, 2001). hypothetical protein [*Arabidopsis thaliana*].

Accession No. FAA00288 (Dec. 19, 2006). TPA: AT-hook motif nuclear localized protein 17 [*Arabidopsis thaliana*].

Accession No. BAC66727 (GI:29467557)(Feb. 16, 2008). DNA-binding protein-like [*Oryza sativa* Japonica Group].

Accession No. BAB64709 (GI:15528814) (Feb. 16, 2008). DNA-binding protein-like [*Oryza sativa* Japonica Group].

Accession No. CAA10643 (GI:4165183) ( Feb. 24, 2003). SAP1 protein [*Antirrhinum majus*].

Accession No. CAA67291 (GI:2213534) (Dec. 3, 2004). DNA-binding PD1-like protein [*Pisum sativum*].

Accession No. GI:78352486 (Oct. 31, 2005). EST1083400 GH_TMO *Gossypium hirsutum* cDNA, mRNA sequence.

Accession No. GI:71684598 (Aug. 2, 2005). EST1106774 *Aquilegia* cDNA library *Aquilegia formosa* × *Aquilegia pubescens* cDNA clone CO1LI40, mRNA sequence.

Accession No. GI:5760629 (Aug. 23, 1999). sc25a12.y1 Gm-c1013 *Glycine max* cDNA clone Genome Systems Clone ID: Gm-c1013-1655 5- similar to TR:O22130 O22130 Putative PD1-Like DNA-Binding Protein. ;, mRNA sequence.

Accession No. GI:78354657 (Oct. 31, 2005). EST1085571 GH_TMO *Gossypium hirsutum* cDNA, mRNA sequence.

Accession No. GI:7409024 (Apr. 4, 2000). EST326240 tomato germinating seedlings, TAMU *Solanum lycopersicum* cDNA clone cLEI2C22 5-, mRNA sequence.

Accession No. GI:13782139 (Apr. 24, 2001). EST508646 HOGA *Medicago truncatula* cDNA clone pHOGA-15O24 5- end, mRNA sequence.

Accession No. GI:40491102 (Dec. 31, 2003). BX901346 *Oryza sativa* library (Han B) *Oryza sativa* cDNA clone p510d05p3, mRNA sequence.

Accession No. GI:73876854 (Aug. 29, 2005). WS02526.BR_F14 PT-MB-N-A-15 *Populus trichocarpa* cDNA clone WS02526_F14 5-, mRNA sequence.

Accession No. GI:39812658 (Dec. 12, 2003). EST739315 potato callus cDNA library, normalized and full-length *Solanum tuberosum* cDNA clone POCCN28 5- end, mRNA sequence.

Accession No. GI:45770234 (Mar. 26, 2004). CSECS128F04_CELu0001 CabSau Cell Culture (CELu0001) *Vitis vinifera* cDNA clone CSECS128F04 3-, mRNA sequence.

Accession No. GI:27407394 (Dec. 27, 2002). EST638182 MTUS *Medicago truncatula* cDNA clone MTUS-28E12, mRNA sequence.

Accession No. GI:7778387 (May 10, 2000). AV422959 *Lotus japonicus* young plants (two-week old) *Lotus japonicus* cDNA clone MWM020h01_r 5-, mRNA sequence.

Accession No. GI:52619172 (Sep. 23, 2004). AJ831911 West Virginia 106 fruit 8 days post anthesis *Solanum lycopersicum* var. cerasiforme cDNA clone LE08DD12, mRNA sequence.
Accession No. GI:48937591 (Jun. 18, 2004). FLD1_66_A12.g1_A029 Root flooded *Pinus taeda* cDNA clone FLD1_66_A12_A029 5-, mRNA sequence.
Accession No. GI:39808730 (Dec. 12, 2003). EST737259 potato callus cDNA library, normalized and full-length *Solanum tuberosum* cDNA clone POCC687 5- end, mRNA sequence.
Accession No. GI:13481146 (Mar. 28, 2001). sac78f02.y1 Gm-c1072 *Glycine max* cDNA clone Genome Systems Clone ID: Gm-c1072-1420 5- similar to TR:Q9SZ70 Q9SZ70 Putative DNA-Binding Protein. ;, mRNA sequence.
U.S. Appl. No. 10/155,881, filed May 22, 2002, Kovalic, David.
NCBI Accession No. AL022604 (Apr. 24, 1998). *Arabidopsis thaliana* DNA chromosome 4, BAC clone F23E12 (ESSAII project).

* cited by examiner

*Primary Examiner* — Cynthia Collins
(74) *Attorney, Agent, or Firm* — Yifan Mao; Jeffery M. Libby

(57) ABSTRACT

Polynucleotides incorporated into expression vectors have been introduced into plants and were ectopically expressed. The encoded polypeptides of the invention have been shown to confer at least one regulatory activity and confer greater size, greater organ size, greater biomass, greater yield, curlier leaves, darker coloration, greater tolerance to water deprivation, delayed flowering, delayed development, delayed senescence, greater tolerance to cold, and/or greater tolerance to hyperosmotic stress as compared to a control plant.

19 Claims, 5 Drawing Sheets

| | | |
|---|---|---|
| G1945 | (2) | ------------------------------MKGEYREQKSNEMFSKLPHHQQQQQQQHSLT |
| G2155 | (4) | ------------------------------------------------MLSKLPTQR--- |
| G3936 | (6) | ----------------MKGEYVEQQQHPKSETPPSMFSKLQPQHHPFPHHPFQLSAE |
| G3408 | (8) | ------------MSFCERDMNKESMYQERDDMAGIRFATPPLPQQQQQLVECFSD |
| G597  | (18)| MSGSETGLMAATRESMQFTMALHQQQQHSQAQPQQSQNRPLSFGDDGTALYKQPMRSVS |
| | | |
| G1945 | (2) | SHF-----------HLSSTVTP-------TVDDSSIEVVRRPRGRPP------------ |
| G2155 | (4) | ---------------HLHLSPS--------SPSMETVGRPRGRPR-------------- |
| G3936 | (6) | DAT-----------TITPSTAQKANSSGGDGATIEVVRRPRGRPP-------------- |
| G3408 | (8) | EVDSRGSGGEMKDAVGSGSGQLVVVGGGDGASIEVAKKRRGRPP--------------- |
| G597  | (18)| PPQQYQPNSAGENSVLNMNLPGGESGGMTGTGSEPVKKRRGRPRKYGPDSGEMSLGLNPG |
| | | |
| | | At-hook |
| | | |
| G1945 | (2) | ------GSKNKPKPP----------VFVTRDTDP--PMSPYILEVPSGNDVVEAI |
| G2155 | (4) | ------GSKNKPKAP----------IFVT--IDP--PMSPYILEVPSGNDVVEAL |
| G3936 | (6) | ------GSKNKPKPP----------VIITRDPEP--AMSPYILEVSGGNDVVEAI |
| G3408 | (8) | ------GSKNKPKPP----------VVITREAEPAAAMRPHVIEIPGGRDVAEAL |
| G597  | (18)| APSFTVSQPSSGGDGGEKKRGRPPGSSSKRLKLQALGSTGIGETPHVLTVLAGEDVSSKI |
| | | At-hook          DUF296 |
| | | |
| G1945 | (2) | NRFCRRKSIGVCVLSGSGSVANVTLRQPSPAALGST---ITFHGKFDLLSVSATFLPPPP |
| G2155 | (4) | NRFCRGKAIGFCVLSGSGSVADVTLRQPSPAAPGST---ITFHGKFDLLSVSATFLPPLP |
| G3936 | (6) | AQFSHRKNMGICVLTGSGTVANVTLRQPS-TTPGTT---VTFHGRFDILSVSATFLPQ-- |
| G3408 | (8) | ARFSSRRNLGICVLAGTGAVANVSLRHPSPGVPGSAPAAIVFHGRYEILSLSATFLPP-A |
| G597  | (18)| MALTHNGPRAVCVLSANGAISNVTLRQSATSGGTVT----YEGRFEILSLSGSFHLLEN |
| | | DUF296 |

Fig. 4A

```
G1945  (2)  RTSLSP---PVSNFFTVSLAGPQGQIIGGFVAGPLISAGTVYVIAASFNNPSYHRLPAEE
G2155  (4)  PTSLSP---PVSNFFTVSLAGPQGQIIGGFVAGPLVAAGTVYFVATSFKNPSYHRLPATE
G3936  (6)  QSGASP---AVPNGFAISLAGPQGQIVGGLVAGGLMAAGTVFVIAASFNNPAYHRLPPEE
G3408  (8)  MSSVAPQAAVAAAGLSISLAGPHGQIVGGAVAGPLYAATTVVVAAAFTNPTFHRLPADD
G597  (10)  NGQRSR-----TGGLSVSLSSPDGNVLGGSVAGLLIAASPVQIVVGSFLPDGEKEPKQHV
                                                            ↑
                           DUF296

G1945  (2)  EQKHSAGTGER----------------EGQSPPVSGGGEESGQMAGSGGESCGVSM
G2155  (4)  EEQRNSAEGEE----------------EGQSPPVSG-----------GGGESM
G3936  (6)  EG---ASAGD-----------------GHSPPVSGGGDSG----HGQ-AESCGMSM
G3408  (8)  DASVSVSLSGSGDADEHRGHQHKPEPQEPRQLRRPPPHLSAAAAVSAAQPVEPCGAPM
G597  (10)  GQMGLSSPVLP----------------RVAPTQVLMTPSSPQSRGTMSESSCGGGH

G1945  (2)  YSCHMGGSDVIWAPTARAPPPY-----
G2155  (4)  Y---VGGSDVIWDPNAKAPSPY-----
G3936  (6)  YS-CHLPSDVIWAPTARPPPPPY----
G3408  (8)  YACHPQPQEVMWPPPARTPHPPPPPY
G597  (10)  GSPIHQSTGGPYNNTINMPWK------
```

Fig. 4B

```
                       SEQUENCE LISTING

<160> NUMBER OF SEQ ID NOS: 49

<210> SEQ ID NO 1
<211> LENGTH: 1130
<212> TYPE: DNA
<213> ORGANISM: Arabidopsis thaliana
<220> FEATURE:
<223> OTHER INFORMATION: G1945

<400> SEQUENCE: 1
atttcccaaa gggatttacg aaaagtccct ctcctctatc atctctttat tcaccccata      60
ccaacaacct ctacatcttc ttcttcttct tcctcctctt ttattttctt tttaaatcat     120
ttacacaaaa atccaaagac aaatctgaaa tctctaataa acaaatccat aaaataagaa     180
aaacaaagat gaaaggtgaa tacagagagc aaaagagtaa cgaaatgttt tccaagcttc     240
ctcatcatca acaacaacag caacaacaac aacaacaaca ctctcttacc tctcacttcc     300
acctctcctc caccgtaacc cccaccgtcg atgactcctc catcgaagtg gtccgacgtc     360
cacgtggcag accaccaggt tccaaaaaca aacctaaacc acccgtcttc gtcacacgtg     420
acaccgaccc tcctatgagt ccttacatcc tcgaagttcc ttcaggaaac gacgtcgtcg     480
aagccatcaa ccgtttctgc cgccgtaaat ccatcggagt ctgcgtcctt agtggctctg     540
gctctgtagc taacgtcact ttacgtcagc catcaccggc agctcttggc tctaccataa     600
ctttccatgg aaagtttgat ctcctctccg tctccgcaac gtttctccct cctccgcctc     660
gtacttcctt gtctcctccc gtttctaact tcttcaccgt ctctctcgct ggacctcaag     720
gacaaatcat cggagggttc gtcgctggtc cacttatttc ggcaggaaca gtttacgtca     780
tcgccgcaag tttcaacaac ccttcttatc accggttacc ggcggaagaa gagcaaaaac     840
```

```
actcggcggg gacaggggaa agagagggac aatctccgcc ggtctctggt ggcggtgaag      900
agtcaggaca gatggcggga agtggaggag agtcgtgtgg ggtatcaatg tacagttgcc      960
acatgggtgg ctctgatgtt atttgggccc ctacagccag agctccaccg ccatactaac     1020
caatccttct ttcacaaatc tctttctttc tttttttgtt ttttttgtt ttgggttagg     1080 atgaatcaag aaactagggt tttttttttt ttttttaaa aaaaaaaaa                  1130
```

```
<210> SEQ ID NO 2
<211> LENGTH: 276
<212> TYPE: PRT
<213> ORGANISM: Arabidopsis thaliana
<220> FEATURE:
<223> OTHER INFORMATION: G1945 polypeptide

<400> SEQUENCE: 2
```

```
Met Lys Gly Glu Tyr Arg Glu Gln Lys Ser Asn Glu Met Phe Ser Lys
1               5                   10                  15

Leu Pro His His Gln Gln Gln Gln Gln Gln Gln Gln Gln His Ser
            20                  25                  30

Leu Thr Ser His Phe His Leu Ser Ser Val Thr Pro Thr Val Asp
        35                  40                  45

Asp Ser Ser Ile Glu Val Val Arg Arg Pro Arg Gly Arg Pro Pro Gly
    50                  55                  60

Ser Lys Asn Lys Pro Lys Pro Val Phe Val Thr Arg Asp Thr Asp
65                  70                  75                  80

Pro Pro Met Ser Pro Tyr Ile Leu Glu Val Pro Ser Gly Asn Asp Val
                85                  90                  95

Val Glu Ala Ile Asn Arg Phe Cys Arg Arg Lys Ser Ile Gly Val Cys
            100                 105                 110

Val Leu Ser Gly Ser Gly Ser Val Ala Asn Val Thr Leu Arg Gln Pro
        115                 120                 125

Ser Pro Ala Ala Leu Gly Ser Thr Ile Thr Phe His Gly Lys Phe Asp
    130                 135                 140

Leu Leu Ser Val Ser Ala Thr Phe Leu Pro Pro Pro Arg Thr Ser
145                 150                 155                 160

Leu Ser Pro Pro Val Ser Asn Phe Phe Thr Val Ser Leu Ala Gly Pro
                165                 170                 175

Gln Gly Gln Ile Ile Gly Gly Phe Val Ala Gly Pro Leu Ile Ser Ala
            180                 185                 190

Gly Thr Val Tyr Val Ile Ala Ala Ser Phe Asn Asn Pro Ser Tyr His
        195                 200                 205

Arg Leu Pro Ala Glu Glu Gln Lys His Ser Ala Gly Thr Gly Glu
    210                 215                 220

Arg Glu Gly Gln Ser Pro Pro Val Ser Gly Gly Glu Glu Ser Gly
225                 230                 235                 240

Gln Met Ala Gly Ser Gly Glu Ser Cys Gly Val Ser Met Tyr Ser
                245                 250                 255

Cys His Met Gly Gly Ser Asp Val Ile Trp Ala Pro Thr Ala Arg Ala
            260                 265                 270

Pro Pro Pro Tyr
        275
```

```
<210> SEQ ID NO 3
<211> LENGTH: 1050
<212> TYPE: DNA
<213> ORGANISM: Arabidopsis thaliana
```

```
<220> FEATURE:
<223> OTHER INFORMATION: G2155

<400> SEQUENCE: 3
ctcatatata ccaaccaaac ctctctctgc atctttatta acacaaaatt ccaaaagatt      60
aaatgttgtc gaagctccct acacagcgac acttgcacct ctctccctcc tctccctcca     120
tggaaaccgt cgggcgtcca cgtggcagac ctcgaggttc caaaaacaaa cctaaagctc     180
caatctttgt caccattgac cctcctatga gtccttacat cctcgaagtg ccatccggaa     240
acgatgtcgt tgaagcccta aaccgtttct gccgcggtaa agccatcggc ttttgcgtcc     300
tcagtggctc aggctccgtt gctgatgtca ctttgcgtca gccttctccg gcagctcctg     360
gctcaaccat tactttccac ggaaagttcg atcttctctc tgtctccgcc actttcctcc     420
ctcctctacc tcctacctcc ttgtcccctc ccgtctccaa tttcttcacc gtctctctcg     480
ccggacctca ggggaaagtc atcggtggat tcgtcgctgg tcctctcgtt gccgccggaa     540
ctgtttactt cgtcgccact agtttcaaga acccttccta tcaccggtta cctgctacgg     600
aggaagagca agaaactcg gcggaagggg aagaggaggg acaatcgccg ccggtctctg      660
gaggtggtgg agagtcgatg tacgtgggtg gctctgatgt catttgggat cccaacgcca     720
aagctccatc gccgtactga ccacaaatcc atctcgttca aactagggtt tcttcttctt     780
tagatcatca agaatcaaca aaaagattgc attttttgat tctttgtaat atcataattg     840
actcactctt taatctctct atcacttctt ctttagcttt ttctgcagtg tcaaacttca     900
catatttgta gtttgatttg actatcccca agttttgtat tttatcatac aaattttttgc    960 ctgtctctaa tggttgtttt ttcgtttgta taatcttatg cattgtttat tggagctcca    1020
gagattgaat gtataatata atggtttaat                                     1050

<210> SEQ ID NO 4
<211> LENGTH: 225
<212> TYPE: PRT
<213> ORGANISM: Arabidopsis thaliana
<220> FEATURE:
<223> OTHER INFORMATION: G2155 polypeptide

<400> SEQUENCE: 4

Met Leu Ser Lys Leu Pro Thr Gln Arg His Leu His Leu Ser Pro Ser
1               5                  10                  15

Ser Pro Ser Met Glu Thr Val Gly Arg Pro Arg Gly Arg Pro Arg Gly
            20                  25                  30

Ser Lys Asn Lys Pro Lys Ala Pro Ile Phe Val Thr Ile Asp Pro Pro
        35                  40                  45

Met Ser Pro Tyr Ile Leu Glu Val Pro Ser Gly Asn Asp Val Val Glu
    50                  55                  60

Ala Leu Asn Arg Phe Cys Arg Gly Lys Ala Ile Gly Phe Cys Val Leu
65                  70                  75                  80

Ser Gly Ser Gly Ser Val Ala Asp Val Thr Leu Arg Gln Pro Ser Pro
                85                  90                  95

Ala Ala Pro Gly Ser Thr Ile Thr Phe His Gly Lys Phe Asp Leu Leu
            100                 105                 110

Ser Val Ser Ala Thr Phe Leu Pro Pro Leu Pro Pro Thr Ser Leu Ser
        115                 120                 125

Pro Pro Val Ser Asn Phe Phe Thr Val Ser Leu Ala Gly Pro Gln Gly
    130                 135                 140

Lys Val Ile Gly Gly Phe Val Ala Gly Pro Leu Val Ala Ala Gly Thr
145                 150                 155                 160
```

```
Val Tyr Phe Val Ala Thr Ser Phe Lys Asn Pro Ser Tyr His Arg Leu
                165                 170                 175

Pro Ala Thr Glu Glu Glu Gln Arg Asn Ser Ala Glu Gly Glu Gln Glu
            180                 185                 190

Gly Gln Ser Pro Pro Val Ser Gly Gly Gly Glu Ser Met Tyr Val
        195                 200                 205

Gly Gly Ser Asp Val Ile Trp Asp Pro Asn Ala Lys Ala Pro Ser Pro
    210                 215                 220

Tyr
225

<210> SEQ ID NO 5
<211> LENGTH: 1126
<212> TYPE: DNA
<213> ORGANISM: Glycine max
<220> FEATURE:
<223> OTHER INFORMATION: G3936

<400> SEQUENCE: 5
ctcctttctt tctccacttg atttttttac aataacccaa tcatagtctc actcgggatt    60
ggttattctt attctaagag ataatccaaa tccaaaccca aaagaacaac acaatgaaag   120
gagaatacgt agagcaacag caacaacatc ctaagagtga acaccacct agtatgttct    180 caaagcttca gcctcagcac catcctttcc cgcaccaccc tttccaactc tccgccgagg   240
atgccaccac catcacccg agcaccgctc agaaggccaa ctcctccggc ggcgacggcg    300
cgaccatcga ggttgttcgg cgtcccaggg gacgtccgcc cgggtccaaa aacaagccca   360
agccaccggt tatcataacc cgtgacccgg aacccgctat gagtccctac attttagaag   420
tgtctggcgg aaacgacgtc gtcgaggcca tcgcgcagtt cagtcaccgc aagaacatgg   480
gaatctgcgt cctcacgggt tctggaaccg tcgctaacgt cacgctccgt caaccttcca   540
ccacgcccgg caccaccgtt acttttcacg gccgtttcga catcctttct gtttccgcca   600
ccttccttcc gcagcagtcc ggcgcttctc cggcggttcc caacggattc gccatctcgc   660
tcgccggacc gcaggggcag atcgtcgag acttgttgc cggcgggctg atggctgccg    720
ggactgtttt tgtgatcgct gcctcgttca acaacccggc ataccacagg cttccgccgg   780
aggaagaggg cgcctccgcc ggagatggac attcgccgcc agtctccggc ggcggagaca   840
gcgggcatgg acaggcggag tcgtgtggaa tgtccatgta cagctgtcac ttgccctctg   900
atgtgatttg ggctccaacg gctagaccac cgccgccgcc ttactgatcg atcaatcaca   960
cgtcgagttt ctgtttcttt tcttctgag gttaactttg tggttattgt aatcaattct   1020
actatatgtt gctctgtta aatttgattta gttggtgtag ttgatatatc tggtattagt   1080
ttaactatta ttattattat tataattagg ttaagtttat aaatgg                 1126

<210> SEQ ID NO 6
<211> LENGTH: 277
<212> TYPE: PRT
<213> ORGANISM: Glycine max
<220> FEATURE:
<223> OTHER INFORMATION: G3936 polypeptide

<400> SEQUENCE: 6

Met Lys Gly Glu Tyr Val Glu Gln Gln Gln Gln His Pro Lys Ser Glu
1               5                   10                  15

Thr Pro Pro Ser Met Phe Ser Lys Leu Gln Pro Gln His His Pro Phe
            20                  25                  30
```

```
Pro His His Pro Phe Gln Leu Ser Ala Glu Asp Ala Thr Thr Ile Thr
         35                  40                  45

Pro Ser Thr Ala Gln Lys Ala Asn Ser Ser Gly Gly Asp Gly Ala Thr
 50                  55                  60

Ile Glu Val Val Arg Arg Pro Arg Gly Arg Pro Pro Gly Ser Lys Asn
 65                  70                  75                  80

Lys Pro Lys Pro Pro Val Ile Ile Thr Arg Asp Pro Glu Pro Ala Met
                 85                  90                  95

Ser Pro Tyr Ile Leu Glu Val Ser Gly Gly Asn Asp Val Val Glu Ala
            100                 105                 110

Ile Ala Gln Phe Ser His Arg Lys Asn Met Gly Ile Cys Val Leu Thr
        115                 120                 125

Gly Ser Gly Thr Val Ala Asn Val Thr Leu Arg Gln Pro Ser Thr Thr
130                 135                 140

Pro Gly Thr Thr Val Thr Phe His Gly Arg Phe Asp Ile Leu Ser Val
145                 150                 155                 160

Ser Ala Thr Phe Leu Pro Gln Gln Ser Gly Ala Ser Pro Ala Val Pro
                165                 170                 175

Asn Gly Phe Ala Ile Ser Leu Ala Gly Pro Gln Gly Gln Ile Val Gly
            180                 185                 190

Gly Leu Val Ala Gly Gly Leu Met Ala Ala Gly Thr Val Phe Val Ile
        195                 200                 205

Ala Ala Ser Phe Asn Asn Pro Ala Tyr His Arg Leu Pro Pro Glu Glu
210                 215                 220

Glu Gly Ala Ser Ala Gly Asp Gly His Ser Pro Pro Val Ser Gly Gly
225                 230                 235                 240

Gly Asp Ser Gly His Gly Gln Ala Glu Ser Cys Gly Met Ser Met Tyr
                245                 250                 255

Ser Cys His Leu Pro Ser Asp Val Ile Trp Ala Pro Thr Ala Arg Pro
            260                 265                 270

Pro Pro Pro Pro Tyr
            275

<210> SEQ ID NO 7
<211> LENGTH: 1064
<212> TYPE: DNA
<213> ORGANISM: Oryza sativa
<220> FEATURE:
<223> OTHER INFORMATION: G3408

<400> SEQUENCE: 7
gtggttttgg ttgattgcta ctctgtgcca tgtcgttctg cgagagggac atgaacaagg      60
agagcatgta ccaagaacgg gacgacatgg cggggatacg gttcgcgacg ccgccgctgc     120
ctcagcagca gcagcagcag cagctggtgg agtgcttctc cgacgaggtg gacagccgcg     180
ggagtggcgg cgagatgaag gatgccgtgg ggagcgggag tggcagctg gtcgttgttg      240 gtggcgggga tgggcgagc atcgaggtgg cgaagaagag gaggggagg ccgccggggt       300 ccaagaacaa gccgaagcca cccgtggtga tcacgcggga ggcggagccg cgggcggcga     360
tgcggccgca cgtgatcgag atccccggcg ggcgggacgt cgcggaggcg ctcgcgcggt     420
tctcgagccg tcgaacctc gggatctgcg tgctcgccgg caccggcgcg tcgccaacg      480 tgtcgctccg ccacccgtca cccggggtcc cgggctcagc tccggctgcg atcgtgttcc     540
acggccggta cgagatcctc tccctgtcgg ccacgttcct gctccggcc atgtcctccg      600 tggcgcccca ggccgcggtc gccgccgcgg gcctctccat ctcgctcgcc ggcccgcacg     660
```

```
gccagatcgt cggcggggcc gtggcaggcc cgctctacgc cgcgaccacc gtcgtggtcg    720
tcgccgccgc cttcaccaac cccaccttcc accgcctccc cgccgacgac gacgcgtcgg    780
tgtccgtctc ggtgtcactc tccggcagcg gcgacgcgga cgaacaccgg ggccaccagc    840
acaaacctga gccgcaagaa ccgcgccaac ttcgacggcc gccaccgcac ctgtcagcag    900
ccgccgccgt ctcagcagca cagccggtgg agccatgcgg cgcgcccatg tacgcctgcc    960
accctcagcc acaggaggtg atgtggccgc cgccggctcg tacgccgcac ccgccgccgc   1020
cgccgccgta ctaatccgac cgaattggta cgccattgcc acat                    1064
```

<210> SEQ ID NO 8
<211> LENGTH: 334
<212> TYPE: PRT
<213> ORGANISM: Oryza sativa
<220> FEATURE:
<223> OTHER INFORMATION: G3408 polypeptide

<400> SEQUENCE: 8

```
Met Ser Phe Cys Glu Arg Asp Met Asn Lys Glu Ser Met Tyr Gln Glu
 1               5                  10                  15

Arg Asp Asp Met Ala Gly Ile Arg Phe Ala Thr Pro Pro Leu Pro Gln
            20                  25                  30

Gln Gln Gln Gln Gln Gln Leu Val Glu Cys Phe Ser Asp Glu Val Asp
        35                  40                  45

Ser Arg Gly Ser Gly Gly Glu Met Lys Asp Ala Val Gly Ser Gly Ser
    50                  55                  60

Gly Gln Leu Val Val Val Gly Gly Asp Gly Ala Ser Ile Glu Val
65                  70                  75                  80

Ala Lys Lys Arg Arg Gly Arg Pro Pro Gly Ser Lys Asn Lys Pro Lys
                85                  90                  95

Pro Pro Val Val Ile Thr Arg Glu Ala Glu Pro Ala Ala Ala Met Arg
           100                 105                 110

Pro His Val Ile Glu Ile Pro Gly Gly Arg Asp Val Ala Glu Ala Leu
       115                 120                 125

Ala Arg Phe Ser Ser Arg Arg Asn Leu Gly Ile Cys Val Leu Ala Gly
    130                 135                 140

Thr Gly Ala Val Ala Asn Val Ser Leu Arg His Pro Ser Pro Gly Val
145                 150                 155                 160

Pro Gly Ser Ala Pro Ala Ala Ile Val Phe His Gly Arg Tyr Glu Ile
                165                 170                 175

Leu Ser Leu Ser Ala Thr Phe Leu Pro Pro Ala Met Ser Ser Val Ala
            180                 185                 190

Pro Gln Ala Ala Val Ala Ala Ala Gly Leu Ser Ile Ser Leu Ala Gly
        195                 200                 205

Pro His Gly Gln Ile Val Gly Gly Ala Val Ala Gly Pro Leu Tyr Ala
    210                 215                 220

Ala Thr Thr Val Val Val Val Ala Ala Ala Phe Thr Asn Pro Thr Phe
225                 230                 235                 240

His Arg Leu Pro Ala Asp Asp Ala Ser Val Ser Val Ser Val Ser
                245                 250                 255

Leu Ser Gly Ser Gly Asp Ala Asp Glu His Arg Gly His Gln His Lys
            260                 265                 270

Pro Glu Pro Gln Glu Pro Arg Gln Leu Arg Arg Pro Pro His Leu
        275                 280                 285

Ser Ala Ala Ala Ala Val Ser Ala Ala Gln Pro Val Glu Pro Cys Gly
    290                 295                 300
```

```
Ala Pro Met Tyr Ala Cys His Pro Gln Pro Gln Glu Val Met Trp Pro
305                 310                 315                 320

Pro Pro Ala Arg Thr Pro His Pro Pro Pro Pro Pro Tyr
                325                 330
```

<210> SEQ ID NO 9
<211> LENGTH: 9
<212> TYPE: PRT
<213> ORGANISM: Arabidopsis thaliana
<220> FEATURE:
<223> OTHER INFORMATION: G1945 AT hook domain

<400> SEQUENCE: 9

```
Arg Arg Pro Arg Gly Arg Pro Pro Gly
1               5
```

<210> SEQ ID NO 10
<211> LENGTH: 9
<212> TYPE: PRT
<213> ORGANISM: Arabidopsis thaliana
<220> FEATURE:
<223> OTHER INFORMATION: G2155 AT hook domain

<400> SEQUENCE: 10

```
Gly Arg Pro Arg Gly Arg Pro Arg Gly
1               5
```

<210> SEQ ID NO 11
<211> LENGTH: 9
<212> TYPE: PRT
<213> ORGANISM: Glycine max
<220> FEATURE:
<223> OTHER INFORMATION: G3936 AT hook domain

<400> SEQUENCE: 11

```
Arg Arg Pro Arg Gly Arg Pro Pro Gly
1               5
```

<210> SEQ ID NO 12
<211> LENGTH: 9
<212> TYPE: PRT
<213> ORGANISM: Oryza sativa
<220> FEATURE:
<223> OTHER INFORMATION: G3408 AT hook domain

<400> SEQUENCE: 12

```
Lys Lys Arg Arg Gly Arg Pro Pro Gly
1               5
```

<210> SEQ ID NO 13
<211> LENGTH: 125
<212> TYPE: PRT
<213> ORGANISM: Arabidopsis thaliana
<220> FEATURE:
<223> OTHER INFORMATION: G1945 DUF296 domain

<400> SEQUENCE: 13

```
Met Ser Pro Tyr Ile Leu Glu Val Pro Ser Gly Asn Asp Val Val Glu
1               5                   10                  15

Ala Ile Asn Arg Phe Cys Arg Arg Lys Ser Ile Gly Val Cys Val Leu
                20                  25                  30

Ser Gly Ser Gly Ser Val Ala Asn Val Thr Leu Arg Gln Pro Ser Pro
            35                  40                  45

Ala Ala Leu Gly Ser Thr Ile Thr Phe His Gly Lys Phe Asp Leu Leu
        50                  55                  60
```

```
Ser Val Ser Ala Thr Phe Leu Pro Pro Pro Arg Thr Ser Leu Ser
 65                  70                  75                  80

Pro Pro Val Ser Asn Phe Phe Thr Val Ser Leu Ala Gly Pro Gln Gly
                 85                  90                  95

Gln Ile Ile Gly Gly Phe Val Ala Gly Pro Leu Ile Ser Ala Gly Thr
            100                 105                 110

Val Tyr Val Ile Ala Ala Ser Phe Asn Asn Pro Ser Tyr
        115                 120                 125

<210> SEQ ID NO 14
<211> LENGTH: 125
<212> TYPE: PRT
<213> ORGANISM: Arabidopsis thaliana
<220> FEATURE:
<223> OTHER INFORMATION: G2155 DUF296 domain

<400> SEQUENCE: 14

Met Ser Pro Tyr Ile Leu Glu Val Pro Ser Gly Asn Asp Val Val Glu
 1               5                  10                  15

Ala Leu Asn Arg Phe Cys Arg Gly Lys Ala Ile Gly Phe Cys Val Leu
            20                  25                  30

Ser Gly Ser Gly Ser Val Ala Asp Val Thr Leu Arg Gln Pro Ser Pro
        35                  40                  45

Ala Ala Pro Gly Ser Thr Ile Thr Phe His Gly Lys Phe Asp Leu Leu
    50                  55                  60

Ser Val Ser Ala Thr Phe Leu Pro Pro Leu Pro Pro Thr Ser Leu Ser
 65                  70                  75                  80

Pro Pro Val Ser Asn Phe Phe Thr Val Ser Leu Ala Gly Pro Gln Gly
                 85                  90                  95

Lys Val Ile Gly Gly Phe Val Ala Gly Pro Leu Val Ala Ala Gly Thr
            100                 105                 110

Val Tyr Phe Val Ala Thr Ser Phe Lys Asn Pro Ser Tyr
        115                 120                 125

<210> SEQ ID NO 15
<211> LENGTH: 121
<212> TYPE: PRT
<213> ORGANISM: Glycine max
<220> FEATURE:
<223> OTHER INFORMATION: G3936 DUF296 domain

<400> SEQUENCE: 15

Ser Pro Tyr Ile Leu Glu Val Ser Gly Gly Asn Asp Val Val Glu Ala
 1               5                  10                  15

Ile Ala Gln Phe Ser His Arg Lys Asn Met Gly Ile Cys Val Leu Thr
            20                  25                  30

Gly Ser Gly Thr Val Ala Asn Val Thr Leu Arg Gln Pro Ser Thr Thr
        35                  40                  45

Pro Gly Thr Thr Val Thr Phe His Gly Arg Phe Asp Ile Leu Ser Val
    50                  55                  60

Ser Ala Thr Phe Leu Pro Gln Gln Ser Gly Ala Ser Pro Ala Val Pro
 65                  70                  75                  80

Asn Gly Phe Ala Ile Ser Leu Ala Gly Pro Gln Gly Gln Ile Val Gly
                 85                  90                  95

Gly Leu Val Ala Gly Gly Leu Met Ala Ala Gly Thr Val Phe Val Ile
            100                 105                 110

Ala Ala Ser Phe Asn Asn Pro Ala Tyr
        115                 120
```

<210> SEQ ID NO 16
<211> LENGTH: 130
<212> TYPE: PRT
<213> ORGANISM: Oryza sativa
<220> FEATURE:
<223> OTHER INFORMATION: G3408 DUF296 domain

<400> SEQUENCE: 16

```
Met Arg Pro His Val Ile Glu Ile Pro Gly Gly Arg Asp Val Ala Glu
1               5                   10                  15
Ala Leu Ala Arg Phe Ser Ser Arg Arg Asn Leu Gly Ile Cys Val Leu
            20                  25                  30
Ala Gly Thr Gly Ala Val Ala Asn Val Ser Leu Arg His Pro Ser Pro
        35                  40                  45
Gly Val Pro Gly Ser Ala Pro Ala Ala Ile Val Phe His Gly Arg Tyr
    50                  55                  60
Glu Ile Leu Ser Leu Ser Ala Thr Phe Leu Pro Pro Ala Met Ser Ser
65                  70                  75                  80
Val Ala Pro Gln Ala Ala Val Ala Ala Ala Gly Leu Ser Ile Ser Leu
                85                  90                  95
Ala Gly Pro His Gly Gln Ile Val Gly Gly Val Ala Gly Pro Leu
            100                 105                 110
Tyr Ala Ala Thr Thr Val Val Val Ala Ala Ala Phe Thr Asn Pro
            115                 120                 125
Thr Phe
    130
```

<210> SEQ ID NO 17
<211> LENGTH: 1538
<212> TYPE: DNA
<213> ORGANISM: Arabidopsis thaliana
<220> FEATURE:
<223> OTHER INFORMATION: G597

<400> SEQUENCE: 17

```
aaaattctcc tgtaaaattt aatattataa aagtggtttc ttttcatttt atgtttatat      60
aattttcatc tttaatctta aattctggta accttaatgc gcgatccgct tttctaaagt     120
tttgtgagag agaagagatc taaaaaaatc cacaattttg ttcaaatctt ggagttaaat     180
gctgaatttt aggccttgtt gcttagattt atggcttaaa gtttcaaact tttcattgga     240
tatgtgagaa gaaaatgtca ggatctgaga cgggttaat ggcggcgacc agagaatcaa      300
tgcaatttac aatggctctc caccagcagc agcaacacag tcaagctcaa cctcagcagt     360
ctcagaacag gccattgtca ttcggtggag acgacggaac tgctctttac aagcagccga     420
tgagatcagt atcaccaccg cagcagtacc aacccaactc agctggtgag aattctgtct     480
tgaacatgaa cttgcccgga ggtgagtctg gaggcatgac tggaactgga agtgagccag     540
tgaaaaagag gagaggtaga ccgaggaaat atgggcctga tagtggtgaa atgtcacttg     600
gtttgaatcc tggagctcct tctttcactg tcagccaacc tagtagcggc ggcgatggag     660
gagagaagaa gagaggaaga cctcctggtt cttctagcaa aaggctcaag cttcaagctt     720
taggctcgac tggaatcgga tttacgcctc atgtacttac cgtgctggct ggagaggatg     780
tatcatccaa gataatggcg ttaactcata atggaccccg tgctgtgtgt gtcttgtctg     840
caaatggagc catctccaat gtgactctcc gccagtctgc cacatccggt ggaactgtta     900
catatgaggg gagatttgag attctgtctt tatcgggatc tttccatttg ctggagaaca     960
```

-continued

```
atggtcaaag aagcaggacg ggaggtctaa gcgtgtcatt atcaagtccg gatggtaatg    1020
tcctcggtgg cagtgtagct ggtcttctta tagcagcatc acctgttcag attgttgttg    1080 ggagttttctt accagacgga gaaaagaac caaaacagca tgtgggacaa atgggactgt    1140
cgtcacccgt attaccgcgt gtggcccaa cgcaggtgct gatgactcca agtagcccac    1200
aatctcgagg cacaatgagt gagtcatctt gtggaggagg acatggaagc cctattcatc    1260
agagcactgg aggaccttac aataacacca ttaacatgcc ctggaagtag ccaagtgatc    1320
tgtgtcggct taaaccaac aacttcccgt tattagagtg atttatttct acatttggtt    1380
tagactttct agttctgatg gttatttcta cagttggttt agactttcta gttctgttca    1440
gacaaaagga gtttgataaa ttgaccgacc tattttgtgt gtttgaggta ctttcagaac    1500
cataggtgtt cagaaattag aatgttctgt ttaaaaaa                            1538
```

<210> SEQ ID NO 18
<211> LENGTH: 351
<212> TYPE: PRT
<213> ORGANISM: Arabidopsis thaliana
<220> FEATURE:
<223> OTHER INFORMATION: G597 polypeptide

<400> SEQUENCE: 18

```
Met Ser Gly Ser Glu Thr Gly Leu Met Ala Ala Thr Arg Glu Ser Met
1               5                   10                  15

Gln Phe Thr Met Ala Leu His Gln Gln Gln His Ser Gln Ala Gln
            20                  25                  30

Pro Gln Gln Ser Gln Asn Arg Pro Leu Ser Phe Gly Gly Asp Asp Gly
        35                  40                  45

Thr Ala Leu Tyr Lys Gln Pro Met Arg Ser Val Ser Pro Pro Gln Gln
    50                  55                  60

Tyr Gln Pro Asn Ser Ala Gly Glu Asn Ser Val Leu Asn Met Asn Leu
65                  70                  75                  80

Pro Gly Gly Glu Ser Gly Gly Met Thr Gly Thr Gly Ser Glu Pro Val
                85                  90                  95

Lys Lys Arg Arg Gly Arg Pro Arg Lys Tyr Gly Pro Asp Ser Gly Glu
            100                 105                 110

Met Ser Leu Gly Leu Asn Pro Gly Ala Pro Ser Phe Thr Val Ser Gln
        115                 120                 125

Pro Ser Ser Gly Gly Asp Gly Gly Glu Lys Lys Arg Gly Arg Pro Pro
    130                 135                 140

Gly Ser Ser Ser Lys Arg Leu Lys Leu Gln Ala Leu Gly Ser Thr Gly
145                 150                 155                 160

Ile Gly Phe Thr Pro His Val Leu Thr Val Leu Ala Gly Glu Asp Val
                165                 170                 175

Ser Ser Lys Ile Met Ala Leu Thr His Asn Gly Pro Arg Ala Val Cys
            180                 185                 190

Val Leu Ser Ala Asn Gly Ala Ile Ser Asn Val Thr Leu Arg Gln Ser
        195                 200                 205

Ala Thr Ser Gly Gly Thr Val Thr Tyr Glu Gly Arg Phe Glu Ile Leu
    210                 215                 220

Ser Leu Ser Gly Ser Phe His Leu Leu Glu Asn Asn Gly Gln Arg Ser
225                 230                 235                 240

Arg Thr Gly Gly Leu Ser Val Ser Leu Ser Ser Pro Asp Gly Asn Val
                245                 250                 255

Leu Gly Gly Ser Val Ala Gly Leu Leu Ile Ala Ala Ser Pro Val Gln
            260                 265                 270
```

```
Ile Val Val Gly Ser Phe Leu Pro Asp Gly Glu Lys Glu Pro Lys Gln
            275                 280                 285

His Val Gly Gln Met Gly Leu Ser Ser Pro Val Leu Pro Arg Val Ala
            290                 295                 300

Pro Thr Gln Val Leu Met Thr Pro Ser Ser Pro Gln Ser Arg Gly Thr
305                 310                 315                 320

Met Ser Glu Ser Ser Cys Gly Gly His Gly Ser Pro Ile His Gln
            325                 330                 335

Ser Thr Gly Gly Pro Tyr Asn Asn Thr Ile Asn Met Pro Trp Lys
            340                 345                 350

<210> SEQ ID NO 19
<211> LENGTH: 9
<212> TYPE: PRT
<213> ORGANISM: Arabidopsis thaliana
<220> FEATURE:
<223> OTHER INFORMATION: G597 AT hook domain

<400> SEQUENCE: 19

Glu Lys Lys Arg Gly Arg Pro Pro Lys
1               5

<210> SEQ ID NO 20
<211> LENGTH: 116
<212> TYPE: PRT
<213> ORGANISM: Arabidopsis thaliana
<220> FEATURE:
<223> OTHER INFORMATION: G597 DUF296 domain

<400> SEQUENCE: 20

Phe Thr Pro His Val Leu Thr Val Leu Ala Gly Glu Asp Val Ser Ser
1               5                   10                  15

Lys Ile Met Ala Leu Thr His Asn Gly Pro Arg Ala Val Cys Val Leu
            20                  25                  30

Ser Ala Asn Gly Ala Ile Ser Asn Val Thr Leu Arg Gln Ser Ala Thr
        35                  40                  45

Ser Gly Gly Thr Val Thr Tyr Glu Gly Arg Phe Glu Ile Leu Ser Leu
    50                  55                  60

Ser Gly Ser Phe His Leu Leu Glu Asn Asn Gly Gln Arg Ser Arg Thr
65                  70                  75                  80

Gly Gly Leu Ser Val Ser Leu Ser Ser Pro Asp Gly Asn Val Leu Gly
                85                  90                  95

Gly Ser Val Ala Gly Leu Leu Ile Ala Ala Ser Pro Val Gln Ile Val
            100                 105                 110

Val Gly Ser Phe
        115

<210> SEQ ID NO 21
<211> LENGTH: 9
<212> TYPE: PRT
<213> ORGANISM: artificial sequence
<220> FEATURE:
<221> NAME/KEY: misc_feature
<222> LOCATION: (1)..(3)
<223> OTHER INFORMATION: First Xaa can be any naturally occurring
      amino acid, 2nd Xaa is R or K, the 3rd Xaa is P, R or K
<220> FEATURE:
<221> NAME/KEY: misc_feature
<222> LOCATION: (8)..(8)
<223> OTHER INFORMATION: Fourth Xaa is P or R
<220> FEATURE:
<223> OTHER INFORMATION: G1945 subclade At-hook domain (G1945 is from
      A. thaliana)
```

-continued

```
<400> SEQUENCE: 21

Xaa Xaa Xaa Arg Gly Arg Pro Xaa Gly
1               5

<210> SEQ ID NO 22
<211> LENGTH: 112
<212> TYPE: PRT
<213> ORGANISM: artificial sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(6)
<223> OTHER INFORMATION: Xaa can be any naturally occurring amino acid
      except 3rd Xaa (5) is I or V and 4th Xaa (6) is L or I
<220> FEATURE:
<221> NAME/KEY: misc_feature
<222> LOCATION: (8)..(10)
<223> OTHER INFORMATION: Xaa can be any naturally occurring amino acid,
      except 5th Xaa (8) is V or I, 7th Xaa (10) is S, A or G
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (15)..(20)
<223> OTHER INFORMATION: Xaa can be any naturally occurring amino acid
      except 10th Xaa (16) is E or Q, 11th Xaa (17) is A or T, 12th Xaa
      (18) is I, L or V
<220> FEATURE:
<221> NAME/KEY: misc_feature
<222> LOCATION: (22)..(27)
<223> OTHER INFORMATION: Xaa can be any naturally occurring amino acid
      except 15th Xaa (22) is C or S, 18th Xaa (25) is K or R, 20th Xaa
      (27) is I, M or L
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Twenty-second Xaa (33) is S, T or A
<220> FEATURE:
<221> NAME/KEY: misc_feature
<222> LOCATION: (35)..(35)
<223> OTHER INFORMATION: Twenty-third Xaa (35) is S or T
<220> FEATURE:
<221> NAME/KEY: misc_feature
<222> LOCATION: (37)..(37)
<223> OTHER INFORMATION: Twenty-fourth  Xaa (37) is S, T or A
<220> FEATURE:
<221> NAME/KEY: misc_feature
<222> LOCATION: (40)..(42)
<223> OTHER INFORMATION: Twenty-fifth Xaa (40) is N or D, 26th Xaa (41)
      is V or I, 27th Xaa (42) is T or S
<220> FEATURE:
<221> NAME/KEY: misc_feature
<222> LOCATION: (45)..(45)
<223> OTHER INFORMATION: Twenty-eighth Xaa (45) is Q or H
<220> FEATURE:
<221> NAME/KEY: misc_feature
<222> LOCATION: (48)..(50)
<223> OTHER INFORMATION: Xaa can be any naturally occurring amino acid
      except 29th Xaa (48) is 1 or 2 residues, 30th Xaa (49) is A, T or
      V
<220> FEATURE:
<221> NAME/KEY: misc_feature
<222> LOCATION: (52)..(56)
<223> OTHER INFORMATION: Xaa can be any naturally occurring amino acid
      except 32nd Xaa (52) is S or T, 33rd Xaa (53) is T or A, 34th Xaa
      (54) is 0 to 3 residues, 35th Xaa (55) is I or V, 36th Xaa(56) is
      T or V
<220> FEATURE:
```

```
<221> NAME/KEY: misc_feature
<222> LOCATION: (60)..(63)
<223> OTHER INFORMATION: Thirty seventh Xaa (60) is R or K, 38th Xaa
      (61) is F or Y, 39th Xaa (62) is D or E, 40th Xaa (63) is L or I
<220> FEATURE:
<221> NAME/KEY: misc_feature
<222> LOCATION: (66)..(67)
<223> OTHER INFORMATION: Forty-first Xaa (66) is V, I or L, 42nd Xaa
      (67) is S or T
<220> FEATURE:
<221> NAME/KEY: misc_feature
<222> LOCATION: (71)..(71)
<223> OTHER INFORMATION: Forty-third Xaa (71) is L or M
<220> FEATURE:
<221> NAME/KEY: misc_feature
<222> LOCATION: (73)..(76)
<223> OTHER INFORMATION: Forty-fourth Xaa (73) is 11 to 16 residues,
      45th Xaa (74) is F or L, 46th Xaa (75) is S, A or T, 47th Xaa
      (76) is V or I
<220> FEATURE:
<221> NAME/KEY: misc_feature
<222> LOCATION: (82)..(82)
<223> OTHER INFORMATION: Forty-eighth (82) Xaa is Q or H
<220> FEATURE:
<221> NAME/KEY: misc_feature
<222> LOCATION: (84)..(86)
<223> OTHER INFORMATION: Forty-ninth Xaa (84) is Q or K, 50th Xaa (85)
      is I or V, 51th Xaa (86) is I or V
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (91)..(91)
<223> OTHER INFORMATION: Fifty-third Xaa (91) is A or V
<220> FEATURE:
<221> NAME/KEY: misc_feature
<222> LOCATION: (93)..(93)
<223> OTHER INFORMATION: Xaa can be any naturally occurring amino acid
<220> FEATURE:
<221> NAME/KEY: misc_feature
<222> LOCATION: (95)..(98)
<223> OTHER INFORMATION: Xaa can be any naturally occurring amino acid
      except 56th Xaa (96) is A or S, 57th Xaa (97) is A or V
<220> FEATURE:
<221> NAME/KEY: misc_feature
<222> LOCATION: (101)..(103)
<223> OTHER INFORMATION: Xaa can be any naturally occurring amino acid
      except 61st Xaa (103) is I, V or M
<220> FEATURE:
<221> NAME/KEY: misc_feature
<222> LOCATION: (105)..(106)
<223> OTHER INFORMATION: 62nd Xaa (105) is A or T, 63rd Xaa (106) is S,
      T or A
<220> FEATURE:
<221> NAME/KEY: misc_feature
<222> LOCATION: (108)..(108)
<223> OTHER INFORMATION: Xaa can be any naturally occurring amino acid
<220> FEATURE:
<221> NAME/KEY: misc_feature
<222> LOCATION: (111)..(112)
<223> OTHER INFORMATION: Sixty-fifth Xaa (111) is S, A or T, 66th Xaa
      (112) is Y or F
<220> FEATURE:
<223> OTHER INFORMATION: consensus G1945 subclade DUF296 domain (G1945
      is from A. thaliana)

<400> SEQUENCE: 22

Met Xaa Pro Xaa Xaa Xaa Glu Xaa Xaa Xaa Gly Xaa Asp Val Xaa Xaa
1               5                   10                  15

Xaa Xaa Xaa Xaa Phe Xaa Xaa Xaa Xaa Xaa Xaa Gly Xaa Cys Val Leu
                20                  25                  30

Xaa Gly Xaa Gly Xaa Val Ala Xaa Xaa Xaa Leu Arg Xaa Pro Ser Xaa
            35                  40                  45

Xaa Xaa Gly Xaa Xaa Xaa Xaa Xaa Phe His Gly Xaa Xaa Xaa Xaa Leu
```

```
                    50                  55                  60
Ser Xaa Xaa Ala Thr Phe Xaa Pro Xaa Xaa Xaa Xaa Ser Leu Ala Gly
 65                  70                  75                  80

Pro Xaa Gly Xaa Xaa Xaa Gly Gly Xaa Val Xaa Gly Xaa Leu Xaa Xaa
                 85                  90                  95

Xaa Xaa Thr Val Xaa Xaa Xaa Ala Xaa Xaa Phe Xaa Asn Pro Xaa Xaa
            100                 105                 110

<210> SEQ ID NO 23
<211> LENGTH: 9
<212> TYPE: PRT
<213> ORGANISM: artificial sequence
<220> FEATURE:
<221> NAME/KEY: misc_feature
<222> LOCATION: (3)..(4)
<223> OTHER INFORMATION: First Xaa is V,I or L, 2nd Xaa is S or T
<220> FEATURE:
<221> NAME/KEY: misc_feature
<222> LOCATION: (8)..(8)
<223> OTHER INFORMATION: Third Xaa is L or M
<220> FEATURE:
<223> OTHER INFORMATION: conserved subsequence in G1945 subclade
      DUF296 domain (G1945 is from A. thaliana)

<400> SEQUENCE: 23

Leu Ser Xaa Xaa Ala Thr Phe Xaa Pro
1               5

<210> SEQ ID NO 24
<211> LENGTH: 7
<212> TYPE: PRT
<213> ORGANISM: artificial sequence
<220> FEATURE:
<221> NAME/KEY: misc_feature
<222> LOCATION: (6)..(6)
<223> OTHER INFORMATION: Xaa is Q or H
<220> FEATURE:
<223> OTHER INFORMATION: conserved subsequence in G1945 subclade
      DUF296 domain (G1945 is from A. thaliana)

<400> SEQUENCE: 24

Ser Leu Ala Gly Pro Xaa Gly
1               5

<210> SEQ ID NO 25
<211> LENGTH: 574
<212> TYPE: DNA
<213> ORGANISM: cauliflower mosaic virus
<220> FEATURE:
<223> OTHER INFORMATION: Cauliflower Mosaic 35S promoter

<400> SEQUENCE: 25
gcggattcca ttgcccagct atctgtcact ttattgtgaa gatagtgaaa aagaaggtgg      60
ctcctacaaa tgccatcatt gcgataaagg aaaggccatc gttgaagatg cctctgccga    120
cagtggtccc aaagatggac ccccacccac gaggagcatc gtggaaaaag aagacgttcc    180
aaccacgtct tcaaagcaag tggattgatg tgatggtccg attgagactt ttcaacaaag    240
ggtaatatcc ggaaacctcc tcggattcca ttgcccagct atctgtcact ttattgtgaa    300
gatagtggaa aaggaaggtg gctcctacaa atgccatcat tgcgataaag gaaaggccat    360
cgttgaagat gcctctgccg acagtggtcc caaagatgga cccccaccca cgaggagcat    420
cgtggaaaaa gaagacgttc caaccacgtc ttcaaagcaa gtggattgat gtgatatctc    480
cactgacgta aggatgacg cacaatccca ctatccttcg caagaccctt cctctatata    540
aggaagttca tttcatttgg agaggacacg ctga                                574
```

<210> SEQ ID NO 26
<211> LENGTH: 4276
<212> TYPE: DNA
<213> ORGANISM: artificial sequence
<220> FEATURE:
<223> OTHER INFORMATION: P6506 driver construct (CaMV 35S::LexA-GAL4TA)

<400> SEQUENCE: 26

```
catgcctgca ggtccccaga ttagcctttt caatttcaga agaatgcta acccacagat      60
ggttagagag gcttacgcag caggtctcat caagacgatc tacccgagca ataatctcca    120
ggaaatcaaa taccttccca agaaggttaa agatgcagtc aaaagattca ggactaactg    180
catcaagaac acagagaaag atatatttct caagatcaga agtactattc cagtatggac    240
gattcaaggc ttgcttcaca aaccaaggca agtaatagag attggagtct ctaaaaaggt    300
agttcccact gaatcaaagg ccatggagtc aaagattcaa atagaggacc taacagaact    360
cgccgtaaag actggcgaac agttcataca gagtctctta cgactcaatg caagaagaa    420
aatcttcgtc aacatggtgg agcacgacac acttgtctac tccaaaaata tcaaagatac    480
agtctcagaa gaccaaaggg caattgagac ttttcaacaa agggtaatat ccggaaacct    540
cctcggattc cattgcccag ctatctgtca ctttattgtg aagatagtgg aaaaggaagg    600
tggctcctac aaatgccatc attgcgataa aggaaaggcc atcgttgaag atgcctctgc    660
cgacagtggt cccaaagatg accccccacc cacgaggagc atcgtggaaa agaagacgt    720
tccaaccacg tcttcaaagc aagtggattg atgtgatatc tccactgacg taagggatga    780
cgcacaatcc cactatcctt cggcggccgc aagacccttc ctctatataa ggaagttcat    840
ttcatttgga gaggacacgc tcgagtataa gagctcattt ttacaacaat taccaacaac    900
aacaaacaac aaacaacatt acaattacat ttacaattac catggaagcg ttaacggcca    960
ggcaacaaga ggtgtttgat ctcatccgtg atcacatcag ccagacaggt atgccgccga   1020
cgcgtgcgga aatcgcgcag cgtttggggt tccgttcccc aaacgcggct gaagaacatc   1080
tgaaggcgct ggcacgcaaa ggcgttattg aaattgtttc cggcgcatca cgcgggattc   1140
gtctgttgca ggaagaggaa gagggttgc cgctggtagg tcgtgtggct gccggtgaac   1200
cacttctggc gcaacagcat attgaaggtc attatcaggt cgatccttcc ttattcaagc   1260
cgaatgctga tttcctgctg cgcgtcagcg ggatgtcgat gaaagatatc ggcattatgg   1320
atggtgactt gctggcagtg cataaaactc aggatgtacg taacggtcag gtcgttgtcg   1380
cacgtattga tgacgaagtt accgttaagc gcctgaaaaa cagggcaat aaagtcgaac   1440
tgttgccaga aaatagcgag tttaaaccaa ttgtcgtaga tcttcgtcag cagagcttca   1500
ccattgaagg ctggcggtt ggggttattc gcaacggcga ctggctggaa ttccccaatt   1560
ttaatcaaag tgggaatatt gctgatagct cattgtcctt cactttcact aacagtagca   1620
acggtccgaa cctcataaca actcaaacaa attctcaagc gctttcacaa ccaattgcct   1680
cctctaacgt tcatgataac ttcatgaata atgaaatcac ggctagtaaa attgatgatg   1740
gtaataattc aaaaccactg tcacctggtt ggacggacca aactgcgtat aacgcgtttg   1800
gaatcactac agggatgttt aataccacta caatggatga tgtatataac tatctattcg   1860
atgatgaaga taccccacca aacccaaaaa aagagtagct agagctttcg ttcgtatcat   1920
cggtttcgac aacgttcgtc aagttcaatg catcagtttc attgcgcaca caccagaatc   1980
ctactgagtt tgagtattat ggcattggga aaactgtttt tcttgtacca tttgttgtgc   2040
```

-continued

```
ttgtaattta ctgtgttttt tattcggttt tcgctatcga actgtgaaat ggaaatggat    2100
ggagaagagt taatgaatga tatggtcctt ttgttcattc tcaaattaat attatttgtt    2160
ttttctctta tttgttgtgt gttgaatttg aaattataag agatatgcaa acattttgtt    2220
ttgagtaaaa atgtgtcaaa tcgtggcctc taatgaccga agttaatatg aggagtaaaa    2280
cacttgtagt tgtaccatta tgcttattca ctaggcaaca aatatatttt cagacctaga    2340
aaagctgcaa atgttactga atacaagtat gtcctcttgt gttttagaca tttatgaact    2400
ttcctttatg taattttcca gaatccttgt cagattctaa tcattgcttt ataattatag    2460
ttatactcat ggatttgtag ttgagtatga aaatatttttt taatgcattt tatgacttgc    2520
caattgattg acaacatgca tcaatctaga acatatccat atctaatctt acctcgactg    2580
ctgtatataa aaccagtggt tatatgtcca gtactgctgt atataaaacc agtggttata    2640
tgtacagtac gtcgatcgat cgacgactgc tgtatataaa accagtggtt atatgtacag    2700
tactgctgta tataaaacca gtggttatat gtacagtacg tcgaggggat gatcaagacc    2760
cttcctctat ataaggaagt tcatttcatt tggagaggac acgctcgagt ataagagctc    2820
atttttacaa caattaccaa caacaacaaa caacaaacaa cattacaatt acatttacaa    2880
ttaccatggt gagcaagggc gaggagctgt tcaccggggt ggtgcccatc ctggtcgagc    2940
tggacggcga cgtaaacggc cacaagttca gcgtgtccgg cgagggcgag ggcgatgcca    3000
cctacggcaa gctgaccctg aagttcatct gcaccaccgg caagctgccc gtgccctggc    3060
ccaccctcgt gaccaccctg acctacggcg tgcagtgctt cagccgctac cccgaccaca    3120
tgaagcagca cgacttcttc aagtccgcca tgcccgaagg ctacgtccag gagcgcacca    3180
tcttcttcaa ggacgacggc aactacaaga cccgcgccga ggtgaagttc gagggcgaca    3240
ccctggtgaa ccgcatcgag ctgaagggca tcgacttcaa ggaggacggc aacatcctgg    3300
ggcacaagct ggagtacaac tacaacagcc acaacgtcta tatcatggcc gacaagcaga    3360
agaacggcat caaggtgaac ttcaagatcc gccacaacat cgaggacggc agcgtgcagc    3420
tcgccgacca ctaccagcag aacacccccc tcggcgacgg ccccgtgctg ctgcccgaca    3480
accactacct gagcacccag tccgccctga gcaaagaccc caacgagaag cgcgatcaca    3540
tggtcctgct ggagttcgtg accgccgccg ggatcactct cggcatggac gagctgtaca    3600
agtccggagg gatcctctag ctagagcttt cgttcgtatc atcggtttcg acaacgttcg    3660
tcaagttcaa tgcatcagtt tcattgcgca cacaccagaa tcctactgag tttgagtatt    3720
atggcattgg gaaaactgtt tttcttgtac catttgttgt gcttgtaatt tactgtgttt    3780
tttattcggt tttcgctatc gaactgtgaa atggaaatgg atggagaaga gttaatgaat    3840
gatatggtcc ttttgttcat tctcaaatta atattatttg ttttttctct tatttgttgt    3900
gtgttgaatt tgaaattata agagatatgc aaacattttg ttttgagtaa aaatgtgtca    3960
aatcgtggcc tctaatgacc gaagttaata tgaggagtaa aacacttgta gttgtaccat    4020
tatgcttatt cactaggcaa caaatatatt ttcagaccta gaaaagctgc aaatgttact    4080
gaatacaagt atgtcctctt gtgttttaga catttatgaa ctttccttta tgtaattttc    4140
cagaatcctt gtcagattct aatcattgct ttataattat agttatactc atggatttgt    4200
agttgagtat gaaaatatttt tttaatgcat tttatgactt gccaattgat tgacaacatg    4260
catcaatcga cctgca                                                   4276
```

<210> SEQ ID NO 27
<211> LENGTH: 1053
<212> TYPE: DNA

<213> ORGANISM: artificial sequence
<220> FEATURE:
<223> OTHER INFORMATION: P2085 direct promoter fusion, carries G1945
      (for producing 35S::G1945) (G1945 is from A. thaliana)

<400> SEQUENCE: 27

```
ctttatacac cataccattt cccaaaggga tttacgaaaa gtccctctcc tctatcatct      60
ctttattcac cccataccaa caacctctac atcttcttct tcttcttcct cctcttttat    120
tttcttttta aatcatttac acaaaaatcc aaagacaaat ctgaaatctc taataaacaa    180
atccataaaa taagaaaaac aaagatgaaa ggtgaataca gagagcaaaa gagtaacgaa    240
atgttttcca agcttcctca tcatcaacaa caacagcaac aacaacaaca acaacactct    300
cttacctctc acttccacct ctcctccacc gtaaccccca ccgtcgatga ctcctccatc    360
gaagtggtcc gacgtccacg tggcagacca ccaggttcca aaaacaaacc taaaccaccc    420
gtcttcgtca cacgtgacac cgaccctcct atgagtcctt acatcctcga agttccttca    480
ggaaacgacg tcgtcgaagc catcaaccgt ttctgccgcc gtaaatccat cggagtctgc    540
gtccttagtg gctctggctc tgtagctaac gtcactttac gtcagccatc accggcagct    600
cttggctcta ccataacttt ccatggaaag tttgatctcc tctccgtctc cgcaacgttt    660
ctccctcctc cgcctcgtac ttccttgtct cctcccgttt ctaacttctt caccgtctct    720
ctcgctggac tcaaggaca aatcatcgga gggttcgtcg ctggtccact tatttcggca     780
ggaacagttt acgtcatcgc cgcaagtttc aacaacccctt cttatcaccg gttaccggcg   840
gaagaagagc aaaaacactc ggcggggaca ggggaaagag agggacaatc tccgccggtc    900
tctggtggcg gtgaagagtc aggacagatg gcgggaagtg gaggagagtc gtgtgggta    960
tcaatgtaca gttgccacat gggtggctct gatgttattt gggcccctac agccagagct   1020
ccaccgccat actaaccaat ccttctttca caa                                 1053
```

<210> SEQ ID NO 28
<211> LENGTH: 845
<212> TYPE: DNA
<213> ORGANISM: artificial sequence
<220> FEATURE:
<223> OTHER INFORMATION: P28914 construct carries G1945 (for producing
      opLexA::G1945) (G1945 is from A. thaliana)

<400> SEQUENCE: 28

```
ggtaccatga aggtgaata cagagagcaa aagagtaacg aaatgttttc caagcttcct      60
catcatcaac aacaacagca acaacaacaa caacaacact ctcttacctc tcacttccac    120
ctctcctcca ccgtaacccc caccgtcgat gactcctcca tcgaagtggt ccgacgtcca    180
cgtggcagac caccaggttc caaaaacaaa cctaaaccac ccgtcttcgt cacacgtgac    240
accgaccctc ctatgagtcc ttacatcctc gaagttcctt caggaaacga cgtcgtcgaa    300
gccatcaacc gttctgccg ccgtaaatcc atcggagtct gcgtccttag tggctctggc     360
tctgtagcta acgtcacttt acgtcagcca tcaccggcag ctcttggctc taccataact    420
ttccatggaa agtttgatct cctctccgtc tccgcaacgt ttctccctcc tccgcctcgt    480
acttccttgt ctcctcccgt ttctaacttc ttcaccgtct ctctcgctgg acctcaagga    540
caaatcatcg gagggttcgt cgctggtcca cttatttcgg caggaacagt ttacgtcatc    600
gccgcaagtt tcaacaaccc cttcttatcac cggttaccgg cggaagaaga gcaaaaacac   660
tcggcgggga caggggaaag agagggacaa tctccgccgg tctctggtgg cggtgaagag    720
tcaggacaga tggcgggaag tggaggagag tcgtgtgggg tatcaatgta cagttgccac    780
```

```
atgggtggct ctgatgttat ttgggcccct acagccagag ctccaccgcc atactaagcg      840
gccgc                                                                  845

<210> SEQ ID NO 29
<211> LENGTH: 780
<212> TYPE: DNA
<213> ORGANISM: artificial sequence
<220> FEATURE:
<223> OTHER INFORMATION: P1742 direct promoter fusion, carries G2155
      (for producing 35S::G2155)  (G2155 is from A. thaliana)

<400> SEQUENCE: 29
ctcatatata ccaaccaaac ctctctctgc atctttatta acacaaaatt ccaaaagatt       60
aaatgttgtc gaagctccct acacagcgac acttgcacct ctctccctcc tctccctcca     120
tggaaaccgt cgggcgtcca cgtggcagac ctcgaggttc caaaaacaaa cctaaagctc     180
caatctttgt caccattgac cctcctatga gtccttacat cctcgaagtg ccatccggaa     240
acgatgtcgt tgaagcccta aaccgtttct gccgcgtaa agccatcggc ttttgcgtcc      300
tcagtggctc aggctccgtt gctgatgtca ctttgcgtca gccttctccg gcagctcctg     360
gctcaaccat tactttccac ggaaagttcg atcttctctc tgtctccgcc actttcctcc     420
ctcctctacc tcctacctcc ttgtcccctc ccgtctccaa tttcttcacc gtctctctcg     480
ccggacctca ggggaaagtc atcggtggat tcgtcgctgg tcctcgtt gccgccggaa       540 ctgtttactt cgtcgccact agtttcaaga acccttccta tcaccggtta cctgctacgg     600
aggaagagca agaaactcg gcggaagggg aagaggaggg acaatcgccg ccggtctctg      660
gaggtggtgg agagtcgatg tacgtgggtg gctctgatgt catttgggat cccaacgcca     720
aagctccatc gccgtactga ccacaaatcc atctcgttca aactagggtt tcttcttctt     780

<210> SEQ ID NO 30
<211> LENGTH: 692
<212> TYPE: DNA
<213> ORGANISM: artificial sequence
<220> FEATURE:
<223> OTHER INFORMATION: P28915 construct carries G2155 (for producing
      opLexA::G2155)  (G2155 is from A. thaliana)

<400> SEQUENCE: 30
ggtaccatgt tgtcgaagct ccctacacag cgacacttgc acctctctcc ctcctctccc      60
tccatggaaa ccgtcgggcg tccacgtggc agacctcgag gttccaaaaa caaacctaaa     120
gctccaatct ttgtcaccat tgaccctcct atgagtcctt acatcctcga agtgccatcc     180
ggaaacgatg tcgttgaagc cctaaaccgt ttctgccgcg gtaaagccat cggcttttgc     240
gtcctcagtg gctcaggctc cgttgctgat gtcactttgc gtcagccttc tccggcagct     300
cctggctcaa ccattacttt ccacggaaag ttcgatcttc tctctgtctc cgccactttc     360
ctccctcctc tacctcctac ctccttgtcc cctcccgtct ccaatttctt caccgtctct     420
ctcgccggac ctcaggggaa agtcatcggt ggattcgtcg ctggtcctct cgttgccgcc     480
ggaactgttt acttcgtcgc cactagtttc aagaacccct tcctatcaccg gttacctgct    540 acggaggaag agcaaagaaa ctcggcggaa ggggaagagg agggacaatc gccgccggtc     600
tctggaggtg gtggagagtc gatgtacgtg gtggctctg atgtcatttg ggatcccaac      660
gccaaagctc catcgccgta ctgagcggcc gc                                   692

<210> SEQ ID NO 31
<211> LENGTH: 1064
<212> TYPE: DNA
```

<213> ORGANISM: artificial sequence
<220> FEATURE:
<223> OTHER INFORMATION: P21246 direct promoter fusion, carries G3408
      (for producing 35S::G3408) (G3408 is from O. sativa

<400> SEQUENCE: 31

```
gtggttttgg ttgattgcta ctctgtgcca tgtcgttctg cgagagggac atgaacaagg      60
agagcatgta ccaagaacgg gacgacatgg cggggatacg gttcgcgacg ccgccgctgc     120
ctcagcagca gcagcagcag cagctggtgg agtgcttctc cgacgaggtg gacagccgcg     180
ggagtggcgg cgagatgaag gatgccgtgg ggagcgggag tggcagctg gtcgttgttg      240 gtggcgggga tggggcgagc atcgaggtgg cgaagaagag gaggggagg ccgccggggt      300 ccaagaacaa gccgaagcca cccgtggtga tcacgcggga ggcggagccg gcggcggcga     360
tgcggccgca cgtgatcgag atccccggcg ggcgggacgt cgcggaggcg ctcgcgcggt     420
tctcgagccg tcggaacctc gggatctgcg tgctcgccgg caccggcgcg gtcgccaacg     480
tgtcgctccg ccacccgtca cccggggtcc cgggctcagc tccggctgcg atcgtgttcc     540
acggccggta cgagatcctc tccctgtcgg ccacgttcct gcctccggcc atgtcctccg     600
tggcgcccca ggccgcggtc gccgccgcgg gcctctccat ctcgctcgcc ggcccgcacg     660
gccagatcgt cggcggggcc gtggcaggcc cgctctacgc cgcgaccacc gtcgtggtcg     720
tcgccgccgc cttcaccaac cccaccttcc accgcctccc cgccgacgac gacgcgtcgg     780
tgtccgtctc ggtgtcactc tccggcagcg gcgacgcgga cgaacaccgg ggccaccagc     840
acaaacctga gccgcaagaa ccgcgccaac ttcgacggcc gccaccgcac ctgtcagcag     900
ccgccgccgt ctcagcagca cagccggtgg agccatgcgg cgcgcccatg tacgcctgcc     960
accctcagcc acaggaggtg atgtggccgc cgccggctcg tacgccgcac ccgccgccgc    1020
cgccgccgta ctaatccgac cgaattggta cgccattgcc acat                     1064
```

<210> SEQ ID NO 32
<211> LENGTH: 827
<212> TYPE: DNA
<213> ORGANISM: artificial sequence
<220> FEATURE:
<223> OTHER INFORMATION: pMON93672, showing promoter that drives
      expression in seed (for producing pGmSphas1::G3936 direct
      promoter fusion) (G3936 is from G. max)

<400> SEQUENCE: 32

```
ggcaaaaaca tttaatacgt attatttaag aaaaaaatat gtaataatat atttatattt      60
taatatctat tcttatgtat tttttaaaaa tctattatat attgatcaac taaaatattt     120
ttatatctac acttattttg cattttatc aattttcttg cgtttttgg catatttaat       180 aatgactatt ctttaataat caatcattat tcttacatgg tacatattgt tggaaccata     240
tgaagtgtcc attgcatttg actatgtgga tagtgttttg atccaggcct ccatttgccg     300
cttattaatt aatttggtaa cagtccgtac taatcagtta cttatccttc ctccatcata     360
attaatcttg gtagtctcga atgccacaac actgactagt ctcttggatc ataagaaaaa     420
gccaaggaac aaaagaagac aaaacacaat gagagtatcc tttgcatagc aatgtctaag     480
ttcataaaat tcaaacaaaa acgcaatcac acacagtgga catcacttat ccactagctg     540
atcaggatcg ccgcgtcaag aaaaaaaaac tggaccccaa aagccatgca caacaacacg     600
tactcacaaa ggtgtcaatc gagcagccca aacattcac caactcaacc catcatgagc     660
ccacacattt gttgtttcta acccaacctc aaactcgtat tctcttccgc cacctcattt     720
ttgtttattt caacacccgt caaactgcat gccacccegt ggccaaatgt ccatgcatgt     780
```

```
taacaagacc tatgactata aatatctgca atctcggccc aggtttt        827
```

<210> SEQ ID NO 33
<211> LENGTH: 1538
<212> TYPE: DNA
<213> ORGANISM: artificial sequence
<220> FEATURE:
<223> OTHER INFORMATION: P1417 direct promoter fusion, carries G597
      (for producing 35S::G597) (G597 is from A. thaliana)

<400> SEQUENCE: 33

```
aaaattctcc tgtaaaattt aatattataa aagtggtttc tttttcattt atgtttatat     60
aattttcatc tttaatctta aattctggta accttaatgc gcgatccgct tttctaaagt    120
tttgtgagag agaagagatc taaaaaaatc cacaattttg ttcaaatctt ggagttaaat    180
gctgaatttt aggccttgtt gcttagattt atggcttaaa gtttcaaact tttcattgga    240
tatgtgagaa gaaaatgtca ggatctgaga cgggtttaat ggcggcgacc agagaatcaa    300
tgcaatttac aatggctctc caccagcagc agcaacacag tcaagctcaa cctcagcagt    360
ctcagaacag gccattgtca ttcggtggag acgacggaac tgctctttac aagcagccga    420
tgagatcagt atcaccaccg cagcagtacc aacccaactc agctggtgag aattctgtct    480
tgaacatgaa cttgcccgga ggtgagtctg gaggcatgac tggaactgga agtgagccag    540
tgaaaaagag gagaggtaga ccgaggaaat atgggcctga tagtggtgaa atgtcacttg    600
gtttgaatcc tggagctcct tctttcactg tcagccaacc tagtagcggc ggcgatggag    660
gagagaagaa gagaggaaga cctcctggtt cttctagcaa aaggctcaag cttcaagctt    720
taggctcgac tggaatcgga tttacgcctc atgtacttac cgtgctggct ggagaggatg    780
tatcatccaa gataatggcg ttaactcata atggaccccg tgctgtgtgt gtcttgtctg    840
caaatggagc catctccaat gtgactctcc gccagtctgc cacatccggt ggaactgtta    900
catatgaggg gagatttgag attctgtctt tatcgggatc tttccatttg ctggagaaca    960
atggtcaaag aagcaggacg ggaggtctaa gcgtgtcatt atcaagtccg gatggtaatg   1020
tcctcggtgg cagtgtagct ggtcttctta tagcagcatc acctgttcag attgttgttg   1080
ggagtttctt accagacgga gaaaagaac caaaacagca tgtgggacaa atgggactgt   1140
cgtcacccgt attaccgcgt gtggccccaa cgcaggtgct gatgactcca agtagcccac   1200
aatctcgagg cacaatgagt gagtcatctt gtggaggagg acatggaagc cctattcatc   1260
agagcactgg aggaccttac aataacacca ttaacatgcc ctggaagtag ccaagtgatc   1320
tgtgtcggct taaaccaac aacttcccgt tattagagtg atttatttct acatttggtt   1380
tagactttct agttctgatg gttatttcta cagttggttt agactttcta gttctgttca   1440
gacaaaagga gtttgataaa ttgaccgacc tattttgtgt gtttgaggta ctttcagaac   1500
cataggtgtt cagaaattag aatgttctgt ttaaaaaa                           1538
```

<210> SEQ ID NO 34
<211> LENGTH: 305
<212> TYPE: PRT
<213> ORGANISM: Oryza sativa
<220> FEATURE:
<223> OTHER INFORMATION: G3406 polypeptide

<400> SEQUENCE: 34

```
Met Ala Gly Leu Asp Leu Gly Thr Ala Ala Thr Arg Tyr Val His Gln
1               5                   10                  15

Leu His His Leu His Pro Asp Leu Gln Leu Gln His Ser Tyr Ala Lys
```

```
                    20                  25                  30
Gln His Glu Pro Ser Asp Asp Pro Asn Gly Ser Gly Gly Gly
            35                  40                  45

Asn Ser Asn Gly Gly Pro Tyr Gly Asp His Asp Gly Gly Ser Ser Ser
 50                          55                  60

Ser Gly Pro Ala Thr Asp Gly Ala Val Gly Gly Pro Gly Asp Val Val
 65                  70                  75                  80

Ala Arg Arg Pro Arg Gly Arg Pro Pro Gly Ser Lys Asn Lys Pro Lys
                    85                  90                  95

Pro Pro Val Ile Ile Thr Arg Glu Ser Ala Asn Thr Leu Arg Ala His
                100                 105                 110

Ile Leu Glu Val Gly Ser Gly Cys Asp Val Phe Glu Cys Val Ser Thr
            115                 120                 125

Tyr Ala Arg Arg Gln Arg Gly Val Cys Val Leu Ser Gly Ser Gly
            130                 135                 140

Val Val Thr Asn Val Thr Leu Arg Gln Pro Ser Ala Pro Ala Gly Ala
145                 150                 155                 160

Val Val Ser Leu His Gly Arg Phe Glu Ile Leu Ser Leu Ser Gly Ser
                165                 170                 175

Phe Leu Pro Pro Pro Ala Pro Pro Gly Ala Thr Ser Leu Thr Ile Phe
                180                 185                 190

Leu Ala Gly Gly Gln Gly Gln Val Val Gly Gly Asn Val Val Gly Ala
            195                 200                 205

Leu Tyr Ala Ala Gly Pro Val Ile Val Ile Ala Ala Ser Phe Ala Asn
            210                 215                 220

Val Ala Tyr Glu Arg Leu Pro Leu Glu Glu Glu Ala Pro Pro
225                 230                 235                 240

Gln Ala Gly Leu Gln Met Gln Pro Gly Gly Ala Asp Ala Gly
                    245                 250                 255

Gly Met Gly Gly Ala Phe Pro Pro Asp Pro Ser Ala Ala Gly Leu Pro
                260                 265                 270

Phe Phe Asn Leu Pro Leu Asn Asn Met Pro Gly Gly Gly Ser Gln
            275                 280                 285

Leu Pro Pro Gly Ala Asp Gly His Gly Trp Ala Gly Ala Arg Pro Pro
            290                 295                 300

Phe
305

<210> SEQ ID NO 35
<211> LENGTH: 302
<212> TYPE: PRT
<213> ORGANISM: Glycine max
<220> FEATURE:
<223> OTHER INFORMATION: G3462 polypeptide

<400> SEQUENCE: 35

Met Ala Asn Arg Trp Trp Ala Gly Asn Val Gly Met Ile Arg Glu Gln
 1               5                  10                  15

Glu Leu Met Glu Asn Ser Asn Asn Asn Asn Asn Asn Asn Asn Ala Thr
                20                  25                  30

Thr Thr Thr Pro Thr Thr Arg Ser Asn Ser Thr Asn Ala Asn Thr
            35                  40                  45

Asn Thr Asn Thr Thr Glu Glu Glu Val Ser Arg Asp Asn Gly Glu Asp
 50                  55                  60

Gln Asn Gln Asn Leu Gly Ser His Glu Gly Ser Glu Pro Gly Ser Ser
 65                  70                  75                  80
```

```
Gly Arg Arg Pro Arg Gly Arg Pro Ala Gly Ser Lys Asn Lys Pro Lys
                85                  90                  95

Pro Pro Ile Val Ile Ile Phe Leu Ser Pro Asn Ala Leu Arg Ser His
            100                 105                 110

Val Leu Glu Ile Ala Ser Gly Arg Asp Val Ala Glu Ser Ile Ala Ala
        115                 120                 125

Phe Ala Asn Arg Arg His Arg Gly Val Ser Val Leu Ser Gly Ser Gly
130                 135                 140

Ile Val Ala Asn Val Thr Leu Arg Gln Pro Ala Ala Pro Ala Gly Val
145                 150                 155                 160

Ile Thr Leu His Gly Arg Phe Glu Ile Leu Ser Leu Ser Gly Ala Phe
                165                 170                 175

Leu Pro Ser Pro Ser Pro Ser Gly Ala Thr Gly Leu Thr Val Tyr Leu
            180                 185                 190

Ala Gly Gly Gln Gly Gln Val Val Gly Gly Asn Val Ala Gly Ser Leu
        195                 200                 205

Val Ala Ser Gly Pro Val Met Val Ile Ala Ala Thr Phe Ala Asn Ala
210                 215                 220

Thr Tyr Glu Arg Leu Pro Leu Glu Asp Asp Gln Gly Glu Glu Glu Met
225                 230                 235                 240

Gln Val Gln Gln Gln Gln Gln Gln Gln Gln Gln Gln Gln Gln Gln Gln
                245                 250                 255

Gln Gln Gln Gln Ser Gln Gly Leu Gly Glu Gln Val Ser Met Pro Met
            260                 265                 270

Tyr Asn Leu Pro Pro Asn Leu Leu His Asn Gly Gln Asn Met Pro His
        275                 280                 285

Asp Val Phe Trp Gly Ala Pro Pro Arg Pro Pro Ser Phe
290                 295                 300

<210> SEQ ID NO 36
<211> LENGTH: 270
<212> TYPE: PRT
<213> ORGANISM: Glycine max
<220> FEATURE:
<223> OTHER INFORMATION: G3458 polypeptide

<400> SEQUENCE: 36

Met Ala Gly Ile Asp Leu Gly Ser Ala Ser His Phe Val His His Arg
1               5                   10                  15

Leu Glu Arg Pro Asp Leu Glu Asp Asp Glu Asn Gln Gln Asp Gln Asp
            20                  25                  30

Asn Asn Leu Asn Asn His Glu Gly Leu Asp Leu Val Thr Pro Asn Ser
        35                  40                  45

Gly Pro Gly Asp Val Val Gly Arg Arg Pro Arg Gly Arg Pro Pro Gly
    50                  55                  60

Ser Lys Asn Lys Pro Lys Pro Val Ile Ile Thr Arg Glu Ser Ala
65                  70                  75                  80

Asn Thr Leu Arg Ala His Ile Leu Glu Val Ser Ser Gly Cys Asp Val
                85                  90                  95

Phe Glu Ser Val Ala Thr Tyr Ala Arg Lys Arg Gln Arg Gly Ile Cys
            100                 105                 110

Val Leu Ser Gly Ser Gly Thr Val Thr Asn Val Thr Leu Arg Gln Pro
        115                 120                 125

Ala Ala Ala Gly Ala Val Val Thr Leu His Gly Arg Phe Glu Ile Leu
    130                 135                 140
```

```
Ser Leu Ser Gly Ser Phe Leu Pro Pro Ala Pro Pro Gly Ala Thr
145                 150                 155                 160

Ser Leu Thr Val Phe Leu Gly Gly Gln Gly Gln Val Val Gly Gly
            165                 170                 175

Asn Val Val Gly Pro Leu Val Ala Ser Gly Pro Val Ile Val Ile Ala
        180                 185                 190

Ser Ser Phe Thr Asn Val Ala Tyr Glu Arg Leu Pro Leu Asp Glu Asp
            195                 200                 205

Glu Ser Met Gln Met Gln Gln Gly Gln Ser Ser Ala Gly Asp Gly Ser
    210                 215                 220

Gly Asp His Gly Gly Val Ser Asn Asn Ser Phe Pro Asp Pro Ser
225                 230                 235                 240

Ser Gly Leu Pro Phe Phe Asn Leu Pro Leu Asn Met Pro Gln Leu Pro
                245                 250                 255

Val Asp Gly Trp Ala Gly Asn Ser Gly Gly Arg Gln Ser Tyr
            260                 265                 270
```

<210> SEQ ID NO 37
<211> LENGTH: 295
<212> TYPE: PRT
<213> ORGANISM: Glycine max
<220> FEATURE:
<223> OTHER INFORMATION: G3459 polypeptide

<400> SEQUENCE: 37

```
Met Ala Gly Leu Asp Leu Gly Ser Ala Ser Arg Phe Val Gln Asn Leu
1               5                   10                  15

His Arg Pro Asp Leu His Leu Gln Gln Asn Phe Gln Gln His Gln Asp
            20                  25                  30

Gln Gln His Gln Arg Asp Leu Glu Glu Gln Lys Thr Pro Pro Asn His
        35                  40                  45

Arg Met Gly Ala Pro Phe Asp Asp Asp Ser Asp Asp Arg Ser Pro Gly
50                  55                  60

Leu Glu Leu Thr Ser Gly Pro Gly Asp Ile Val Gly Arg Arg Pro Arg
65                  70                  75                  80

Gly Arg Pro Pro Gly Ser Lys Asn Lys Pro Lys Pro Pro Val Ile Ile
                85                  90                  95

Thr Arg Glu Ser Ala Asn Thr Leu Arg Ala His Ile Leu Glu Val Gly
            100                 105                 110

Ser Gly Ser Asp Val Phe Asp Cys Val Thr Ala Tyr Ala Arg Arg Arg
        115                 120                 125

Gln Arg Gly Ile Cys Val Leu Ser Gly Ser Gly Thr Val Thr Asn Val
    130                 135                 140

Ser Leu Arg Gln Pro Ala Ala Ala Gly Ala Val Val Thr Leu His Gly
145                 150                 155                 160

Arg Phe Glu Ile Leu Ser Leu Ser Gly Ser Phe Leu Pro Pro Pro Ala
                165                 170                 175

Pro Pro Gly Ala Thr Ser Leu Thr Ile Tyr Leu Ala Gly Gly Gln Gly
            180                 185                 190

Gln Val Val Gly Gly Asn Val Ile Gly Glu Leu Thr Ala Ala Gly Pro
        195                 200                 205

Val Ile Val Ile Ala Ala Ser Phe Thr Asn Val Ala Tyr Glu Arg Leu
    210                 215                 220

Pro Leu Glu Glu Asp Glu Gln Gln Gln Gln Gln Gln Leu Gln Ile
225                 230                 235                 240

Gln Pro Pro Ala Thr Thr Ser Ser Gln Gly Asn Asn Asn Asn Asn
```

```
                      245                 250                 255
Pro Phe Pro Asp Pro Ser Ser Gly Leu Pro Phe Phe Asn Leu Pro Leu
                260                 265                 270

Asn Met Gln Asn Val Gln Leu Pro Val Glu Gly Trp Ala Val Asn Pro
            275                 280                 285

Ala Ser Arg Pro Gln Pro Phe
        290                 295

<210> SEQ ID NO 38
<211> LENGTH: 276
<212> TYPE: PRT
<213> ORGANISM: Glycine max
<220> FEATURE:
<223> OTHER INFORMATION: G3460 polypeptide

<400> SEQUENCE: 38

Met Ala Gly Leu Asp Leu Gly Ser Ala Ser Arg Phe Val Gln Asn Leu
1               5                   10                  15

His Leu Pro Asp Leu His Leu Gln Gln Asn Tyr Gln Gln Pro Arg His
            20                  25                  30

Lys Arg Asp Ser Glu Glu Gln Glu Thr Pro Pro Asn Pro Gly Thr Ala
        35                  40                  45

Leu Ala Pro Phe Asp Asn Asp Asp Lys Ser Gln Gly Leu Glu Leu
50                  55                  60

Ala Ser Gly Pro Gly Asp Ile Val Gly Arg Arg Pro Arg Gly Arg Pro
65                  70                  75                  80

Ser Gly Ser Lys Asn Lys Pro Lys Pro Val Ile Ile Thr Arg Glu
                85                  90                  95

Ser Ala Asn Thr Leu Arg Ala His Ile Leu Glu Val Gly Ser Gly Ser
            100                 105                 110

Asp Val Phe Asp Cys Val Thr Ala Tyr Ala Arg Arg Gln Arg Gly
        115                 120                 125

Ile Cys Val Leu Ser Gly Ser Gly Thr Val Thr Asn Val Ser Leu Arg
130                 135                 140

Gln Pro Ala Ala Gly Ala Val Val Arg Leu His Gly Arg Phe Glu
145                 150                 155                 160

Ile Leu Ser Leu Ser Gly Ser Phe Leu Pro Pro Ala Pro Pro Gly
            165                 170                 175

Ala Thr Ser Leu Thr Ile Tyr Leu Ala Gly Gly Gln Gly Gln Val Val
        180                 185                 190

Gly Gly Asn Val Val Gly Glu Leu Thr Ala Ala Gly Pro Val Ile Val
            195                 200                 205

Ile Ala Ala Ser Phe Thr Asn Val Ala Tyr Glu Arg Leu Pro Leu Glu
        210                 215                 220

Glu Asp Glu Gln Gln Gln Gln Leu Gln Ile Gln Ser Pro Ala Thr
225                 230                 235                 240

Thr Ser Ser Gln Gly Asn Asn Asn Asn Pro Phe Pro Asp Pro Ser
                245                 250                 255

Ser Gly Leu Pro Phe Phe Asn Leu Pro Leu Asn Met Gln Asn Val Gln
            260                 265                 270

Leu Pro Pro Phe
        275

<210> SEQ ID NO 39
<211> LENGTH: 281
<212> TYPE: PRT
<213> ORGANISM: Arabidopsis thaliana
```

```
<220> FEATURE:
<223> OTHER INFORMATION: G1069 polypeptide

<400> SEQUENCE: 39

Met Ala Asn Pro Trp Trp Thr Asn Gln Ser Gly Leu Ala Gly Met Val
1               5                   10                  15

Asp His Ser Val Ser Ser Gly His His Gln Asn His His Gln Ser
            20                  25                  30

Leu Leu Thr Lys Gly Asp Leu Gly Ile Ala Met Asn Gln Ser Gln Asp
        35                  40                  45

Asn Asp Gln Asp Glu Glu Asp Pro Arg Glu Gly Ala Val Glu Val
    50                  55                  60

Val Asn Arg Arg Pro Arg Gly Arg Pro Gly Ser Lys Asn Lys Pro
65              70                  75                  80

Lys Ala Pro Ile Phe Val Thr Arg Asp Ser Pro Asn Ala Leu Arg Ser
                85                  90                  95

His Val Leu Glu Ile Ser Asp Gly Ser Asp Val Ala Thr Ile Ala
            100                 105                 110

His Phe Ser Arg Arg Arg Gln Arg Gly Val Cys Val Leu Ser Gly Thr
        115                 120                 125

Gly Ser Val Ala Asn Val Thr Leu Arg Gln Ala Ala Pro Gly Gly
    130                 135                 140

Val Val Ser Leu Gln Gly Arg Phe Glu Ile Leu Ser Leu Thr Gly Ala
145                 150                 155                 160

Phe Leu Pro Gly Pro Ser Pro Gly Ser Thr Gly Leu Thr Val Tyr
                165                 170                 175

Leu Ala Gly Val Gln Gly Gln Val Val Gly Ser Val Val Gly Pro
            180                 185                 190

Leu Leu Ala Ile Gly Ser Val Met Val Ile Ala Ala Thr Phe Ser Asn
        195                 200                 205

Ala Thr Tyr Glu Arg Leu Pro Met Glu Glu Glu Asp Gly Gly Gly
    210                 215                 220

Ser Arg Gln Ile His Gly Gly Asp Ser Pro Arg Ile Gly Ser
225             230                 235                 240

Asn Leu Pro Asp Leu Ser Gly Met Ala Gly Pro Gly Tyr Asn Met Pro
                245                 250                 255

Pro His Leu Ile Pro Asn Gly Ala Gly Gln Leu Gly His Glu Pro Tyr
            260                 265                 270

Thr Trp Val His Ala Arg Pro Pro Tyr
        275                 280

<210> SEQ ID NO 40
<211> LENGTH: 289
<212> TYPE: PRT
<213> ORGANISM: Oryza sativa
<220> FEATURE:
<223> OTHER INFORMATION: G3407 polypeptide

<400> SEQUENCE: 40

Met Ala Gly Leu Asp Leu Gly Thr Ser Tyr Leu His His Gln Ser
1               5                   10                  15

Leu His Leu Arg His Asp Asp Gly Ala Gly Ser Asp Asp Gly Gly
            20                  25                  30

His Asp Asp Leu Ser Pro Gly Ser Gly Gly Gly Pro Ser Ser
        35                  40                  45

Thr Ala Gly Gly Ala Gly Ile Gly Gly Gly Glu Val Val Ala Arg Arg
    50                  55                  60
```

```
Pro Arg Gly Arg Pro Pro Gly Ser Lys Asn Lys Pro Lys Pro Pro Val
 65                  70                  75                  80

Ile Ile Thr Arg Glu Ser Ala Asn Ala Leu Arg Ala His Ile Leu Glu
                 85                  90                  95

Val Ala Ala Gly Cys Asp Val Phe Glu Ala Leu Thr Ala Tyr Ala Arg
            100                 105                 110

Arg Arg Gln Arg Gly Val Cys Val Leu Ser Ala Ala Gly Thr Val Ala
        115                 120                 125

Asn Val Thr Leu Arg Gln Pro Gln Ser Ala Gln Pro Gly Pro Ala Ser
    130                 135                 140

Pro Ala Val Ala Thr Leu His Gly Arg Phe Glu Ile Leu Ser Leu Ala
145                 150                 155                 160

Gly Ser Phe Leu Pro Pro Ala Pro Pro Gly Ala Thr Ser Leu Ala
                165                 170                 175

Ala Phe Leu Ala Gly Gly Gln Gly Gln Val Val Gly Ser Val Ala
            180                 185                 190

Gly Ala Leu Ile Ala Ala Gly Pro Val Val Val Ala Ala Ser Phe
        195                 200                 205

Ser Asn Val Ala Tyr Glu Arg Leu Pro Leu Glu Asp Gly Asp Glu Val
    210                 215                 220

Val Pro Pro Ala Pro Ala Gly Ser Asp Gln Gly Gly Gly Ser Gly
225                 230                 235                 240

Gly Met Pro Pro Leu Gly Val Asp Pro Ser Gly Gly Ala Ala Thr Gly
                245                 250                 255

Gly Leu Pro Phe Phe Asn Met Pro Phe Gly Met Pro Pro Met Pro Val
                260                 265                 270

Asp Gly His Ala Gly Trp Pro Gly Ala Gly Val Gly Arg Pro Pro Phe
            275                 280                 285

Ser

<210> SEQ ID NO 41
<211> LENGTH: 310
<212> TYPE: PRT
<213> ORGANISM: Arabidopsis thaliana
<220> FEATURE:
<223> OTHER INFORMATION: G2157 polypeptide

<400> SEQUENCE: 41

Met Ala Asn Pro Trp Trp Val Gly Asn Val Ala Ile Gly Gly Val Glu
 1               5                  10                  15

Ser Pro Val Thr Ser Ser Ala Pro Ser Leu His His Arg Asn Ser Asn
                20                  25                  30

Asn Asn Asn Pro Pro Thr Met Thr Arg Ser Asp Pro Arg Leu Asp His
             35                  40                  45

Asp Phe Thr Thr Asn Asn Ser Gly Ser Pro Asn Thr Gln Thr Gln Ser
     50                  55                  60

Gln Glu Glu Gln Asn Ser Arg Asp Glu Gln Pro Ala Val Glu Pro Gly
 65                  70                  75                  80

Ser Gly Ser Gly Ser Thr Gly Arg Arg Pro Arg Gly Arg Pro Pro Gly
                 85                  90                  95

Ser Lys Asn Lys Pro Lys Ser Pro Val Val Thr Lys Glu Ser Pro
            100                 105                 110

Asn Ser Leu Gln Ser His Val Leu Glu Ile Ala Thr Gly Ala Asp Val
        115                 120                 125

Ala Glu Ser Leu Asn Ala Phe Ala Arg Arg Arg Gly Arg Gly Val Ser
```

```
                130                 135                 140
Val Leu Ser Gly Ser Gly Leu Val Thr Asn Val Thr Leu Arg Gln Pro
145                 150                 155                 160

Ala Ala Ser Gly Gly Val Val Ser Leu Arg Gly Gln Phe Glu Ile Leu
                165                 170                 175

Ser Met Cys Gly Ala Phe Leu Pro Thr Ser Gly Ser Pro Ala Ala Ala
                180                 185                 190

Ala Gly Leu Thr Ile Tyr Leu Ala Gly Ala Gln Gly Gln Val Val Gly
                195                 200                 205

Gly Gly Val Ala Gly Pro Leu Ile Ala Ser Gly Pro Val Ile Val Ile
                210                 215                 220

Ala Ala Thr Phe Cys Asn Ala Thr Tyr Glu Arg Leu Pro Ile Glu Glu
225                 230                 235                 240

Glu Gln Gln Gln Glu Gln Pro Leu Gln Leu Glu Asp Gly Lys Lys Gln
                245                 250                 255

Lys Glu Glu Asn Asp Asp Asn Glu Ser Gly Asn Asn Gly Asn Glu Gly
                260                 265                 270

Ser Met Gln Pro Pro Met Tyr Asn Met Pro Pro Asn Phe Ile Pro Asn
                275                 280                 285

Gly His Gln Met Ala Gln His Asp Val Tyr Trp Gly Pro Pro Pro
                290                 295                 300

Arg Ala Pro Pro Ser Tyr
305                 310

<210> SEQ ID NO 42
<211> LENGTH: 307
<212> TYPE: PRT
<213> ORGANISM: Glycine max
<220> FEATURE:
<223> OTHER INFORMATION: G3457 polypeptide

<400> SEQUENCE: 42

Met Asp Pro Val Ala Ala Gln Gly Arg Pro Leu Pro Pro Pro Phe Leu
1               5                   10                  15

Thr Arg Asp Leu His Leu His Pro His His Gln Phe Gln Pro His His
                20                  25                  30

Asn His Gln Asn Thr Glu Asp Glu Ala Gly Asn Gly Arg Gly Gln Lys
                35                  40                  45

Arg Asp Arg Asp Glu Asn Ala Gly Gly Gly Gly Ala Thr Thr Pro
50                  55                  60

Pro Gln Gly Gly Gly Glu Gly Lys Glu Ser Gly Ser Gly Asp Gly Gly
65                  70                  75                  80

Gly Ser Asp Met Gly Arg Arg Pro Arg Gly Arg Pro Ala Gly Ser Lys
                85                  90                  95

Asn Lys Pro Lys Pro Pro Ile Ile Ile Thr Arg Asp Ser Ala Asn Ala
                100                 105                 110

Leu Arg Ser His Val Met Glu Ile Ala Asn Gly Cys Asp Ile Met Glu
                115                 120                 125

Ser Ile Thr Ala Phe Ala Arg Arg Arg Gln Arg Gly Val Cys Val Leu
                130                 135                 140

Ser Gly Ser Gly Thr Val Thr Asn Val Thr Leu Arg Gln Pro Ala Ser
145                 150                 155                 160

Pro Gly Ala Val Val Thr Leu His Gly Arg Phe Glu Ile Leu Ser Leu
                165                 170                 175

Ser Gly Ser Phe Leu Pro Pro Pro Ala Pro Ala Ala Ser Gly Leu
                180                 185                 190
```

```
Ala Ile Tyr Leu Ala Gly Gly Gln Gly Gln Val Val Gly Gly Ser Val
        195                 200                 205

Val Gly Pro Leu Val Ala Ser Gly Pro Val Val Ile Met Ala Ala Ser
    210                 215                 220

Phe Gly Asn Ala Ala Tyr Glu Arg Leu Pro Leu Glu Glu Glu Glu Thr
225                 230                 235                 240

Pro Val Ala Val Ala Gly Asn Gly Gly Leu Gly Ser Pro Gly Ile Pro
                245                 250                 255

Gly Thr Gln Gln Gln Pro Gln Gln Gln Gln Gln Gln Leu Val Gly
            260                 265                 270

Asp Pro Asn Ser Ser Ser Leu Phe His Gly Met Pro Gln Asn Leu Leu
                275                 280                 285

Asn Ser Val Gln Leu Pro Ala Glu Gly Tyr Trp Gly Gly Ser Ala Arg
            290                 295                 300

Pro Pro Phe
305

<210> SEQ ID NO 43
<211> LENGTH: 322
<212> TYPE: PRT
<213> ORGANISM: Oryza sativa
<220> FEATURE:
<223> OTHER INFORMATION: G3400 polypeptide

<400> SEQUENCE: 43

Met Ala Gly Met Asp Pro Thr Gly Gly Gly Gly Gly Gly Gly Val Ala
1               5                   10                  15

Ala His Tyr Leu His Met Leu Arg Ala Gln Gln His Gln Pro Leu Ser
            20                  25                  30

Pro Ala Gly Asp Val Lys Ala Glu Arg Ser Met Leu Ser Pro Asp Glu
        35                  40                  45

Ser Pro Gly Ala Asp Ala Asp Leu Gly Ser Asp His Pro Thr Ser Ser
    50                  55                  60

Ala Met Val Ala Ala Glu Asp Ser Gly Gly Ser Gly Ser Gly Gly
65                  70                  75                  80

Pro Met Arg Arg Pro Arg Gly Arg Pro Leu Gly Ser Lys Asn Lys Pro
                85                  90                  95

Lys Pro Pro Ile Ile Val Thr Arg Asp Ser Pro Asn Ala Phe His Ser
            100                 105                 110

His Val Leu Glu Val Ala Ala Gly Thr Asp Ile Val Glu Cys Val Cys
        115                 120                 125

Glu Phe Ala Arg Arg Arg Gly Arg Gly Val Ser Val Leu Ser Gly Gly
130                 135                 140

Gly Ala Val Ala Asn Val Ala Leu Arg Gln Pro Gly Ala Ser Pro Pro
145                 150                 155                 160

Gly Ser Leu Val Ala Thr Met Arg Gly Gln Phe Glu Ile Leu Ser Leu
                165                 170                 175

Thr Gly Thr Val Leu Pro Pro Ala Pro Pro Ser Ala Ser Gly Leu
            180                 185                 190

Thr Val Phe Leu Ser Gly Gly Gln Gly Gln Val Val Gly Gly Ser Val
        195                 200                 205

Ala Gly Gln Leu Ile Ala Ala Gly Pro Val Phe Leu Met Ala Ala Ser
    210                 215                 220

Phe Ala Asn Ala Val Tyr Glu Arg Leu Pro Leu Asp Gly Glu Asp Pro
225                 230                 235                 240
```

```
Glu Ala Glu Ala Ala Ala Thr Pro Pro Gly Asp Ala Ala Gln Pro
            245                 250                 255

Thr Gly Pro Pro Pro Gln Gln Gln Pro Thr Ala Ser Gln Ser Ser
        260                 265                 270

Glu Val Thr Ala Gly Asp Gly Gly Gly Gly Leu Gly Met Tyr
        275                 280                 285

Leu Gly Gly His Val Gly Ser Tyr Gln Gln Gln Gln Gln Leu Pro
        290                 295                 300

Gly Pro Gly Asp Asn Phe Gly Ser Trp Ser Gly Ser Ile Arg Pro Pro
305                 310                 315                 320

Pro Phe

<210> SEQ ID NO 44
<211> LENGTH: 299
<212> TYPE: PRT
<213> ORGANISM: Arabidopsis thaliana
<220> FEATURE:
<223> OTHER INFORMATION: G1073 polypeptide

<400> SEQUENCE: 44

Met Ser Ser Tyr Met His Pro Leu Leu Gly Gln Glu Leu His Leu Gln
1               5                   10                  15

Arg Pro Glu Asp Ser Arg Thr Pro Pro Asp Gln Asn Asn Met Glu Leu
            20                  25                  30

Asn Arg Ser Glu Ala Asp Glu Ala Lys Ala Glu Thr Thr Pro Thr Gly
        35                  40                  45

Gly Ala Thr Ser Ser Ala Thr Ala Ser Gly Ser Ser Ser Gly Arg Arg
    50                  55                  60

Pro Arg Gly Arg Pro Ala Gly Ser Lys Asn Lys Pro Lys Pro Pro Thr
65                  70                  75                  80

Ile Ile Thr Arg Asp Ser Pro Asn Val Leu Arg Ser His Val Leu Glu
                85                  90                  95

Val Thr Ser Gly Ser Asp Ile Ser Glu Ala Val Ser Thr Tyr Ala Thr
            100                 105                 110

Arg Arg Gly Cys Gly Val Cys Ile Ile Ser Gly Thr Gly Ala Val Thr
        115                 120                 125

Asn Val Thr Ile Arg Gln Pro Ala Ala Pro Ala Gly Gly Gly Val Ile
    130                 135                 140

Thr Leu His Gly Arg Phe Asp Ile Leu Ser Leu Thr Gly Thr Ala Leu
145                 150                 155                 160

Pro Pro Pro Ala Pro Pro Gly Ala Gly Gly Leu Thr Val Tyr Leu Ala
                165                 170                 175

Gly Gly Gln Gly Gln Val Val Gly Gly Asn Val Ala Gly Ser Leu Ile
            180                 185                 190

Ala Ser Gly Pro Val Val Leu Met Ala Ala Ser Phe Ala Asn Ala Val
        195                 200                 205

Tyr Asp Arg Leu Pro Ile Glu Glu Glu Thr Pro Pro Arg Thr
    210                 215                 220

Thr Gly Val Gln Gln Gln Gln Pro Glu Ala Ser Gln Ser Ser Glu Val
225                 230                 235                 240

Thr Gly Ser Gly Ala Gln Ala Cys Glu Ser Asn Leu Gln Gly Gly Asn
                245                 250                 255

Gly Gly Gly Gly Val Ala Phe Tyr Asn Leu Gly Met Asn Met Asn Asn
            260                 265                 270

Phe Gln Phe Ser Gly Gly Asp Ile Tyr Gly Met Ser Gly Gly Ser Gly
        275                 280                 285
```

```
Gly Gly Gly Gly Gly Ala Thr Arg Pro Ala Phe
    290                 295

<210> SEQ ID NO 45
<211> LENGTH: 9
<212> TYPE: PRT
<213> ORGANISM: Arabidopsis thaliana
<220> FEATURE:
<223> OTHER INFORMATION: G1073 AT-hook domain

<400> SEQUENCE: 45

Arg Arg Pro Arg Gly Arg Pro Ala Gly
1               5

<210> SEQ ID NO 46
<211> LENGTH: 120
<212> TYPE: PRT
<213> ORGANISM: Arabidopsis thaliana
<220> FEATURE:
<223> OTHER INFORMATION: G1073 DUF296 domain

<400> SEQUENCE: 46

Leu Arg Ser His Val Leu Glu Val Thr Ser Gly Ser Asp Ile Ser Glu
1               5                   10                  15

Ala Val Ser Thr Tyr Ala Thr Arg Arg Gly Cys Gly Val Cys Ile Ile
            20                  25                  30

Ser Gly Thr Gly Ala Val Thr Asn Val Thr Ile Arg Gln Pro Ala Ala
        35                  40                  45

Pro Ala Gly Gly Gly Val Ile Thr Leu His Gly Arg Phe Asp Ile Leu
    50                  55                  60

Ser Leu Thr Gly Thr Ala Leu Pro Pro Pro Ala Pro Pro Gly Ala Gly
65                  70                  75                  80

Gly Leu Thr Val Tyr Leu Ala Gly Gly Gln Gly Gln Val Val Gly Gly
                85                  90                  95

Asn Val Ala Gly Ser Leu Ile Ala Ser Gly Pro Val Val Leu Met Ala
            100                 105                 110

Ala Ser Phe Ala Asn Ala Val Tyr
        115                 120

<210> SEQ ID NO 47
<211> LENGTH: 9
<212> TYPE: PRT
<213> ORGANISM: Homo sapiens

<400> SEQUENCE: 47

Lys Arg Pro Arg Gly Arg Pro Lys Lys
1               5

<210> SEQ ID NO 48
<211> LENGTH: 16
<212> TYPE: PRT
<213> ORGANISM: Arabidopsis thaliana
<220> FEATURE:
<221> NAME/KEY: misc_feature
<222> LOCATION: (3)..(3)
<223> OTHER INFORMATION: Xaa can be Lys or Arg
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
```

-continued

```
<223> OTHER INFORMATION: CBF conserved consecutive amino acid residues

<400> SEQUENCE: 48

Pro Lys Xaa Pro Ala Gly Arg Xaa Lys Phe Xaa Glu Thr Arg His Pro
1               5                   10                  15

<210> SEQ ID NO 49
<211> LENGTH: 5
<212> TYPE: PRT
<213> ORGANISM: Arabidopsis thaliana
<220> FEATURE:
<223> OTHER INFORMATION: CBF conserved consecutive amino acid residues

<400> SEQUENCE: 49

Asp Ser Ala Trp Arg
1               5
```

PLANTS WITH IMPROVED YIELD AND STRESS TOLERANCE

RELATIONSHIP TO COPENDING APPLICATIONS

This application (the "present application") claims the benefit of U.S. provisional application 60/961,403, filed 20 Jul. 2007; and this application is a continuation-in-part of U.S. non-provisional application Ser. No. 10/669,824, filed 23 Sep. 2003 (pending), which is a continuation-in-part of U.S. non-provisional application Ser. No. 09/823,676, filed 30 Mar. 2001 (issued as U.S. Pat. No. 6,717,034); and this application is a continuation-in-part of U.S. non-provisional application Ser. No. 11/728,567, filed 26 Mar. 2007 (pending), which is a division of U.S. non-provisional application Ser. No. 10/225,066, filed 9 Aug. 2002 (issued as U.S. Pat. No. 7,238,860), which claims the benefit of each of U.S. provisional applications 60/310,847, filed 9 Aug. 2001, 60/336,049 filed 19 Nov. 2001, and 60/338,692, filed 11 Dec. 2001, and U.S. non-provisional application Ser. No. 10/225,066 is also a continuation-in-part of both U.S. non-provisional application Ser. No. 09/837,944, filed 18 Apr. 2001 (abandoned), and U.S. non-provisional application Ser. No. 10/171,468, filed 14 Jun. 2002 (abandoned); and this application is a continuation-in-part of U.S. non-provisional application Ser. No. 11/375,241, filed 16 Mar. 2006 (pending), which claims the benefit of U.S. provisional application 60/713,952, filed 31 Aug. 2005 and U.S. non-provisional application Ser. No. 11/375,241 is also a continuation-in-part of 10/225,067, filed 9 Aug. 2002 (issued as U.S. Pat. No. 7,135,616), which claims the benefit each of U.S. provisional applications 60/310,847, filed 9 Aug. 2001, 60/336,049, filed 19 Nov. 2001, and 60/338,692, filed 11 Dec. 2001, and U.S. non-provisional application Ser. No. 10/225,067 is also a continuation-in-part of both U.S. non-provisional application Ser. No. 09/837,944, filed 18 Apr. 2001 and U.S. non-provisional application Ser. No. 10/171,468, filed 14 Jun. 2002 (abandoned); and this application is a continuation-in-part of U.S. non-provisional application Ser. No. 10/374,780, filed 25 Feb. 2003 (pending), which is a continuation-in-part of both U.S. non-provisional application Ser. No. 10/225,066, filed 9 Aug. 2002 (issued as U.S. Pat. No. 7,238,860) and U.S. non-provisional application Ser. No. 10/225,067, filed 9 Aug. 2002 (issued as U.S. Pat. No. 7,135,616); and this application is a continuation-in-part of U.S. non-provisional application Ser. No. 10/546,266, filed 19 Aug. 2005 (pending), which is a '371 national Stage filing of PCT/US2004005654, filed 25 Feb. 2004 (expired), which is a continuation-in-part of U.S. non-provisional application Ser. No. 10/374,780, filed 25 Feb. 2003 (pending); and this application is a continuation-in-part of U.S. non-provisional application Ser. No. 11/642,814, filed 20 Dec. 2006 (pending), which is a division of U.S. non-provisional application Ser. No. 10/666,642, filed 18 Sep. 2003 (issued as U.S. Pat. No. 7,196,245), which claims the benefit of U.S. provisional application 60/434,166, filed 17 Dec. 2002; and this application is a continuation-in-part of U.S. non-provisional application Ser. No. 10/714,887, filed 13 Nov. 2003 (pending), which is a continuation-in-part of U.S. non-provisional application Ser. No. 10/666,642, filed 18 Sep. 2003 (issued as U.S. Pat. No. 7,196,245), which claims the benefit of U.S. provisional application 60/434,166, filed 17 Dec. 2002; and this application is a continuation-in-part of U.S. non-provisional application Ser. No. 11/435,388, filed 15 May 2006 (pending), which is a continuation-in-part of PCT/US04/37584, filed 12 Nov. 2004 (expired), which is a continuation-in-part of U.S. non-provisional application Ser. No. 10/714,887, filed 13 Nov. 2003 (pending), and PCT/US04/37584 also claims the benefit of U.S. provisional application 60/542,928, filed 5 Feb. 2004; and this application is a continuation-in-part of PCT application PCT/US2006/34615, filed 31 Aug. 2006 (pending), which claims the benefit of U.S. provisional application 60/713,952, filed 31 Aug. 2005; and this application is a continuation-in-part of U.S. non-provisional application Ser. No. 10/870,198, filed 16 Jun. 2004 (pending), which claims the benefit of both of U.S. provisional applications 60/565,948, filed 26 Apr. 2004 and U.S. provisional application 60/542,928, filed 5 Feb. 2005, and U.S. non-provisional application Ser. No. 10/870,198 is a continuation-in-part of U.S. non-provisional application Ser. No. 10/669,824, filed 23 Sep. 2003 (pending), which is a continuation-in-part of U.S. non-provisional application Ser. No. 09/823,676, filed 30 Mar. 2001 (issued as U.S. Pat. No. 6,717,034); and this application is a continuation-in-part of U.S. non-provisional application Ser. No. 11/705,903, filed 12 Feb. 2007 (pending), which is a continuation-in-part of PCT application PCT/US2006/34615, filed 31 Aug. 2006 (pending), which claims the benefit of U.S. provisional application 60/713,952, filed 31 Aug. 2005. The entire contents of each of these applications are hereby incorporated by reference.

JOINT RESEARCH AGREEMENT

The claimed invention, in the field of functional genomics and the characterization of plant genes for the improvement of plants, was made by or on behalf of Mendel Biotechnology, Inc. and Monsanto Company as a result of activities undertaken within the scope of a joint research agreement in effect on or before the date the claimed invention was made.

FIELD OF THE INVENTION

The present invention relates to plant genomics and plant improvement, including increased water use efficiency and abiotic stress tolerance, delayed development, delayed flowering, and delayed senescence, and the yield that may be obtained from a plant.

BACKGROUND OF THE INVENTION

The Effects of Various Factors on Plant Yield

Yield of commercially valuable species in the natural environment may be suboptimal as plants often grow under unfavorable conditions, such as at an inappropriate temperature or with a limited supply of soil nutrients, light, or water. Increased tolerance to abiotic stresses, such as water deprivation, salt, freezing and other hyperosmotic stresses, and cold, and heat, may improve germination, early establishment of developing seedlings, and plant development. In water-limited environments, crop yield is a function of water use, water use efficiency (WUE; defined as aerial biomass yield/water use) and the harvest index (HI; the ratio of yield biomass to the total cumulative biomass at harvest). WUE is a complex trait that involves water and $CO_2$ uptake, transport and exchange at the leaf surface (transpiration). Improved WUE has been proposed as a criterion for yield improvement under drought. Water deficit can also have adverse effects in the form of increased susceptibility to disease and pests, reduced plant growth and reproductive failure. Genes that improve WUE and tolerance to water deficit thus promote plant growth, fertility, and disease resistance. Enhanced tolerance to these stresses would lead to yield increases in conventional varieties and reduce yield variation in hybrid varieties.

Fortunately, a plant's traits, including its biochemical, developmental, or phenotypic characteristics that enhance yield or tolerance to various abiotic or biotic stresses, may be controlled through a number of cellular processes. One important way to manipulate that control is through transcription factors—proteins that influence the expression of a particular gene or sets of genes. Transformed and transgenic plants that comprise cells having altered levels of at least one selected transcription factor, for example, possess advantageous or desirable traits. Strategies for manipulating traits by altering a plant cell's transcription factor content can therefore result in plants and crops with commercially valuable properties. We have identified polynucleotides encoding At-hook family transcription factors, including G1945 and closely-related sequences (for example, SEQ ID NOs: 2, 4, 6, or 8), developed numerous transformed or transgenic plant lines using these polynucleotides, and analyzed the plants for improved traits, relative to control plants, such as greater size, greater biomass, greater yield, curlier leaves, darker coloration, greater tolerance to water deprivation, delayed flowering, delayed development, delayed senescence, greater tolerance to cold, or greater tolerance to hyperosmotic stress. In so doing, we have identified important polynucleotide and polypeptide sequences for producing commercially valuable plants and crops as well as the methods for making them and using them. Other aspects and embodiments of the invention are described below and can be derived from the teachings of this disclosure as a whole.

SUMMARY OF THE INVENTION

The invention is directed to transformed or transgenic plants, or transformed seed produced by any of the transformed or transgenic plants of the invention, wherein the transformed plants or seed comprise a transcription factor sequence of the invention. The presently disclosed subject matter also provides methods for producing a transformed plant or transformed seed. In some embodiments, the method comprises (a) transforming a plant cell with nucleic acid construct such as an expression vector, expression cassette or other DNA preparation comprising a polynucleotide sequence encoding or targeting a transcription factor polypeptide of the invention, or a fragment or derivative thereof; (b) regenerating a transformed or transgenic plant from the transformed plant cell; and (c) isolating a transformed seed from the regenerated plant. The transformed plant may have greater size, greater biomass, increased yield, greater curling of leaves, darker coloration, greater tolerance to water deprivation, more delayed flowering, more delayed development, more delayed senescence, greater tolerance to cold, or increased tolerance to a hyperosmotic stress than a control plant, for example, a non-transformed plant of the same species, or a non-transformed parental line, or a wild-type plant of the same species. In some embodiments, the transformed seed may be grown into a transgenic plant that expressed these improved traits. The transformed plant may be a eudicot or monocot plant. The polynucleotide sequence may be derived from a eudicot or monocot plant, such as, for example, soy, rice, maize, or *Arabidopsis*.

The invention also pertains to an expression vector that comprises a recombinant nucleic acid sequence of the invention, such as any of SEQ ID NO: 1, 3, 5, or 7, or a sequence that is homologous to any of these sequences, or a sequence that hybridizes to any of these sequences under stringent conditions. The recombinant nucleic acid sequence encodes a polypeptide. The polypeptide shares an amino acid identity with any of SEQ ID NO: 2, 4, 6, 8, 13, 14, 15 or 16, wherein the percent amino acid identity is at least about 51%, or at least about 52%, to about 100%. The recombinant nucleic acid sequence may specifically hybridize to the complement of the sequence set forth in SEQ ID NO: 1, 3, 5, or 7 under stringent conditions comprising two wash steps at least as stringent as 6×SSC at 65° C. of 10-30 minutes for each wash step. Greater stringency may be achieved where, for example, the two wash steps include a treatment of 0.5×SSC, 0.1% SDS at 65° C., or 0.2×SSC, with 0.1% SDS at a temperature of 65° C. for 10 to 30 minutes per wash step. When the polypeptide is overexpressed in a plant, the polypeptide regulates transcription and confers at least one regulatory activity resulting in an altered trait in the plant as compared to a control plant. The altered trait may be, for example, greater size, greater biomass, greater yield, curlier leaves, darker coloration, greater tolerance to water deprivation, more delayed flowering, more delayed development, more delayed senescence, greater tolerance to cold, or greater tolerance to hyperosmotic stress.

The invention also encompasses a method for producing a plant with greater size, greater biomass, greater yield, curlier leaves, darker coloration, greater tolerance to water deprivation, more delayed flowering, more delayed development, more delayed senescence, greater tolerance to cold, or greater tolerance to hyperosmotic stress as compared to a control plant, or to a method for increasing the tolerance of a plant to water deprivation, cold, or hyperosmotic stress, or increasing the time to flowering, various stages of development, or senescence, as compared to a control plant, the methods comprising:

(a) providing an expression vector comprising a recombinant nucleic acid sequence encoding a polypeptide sharing an amino acid identity with any of SEQ ID NO: 2, 4, 6, 8, 13, 14, 15 or 16, when the polypeptide is overexpressed in a plant, the polypeptide regulates transcription and confers at least one regulatory activity resulting in one of the aforementioned altered traits in the plant as compared to a control plant;

wherein the percent amino acid identity is between at least about 51%, or at least about 52%, to about 100% to the full-length polypeptide or to the DUF296 domain of the polypeptide; and (b) transforming a target plant with the expression vector to produce a transformed plant.

BRIEF DESCRIPTION OF THE SEQUENCE LISTING AND DRAWINGS

The Sequence Listing provides exemplary polynucleotide and polypeptide sequences of the invention. The traits associated with the use of the sequences are included in the Examples.

CD-ROMs Copy 1 and Copy 2, along with Copy 3, the CRF copy of the Sequence Listing under CFR Section 1.821(e), are read-only memory computer-readable compact discs. Each contains a copy of the Sequence Listing in ASCII text format. The Sequence Listing is named "MBI0091US.ST25.txt", the electronic file of the Sequence Listing contained on each of these CD-ROMs was created on 22 Oct. 2007, and each is 81 kilobytes in size. The copies of the Sequence Listing on the CD-ROM discs are hereby incorporated by reference in their entirety.

FIG. 1 shows a conservative estimate of phylogenetic relationships among the orders of flowering plants (modified from Soltis et al., 1997). Those plants with a single cotyledon (monocots) are a monophyletic clade nested within at least two major lineages of dicots; the eudicots are further divided into rosids and asterids. *Arabidopsis* is a rosid eudicot classified within the order Brassicales; rice is a member of the monocot order Poales. FIG. 1 was adapted from Daly et al., 2001.

Figure 1:
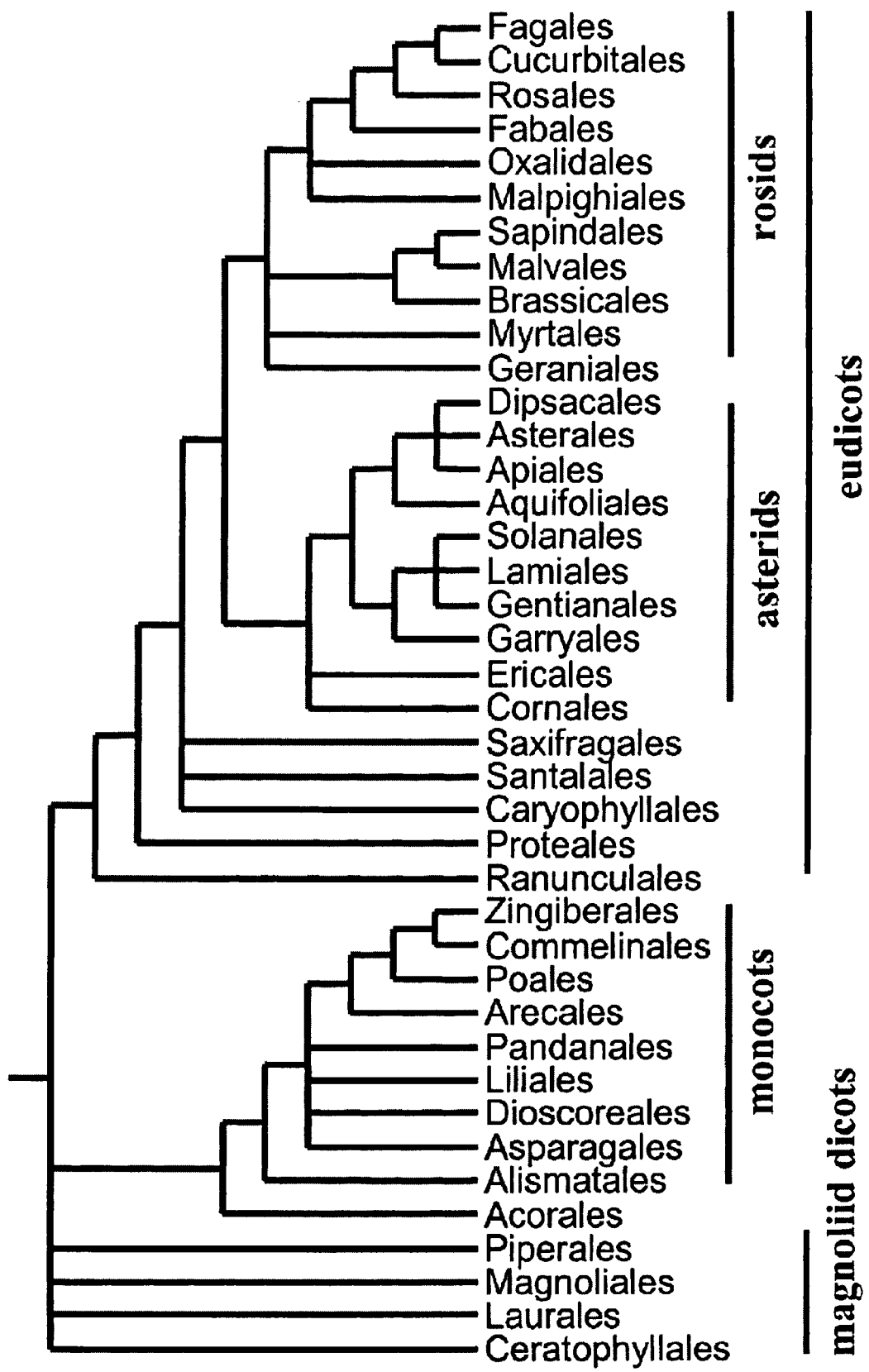

Gap Opening Penalty: 10.00
Gap Extension Penalty: 0.20
Protein weight matrix: Gonnet series
Residue-specific Penalties: ON
Hydrophobic Penalties: ON
Gap Separation Distance: 4
End Gap Separation: OFF
Use negative matrix: OFF The phylogenetic tree was generated in MEGA3 using the neighbor joining algorithm and a p-distance model. Alignment gaps were handled using a pairwise deletion algorithm. A test of phylogeny was done via bootstrap with 1000 replications and Random Seed set to default. Cut off values of the bootstrap tree were set to 50%. The arrow indicates the ancestral node from which the G1945 subclade is derived. SEQ ID NOs: are found in the parentheses.

FIGS. 4A-4B present a multiple sequence alignment of full length G1945 and closely-related proteins, prepared using ClustalX software and the full-length protein sequences. These polypeptides were identified by BLAST and phylogenetic analysis. The AT-hook and DUF296 domains are indicated by bars below the alignment in FIGS. 4A-4B. SEQ ID NOs: are found in the parentheses.

DETAILED DESCRIPTION

The present invention relates to polynucleotides and polypeptides for modifying phenotypes of plants, particularly those associated with increased abiotic stress tolerance and increased yield with respect to a control plant (for example, a wild-type plant). Throughout this disclosure, various information sources are referred to and/or are specifically incorporated. The information sources include scientific journal articles, patent documents, textbooks, and World Wide Web browser-inactive page addresses. While the reference to these information sources clearly indicates that they can be used by one of skill in the art, each and every one of the information sources cited herein are specifically incorporated in their entirety, whether or not a specific mention of "incorporation by reference" is noted. The contents and teachings of each and every one of the information sources can be relied on and used to make and use embodiments of the invention.

As used herein and in the appended claims, the singular forms "a", "an", and "the" include the plural reference unless the context clearly dictates otherwise. Thus, for example, a reference to "a host cell" includes a plurality of such host cells, and a reference to "a stress" is a reference to one or more stresses and equivalents thereof known to those skilled in the art, and so forth.

DEFINITIONS

"Polynucleotide" is a nucleic acid molecule comprising a plurality of polymerized nucleotides, e.g., at least about 15 consecutive polymerized nucleotides. A polynucleotide may be a nucleic acid, oligonucleotide, nucleotide, or any fragment thereof. In many instances, a polynucleotide comprises a nucleotide sequence encoding a polypeptide (or protein) or a domain or fragment thereof. Additionally, the polynucleotide may comprise a promoter, an intron, an enhancer region, a polyadenylation site, a translation initiation site, 5' or 3' untranslated regions, a reporter gene, a selectable marker, or the like. The polynucleotide can be single-stranded or double-stranded DNA or RNA. The polynucleotide optionally comprises modified bases or a modified backbone. The polynucleotide can be, e.g., genomic DNA or RNA, a transcript (such as an mRNA), a cDNA, a PCR product, a cloned DNA, a synthetic DNA or RNA, or the like. The polynucleotide can be combined with carbohydrate, lipids, protein, or other materials to perform a particular activity such as transformation or form a useful composition such as a peptide nucleic acid (PNA). The polynucleotide can comprise a sequence in either sense or antisense orientations. "Oligonucleotide" is substantially equivalent to the terms amplimer, primer, oligomer, element, target, and probe and is preferably single-stranded.

A "recombinant polynucleotide" is a polynucleotide that is not in its native state, e.g., the polynucleotide comprises a nucleotide sequence not found in nature, or the polynucleotide is in a context other than that in which it is naturally found, e.g., separated from nucleotide sequences with which it typically is in proximity in nature, or adjacent (or contiguous with) nucleotide sequences with which it typically is not in proximity. For example, the sequence at issue can be cloned into a vector, or otherwise recombined with one or more additional nucleic acid.

An "isolated polynucleotide" is a polynucleotide, whether naturally occurring or recombinant, that is present outside the cell in which it is typically found in nature, whether purified or not. Optionally, an isolated polynucleotide is subject to one or more enrichment or purification procedures, e.g., cell lysis, extraction, centrifugation, precipitation, or the like.

"Gene" or "gene sequence" refers to the partial or complete coding sequence of a gene, its complement, and its 5' or 3' untranslated regions. A gene is also a functional unit of inheritance, and in physical terms is a particular segment or sequence of nucleotides along a molecule of DNA (or RNA, in the case of RNA viruses) involved in producing a polypeptide chain. The latter may be subjected to subsequent processing such as chemical modification or folding to obtain a functional protein or polypeptide. A gene may be isolated, partially isolated, or found with an organism's genome. By way of example, a transcription factor gene encodes a transcription factor polypeptide, which may be functional or require processing to function as an initiator of transcription.

Operationally, genes may be defined by the cis-trans test, a genetic test that determines whether two mutations occur in the same gene and that may be used to determine the limits of the genetically active unit (Rieger et al., 1976). A gene generally includes regions preceding ("leaders"; upstream) and following ("trailers"; downstream) the coding region. A gene may also include intervening, non-coding sequences, referred to as "introns", located between individual coding segments, referred to as "exons". Most genes have an associated promoter region, a regulatory sequence 5' of the transcription initiation codon (there are some genes that do not have an identifiable promoter). The function of a gene may also be regulated by enhancers, operators, and other regulatory elements.

A "polypeptide" is an amino acid sequence comprising a plurality of consecutive polymerized amino acid residues e.g., at least about 15 consecutive polymerized amino acid residues. In many instances, a polypeptide comprises a polymerized amino acid residue sequence that is a transcription factor or a domain or portion or fragment thereof. Additionally, the polypeptide may comprise: (i) a localization domain; (ii) an activation domain; (iii) a repression domain; (iv) an oligomerization domain; (v) a protein-protein interaction domain; (vi) a DNA-binding domain; or the like. The polypeptide optionally comprises modified amino acid residues, naturally occurring amino acid residues not encoded by a codon, non-naturally occurring amino acid residues.

"Protein" refers to an amino acid sequence, oligopeptide, peptide, polypeptide or portions thereof whether naturally occurring or synthetic.

"Portion", as used herein, refers to any part of a protein used for any purpose, but especially for the screening of a library of molecules which specifically bind to that portion or for the production of antibodies.

A "recombinant polypeptide" is a polypeptide produced by translation of a recombinant polynucleotide. A "synthetic polypeptide" is a polypeptide created by consecutive polymerization of isolated amino acid residues using methods well known in the art. An "isolated polypeptide," whether a naturally occurring or a recombinant polypeptide, is more enriched in (or out of) a cell than the polypeptide in its natural state in a wild-type cell, e.g., more than about 5% enriched, more than about 10% enriched, or more than about 20%, or more than about 50%, or more, enriched, i.e., alternatively denoted: 105%, 110%, 120%, 150% or more, enriched relative to wild type standardized at 100%. Such an enrichment is not the result of a natural response of a wild-type plant. Alternatively, or additionally, the isolated polypeptide is separated from other cellular components with which it is typically associated, e.g., by any of the various protein purification methods herein.

"Homology" refers to sequence similarity between a reference sequence and at least a fragment of a newly sequenced clone insert or its encoded amino acid sequence.

"Identity" or "similarity" refers to sequence similarity between two polynucleotide sequences or between two polypeptide sequences, with identity being a more strict comparison. The phrases "percent identity" and "% identity" refer to the percentage of sequence similarity found in a comparison of two or more polynucleotide sequences or two or more polypeptide sequences. "Sequence similarity" refers to the percent similarity in base pair sequence (as determined by any suitable method) between two or more polynucleotide sequences. Two or more sequences can be anywhere from 0-100% similar, or any integer value therebetween. Identity or similarity can be determined by comparing a position in each sequence that may be aligned for purposes of comparison. When a position in the compared sequence is occupied by the same nucleotide base or amino acid, then the molecules are identical at that position. A degree of similarity or identity between polynucleotide sequences is a function of the number of identical, matching or corresponding nucleotides at positions shared by the polynucleotide sequences. A degree of identity of polypeptide sequences is a function of the number of identical amino acids at corresponding positions shared by the polypeptide sequences. A degree of homology or similarity of polypeptide sequences is a function of the number of amino acids at corresponding positions shared by the polypeptide sequences.

"Alignment" refers to a number of nucleotide bases or amino acid residue sequences aligned by lengthwise comparison so that components in common (i.e., nucleotide bases or amino acid residues at corresponding positions) may be visually and readily identified. The fraction or percentage of components in common is related to the homology or identity between the sequences. Alignments such as those of FIGS. 4A-4B may be used to identify conserved domains and relatedness within these domains. An alignment may suitably be determined by means of computer programs known in the art, such as MACVECTOR software, (1999; Accelrys, Inc., San Diego, Calif.).

A "conserved domain" or "conserved region" as used herein refers to a region in heterologous polynucleotide or polypeptide sequences where there is a relatively high degree of sequence identity between the distinct sequences. With respect to polynucleotides encoding presently disclosed polypeptides, a conserved domain is preferably at least nine base pairs (bp) in length. Transcription factor sequences that possess or encode for conserved domains that have a minimum percentage identity and have comparable biological activity to the present polypeptide sequences, thus being members of the same subclade of transcription factor polypeptides, are encompassed by the invention. Overexpression in a transformed plant of a polypeptide that comprises, for example, a conserved domain having DNA-binding, activation or nuclear localization activity results in the transformed plant having similar improved traits as other transformed plants overexpressing other members of the same subclade of transcription factor polypeptides.

A fragment or domain can be referred to as outside a conserved domain, outside a consensus sequence, or outside a consensus DNA-binding site that is known to exist or that exists for a particular polypeptide class, family, or sub-family. In this case, the fragment or domain will not include the exact amino acids of a consensus sequence or consensus DNA-binding site of a transcription factor class, family or sub-family, or the exact amino acids of a particular transcription factor consensus sequence or consensus DNA-binding site. Furthermore, a particular fragment, region, or domain of a polypeptide, or a polynucleotide encoding a polypeptide, can be "outside a conserved domain" if all the amino acids of the fragment, region, or domain fall outside of a defined conserved domain(s) for a polypeptide or protein. Sequences having lesser degrees of identity but comparable biological activity are considered to be equivalents.

As one of ordinary skill in the art recognizes, conserved domains may be identified as regions or domains of identity to a specific consensus sequence (see, for example, Riechmann et al., 2000a, 2000b). Thus, by using alignment methods well known in the art, the conserved domains of the plant polypeptides may be determined.

The conserved domains for many of the polypeptide sequences of the invention are listed in Table 1. Also, the polypeptides of Table 1 have conserved domains specifically indicated by amino acid coordinate start and stop sites. A comparison of the regions of these polypeptides allows one of skill in the art (see, for example, Reeves and Nissen, 1995, to identify domains or conserved domains for any of the polypeptides listed or referred to in this disclosure.

"Complementary" refers to the natural hydrogen bonding by base pairing between purines and pyrimidines. For example, the sequence A-C-G-T (5'->3') forms hydrogen bonds with its complements A-C-G-T (5'->3') or A-C-G-U (5'->3'). Two single-stranded molecules may be considered partially complementary, if only some of the nucleotides bond, or "completely complementary" if all of the nucleotides bond. The degree of complementarity between nucleic acid strands affects the efficiency and strength of hybridization and amplification reactions. "Fully complementary" refers to the case where bonding occurs between every base pair and its complement in a pair of sequences, and the two sequences have the same number of nucleotides.

The terms "highly stringent" or "highly stringent condition" refer to conditions that permit hybridization of DNA strands whose sequences are highly complementary, wherein these same conditions exclude hybridization of significantly mismatched DNAs. Polynucleotide sequences capable of hybridizing under stringent conditions with the polynucleotides of the present invention may be, for example, variants of the disclosed polynucleotide sequences, including allelic or splice variants, or sequences that encode orthologs or paralogs of presently disclosed polypeptides. Nucleic acid hybridization methods are disclosed in detail by Kashima et al., 1985, Sambrook et al., 1989, and by Haymes et al., 1985, which references are incorporated herein by reference.

In general, stringency is determined by the temperature, ionic strength, and concentration of denaturing agents (e.g., formamide) used in a hybridization and washing procedure (for a more detailed description of establishing and determining stringency, see the section "Identifying Polynucleotides or Nucleic Acids by Hybridization", below). The degree to which two nucleic acids hybridize under various conditions of stringency is correlated with the extent of their similarity. Thus, similar nucleic acid sequences from a variety of sources, such as within a plant's genome (as in the case of paralogs) or from another plant (as in the case of orthologs) that may perform similar functions can be isolated on the basis of their ability to hybridize with known related polynucleotide sequences. Numerous variations are possible in the conditions and means by which nucleic acid hybridization can be performed to isolate related polynucleotide sequences having similarity to sequences known in the art and are not limited to those explicitly disclosed herein. Such an approach may be used to isolate polynucleotide sequences having various degrees of similarity with disclosed polynucleotide sequences, such as, for example, encoded transcription factors having about 51.9% or greater identity with the conserved domain of disclosed sequences.

The terms "paralog" and "ortholog" are defined below in the section entitled "Orthologs and Paralogs". In brief, orthologs and paralogs are evolutionarily related genes that have similar sequences and functions. Orthologs are structurally related genes in different species that are derived by a speciation event. Paralogs are structurally related genes within a single species that are derived by a duplication event.

The term "equivalog" describes members of a set of homologous proteins that are conserved with respect to function since their last common ancestor. Related proteins are grouped into equivalog families, and otherwise into protein families with other hierarchically defined homology types. This definition is provided at the Institute for Genomic Research (TIGR) World Wide Web (www) website, "tigr.org" under the heading "Terms associated with TIGRFAMs".

In general, the term "variant" refers to molecules with some differences, generated synthetically or naturally, in their base or amino acid sequences as compared to a reference (native) polynucleotide or polypeptide, respectively. These differences include substitutions, insertions, deletions or any desired combinations of such changes in a native polynucleotide of amino acid sequence.

With regard to polynucleotide variants, differences between presently disclosed polynucleotides and polynucleotide variants are limited so that the nucleotide sequences of the former and the latter are closely similar overall and, in many regions, identical. Due to the degeneracy of the genetic code, differences between the former and latter nucleotide sequences may be silent (i.e., the amino acids encoded by the polynucleotide are the same, and the variant polynucleotide sequence encodes the same amino acid sequence as the presently disclosed polynucleotide. Variant nucleotide sequences may encode different amino acid sequences, in which case such nucleotide differences will result in amino acid substitutions, additions, deletions, insertions, truncations or fusions with respect to the similar disclosed polynucleotide sequences. These variations may result in polynucleotide variants encoding polypeptides that share at least one functional characteristic. The degeneracy of the genetic code also dictates that many different variant polynucleotides can encode identical and/or substantially similar polypeptides in addition to those sequences illustrated in the Sequence Listing.

Also within the scope of the invention is a variant of a nucleic acid listed in the Sequence Listing, that is, one having a sequence that differs from the one of the polynucleotide sequences in the Sequence Listing, or a complementary sequence, that encodes a functionally equivalent polypeptide (i.e., a polypeptide having some degree of equivalent or similar biological activity) but differs in sequence from the sequence in the Sequence Listing, due to degeneracy in the genetic code. Included within this definition are polymorphisms that may or may not be readily detectable using a particular oligonucleotide probe of the polynucleotide encoding polypeptide, and improper or unexpected hybridization to allelic variants, with a locus other than the normal chromosomal locus for the polynucleotide sequence encoding polypeptide.

"Allelic variant" or "polynucleotide allelic variant" refers to any of two or more alternative forms of a gene occupying the same chromosomal locus. Allelic variation arises naturally through mutation, and may result in phenotypic polymorphism within populations. Gene mutations may be "silent" or may encode polypeptides having altered amino acid sequence. "Allelic variant" and "polypeptide allelic variant" may also be used with respect to polypeptides, and in this case the terms refer to a polypeptide encoded by an allelic variant of a gene.

"Splice variant" or "polynucleotide splice variant" as used herein refers to alternative forms of RNA transcribed from a gene. Splice variation naturally occurs as a result of alternative sites being spliced within a single transcribed RNA molecule or between separately transcribed RNA molecules, and may result in several different forms of mRNA transcribed from the same gene. Thus, splice variants may encode polypeptides having different amino acid sequences, which may or may not have similar functions in the organism. "Splice variant" or "polypeptide splice variant" may also refer to a polypeptide encoded by a splice variant of a transcribed mRNA.

As used herein, "polynucleotide variants" may also refer to polynucleotide sequences that encode paralogs and orthologs of the presently disclosed polypeptide sequences. "Polypeptide variants" may refer to polypeptide sequences that are paralogs and orthologs of the presently disclosed polypeptide sequences.

Differences between presently disclosed polypeptides and polypeptide variants are limited so that the sequences of the former and the latter are closely similar overall and, in many regions, identical. Presently disclosed polypeptide sequences and similar polypeptide variants may differ in amino acid sequence by one or more substitutions, additions, deletions, fusions and truncations, which may be present in any combination. These differences may produce silent changes and result in a functionally equivalent polypeptide. Thus, it will be readily appreciated by those of skill in the art, that any of a variety of polynucleotide sequences is capable of encoding the polypeptides and homolog polypeptides of the invention. A polypeptide sequence variant may have "conservative" changes, wherein a substituted amino acid has similar structural or chemical properties. Deliberate amino acid substitutions may thus be made on the basis of similarity in polarity, charge, solubility, hydrophobicity, hydrophilicity, and/or the amphipathic nature of the residues, as long as a significant amount of the functional or biological activity of the polypeptide is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine. More rarely, a variant may have "non-conservative" changes, e.g., replacement of a glycine with a tryptophan. Similar minor variations may also include amino acid deletions or insertions, or both. Related polypeptides may comprise, for example, additions and/or deletions of one or more N-linked or O-linked glycosylation sites, or an addition and/or a deletion of one or more cysteine residues. Guidance in determining which and how many amino acid residues may be substituted, inserted or deleted without abolishing functional or biological activity may be found using computer programs well known in the art, for example, DNASTAR software (see U.S. Pat. No. 5,840,544).

"Fragment", with respect to a polynucleotide, refers to a clone or any part of a polynucleotide molecule that retains a usable, functional characteristic. Useful fragments include oligonucleotides and polynucleotides that may be used in hybridization or amplification technologies or in the regulation of replication, transcription or translation. A "polynucleotide fragment" refers to any subsequence of a polynucleotide, typically, of at least about 9 consecutive nucleotides, preferably at least about 30 nucleotides, more preferably at least about 50 nucleotides, of any of the sequences provided herein. Exemplary polynucleotide fragments are the first sixty consecutive nucleotides of the polynucleotides listed in the Sequence Listing. Exemplary fragments also include fragments that comprise a region that encodes an conserved domain of a polypeptide. Exemplary fragments also include fragments that comprise a conserved domain of a polypeptide.

Fragments may also include subsequences of polypeptides and protein molecules, or a subsequence of the polypeptide. Fragments may have uses in that they may have antigenic potential. In some cases, the fragment or domain is a subsequence of the polypeptide which performs at least one biological function of the intact polypeptide in substantially the same manner, or to a similar extent, as does the intact polypeptide. For example, a polypeptide fragment can comprise a recognizable structural motif or functional domain such as a DNA-binding site or domain that binds to a DNA promoter region, an activation domain, or a domain for protein-protein interactions, and may initiate transcription. Fragments can vary in size from as few as 3 amino acid residues to the full length of the intact polypeptide, but are preferably at least about 30 amino acid residues in length and more preferably at least about 60 amino acid residues in length. Exemplary fragments of the sequences of the invention thus include fragments that comprise a conserved AT-hook domain, a DUF296 domain of a polypeptide of the invention, for example, of G11945 (SEQ ID NO: 2 amino acid residues 83-207), G2155 (SEQ ID NO: 4 residues 49-173) or G3936 (SEQ ID NO: 6 residues 97-217), or a proline-rich putative activation domain (for example, those shown in FIG. 4A, Table 3).

The invention also encompasses production of DNA sequences that encode polypeptides and derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding polypeptides or any fragment thereof.

"Derivative" refers to the chemical modification of a nucleic acid molecule or amino acid sequence. Chemical modifications can include replacement of hydrogen by an alkyl, acyl, or amino group or glycosylation, pegylation, or any similar process that retains or enhances biological activity or lifespan of the molecule or sequence.

Figure 2:
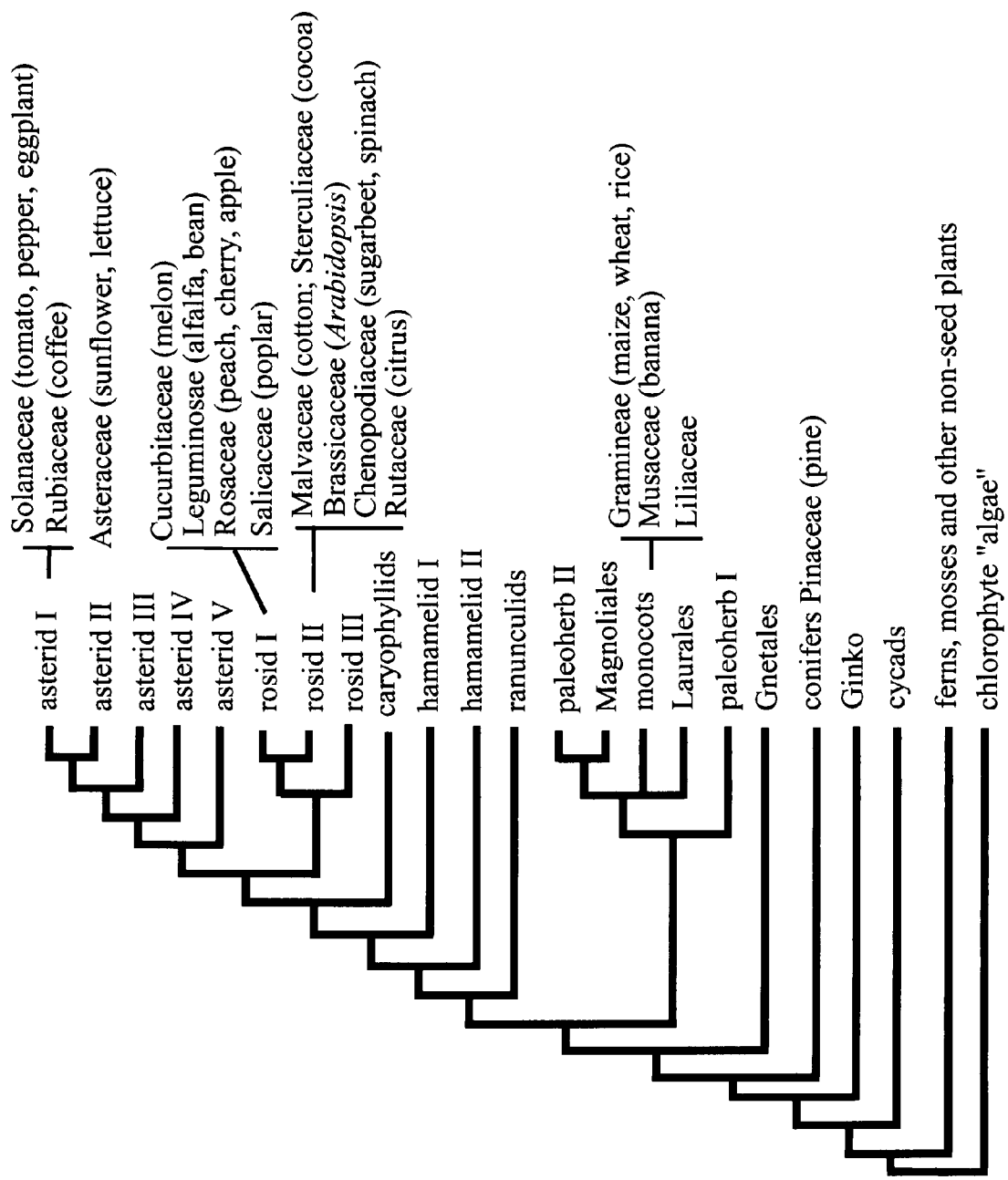
FIG. 2 shows a phylogenic dendogram depicting phylogenetic relationships of higher plant taxa, including clades containing tomato and *Arabidopsis*; adapted from Ku et al., 2000; and Chase et al., 1993.

The term "plant" includes whole plants, shoot vegetative organs/structures (for example, leaves, stems and tubers), roots, flowers and floral organs/structures (for example, bracts, sepals, petals, stamens, carpels, anthers and ovules), seed (including embryo, endosperm, and seed coat) and fruit (the mature ovary), plant tissue (for example, vascular tissue, ground tissue, and the like) and cells (for example, guard cells, egg cells, and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, horsetails, psilophytes, lycophytes, bryophytes, and multicellular algae (see for example, FIG. 1, adapted from Daly et al., 2001, FIG. 2, adapted from Ku et al., 2000; and see also Tudge, 2000.

A "control plant" as used in the present invention refers to a plant cell, seed, plant component, plant tissue, plant organ or whole plant used to compare against transformed, transgenic or genetically modified plant for the purpose of identifying an enhanced phenotype in the transformed, transgenic or genetically modified plant. A control plant may in some cases be a transformed or transgenic plant line that comprises an empty vector or marker gene, but does not contain the recombinant polynucleotide of the present invention that is expressed in the transformed, transgenic or genetically modified plant being evaluated. In general, a control plant is a plant of the same line or variety as the transformed, transgenic or genetically modified plant being tested. A suitable control plant would include a genetically unaltered or non-transgenic plant of the parental line used to generate a transformed or transgenic plant herein.

"Wild type" or "wild-type", as used herein, refers to a plant cell, seed, plant component, plant tissue, plant organ or whole plant that has not been genetically modified or treated in an experimental sense. Wild-type cells, seed, components, tissue, organs or whole plants may be used as controls to compare levels of expression and the extent and nature of trait modification with cells, tissue or plants of the same species in which a polypeptide's expression is altered, e.g., in that it has been knocked out, overexpressed, or ectopically expressed.

"Transformation" refers to the transfer of a foreign polynucleotide sequence into the genome of a host organism such as that of a plant or plant cell. Typically, the foreign genetic material has been introduced into the plant by human manipulation, but any method can be used as one of skill in the art recognizes. Examples of methods of plant transformation include *Agrobacterium*-mediated transformation (De Blaere et al., 1987) and biolistic methodology (Klein et al., 1987, U.S. Pat. No. 4,945,050).

A "transformed plant", which may also be referred to as a "transgenic plant" or "transformant", generally refers to a plant, a plant cell, plant tissue, seed or calli that has been through, or is derived from a plant that has been through, a transformation process in which a nucleic acid construct such as an expression vector, expression cassette, plasmid or nucleic acid preparation that contains at least one foreign polynucleotide sequence is introduced into the plant. The expression vector or cassette contains genetic material that is not found in a wild-type plant of the same species, variety or cultivar. The genetic material may include a regulatory element, a transgene (for example, a foreign transcription factor sequence), an insertional mutagenesis event (such as by transposon or T-DNA insertional mutagenesis), an activation tagging sequence, a mutated sequence, a homologous recombination event, a sequence designed to engineer a change at an endogenous locus through a DNA-repair mechanism, or a sequence modified by chimeraplasty. In some embodiments the regulatory and transcription factor sequence may be derived from the host plant, but by their incorporation into an expression vector of cassette, represent an arrangement of the polynucleotide sequences not found a wild-type plant of the same species, variety or cultivar.

An "untransformed plant" is a plant that has not been through the transformation process.

A "stably transformed" plant, plant cell or plant tissue has generally been selected and regenerated on a selection media following transformation.

An expression vector or cassette typically comprises a polypeptide-encoding sequence operably linked (i.e., under regulatory control of) to appropriate inducible or constitutive regulatory sequences that allow for the controlled expression of polypeptide. The expression vector or cassette can be introduced into a plant by transformation or by breeding after transformation of a parent plant. A plant refers to a whole plant as well as to a plant part, such as seed, fruit, leaf, or root, plant tissue, plant cells or any other plant material, e.g., a plant explant, as well as to progeny thereof, and to in vitro systems that mimic biochemical or cellular components or processes in a cell.

A "trait" refers to a physiological, morphological, biochemical, or physical characteristic of a plant or particular plant material or cell. In some instances, this characteristic is visible to the human eye, such as seed or plant size, or can be measured by biochemical techniques, such as detecting the protein, starch, or oil content of seed or leaves, or by observation of a metabolic or physiological process, e.g. by measuring tolerance to water deprivation or particular salt or sugar concentrations, or by the observation of the expression level of a gene or genes, e.g., by employing Northern analysis, RT-PCR, microarray gene expression assays, or reporter gene expression systems, or by agricultural observations such as hyperosmotic stress tolerance or yield. Any technique can be used to measure the amount of, comparative level of, or difference in any selected chemical compound or macromolecule in the transformed or transgenic plants, however.

"Trait modification" refers to a detectable difference in a characteristic in a plant ectopically expressing, transformed with, or genetically modified using a polynucleotide or polypeptide of the present invention relative to a plant not doing so, such as a wild-type plant. In some cases, the trait modification can be evaluated quantitatively. For example, the trait modification can entail at least about a 2% increase or decrease, or an even greater difference, in an observed trait as compared with a control or wild-type plant. It is known that there can be a natural variation in the modified trait. Therefore, the trait modification observed entails a change of the normal distribution and magnitude of the trait in the plants as compared to control or wild-type plants.

When two or more plants have "similar morphologies", "substantially similar morphologies", "a morphology that is substantially similar", or are "morphologically similar", the plants have comparable forms or appearances, including analogous features such as overall dimensions, height, width, mass, root mass, shape, glossiness, color, stem diameter, leaf size, leaf dimension, leaf density, internode distance, branching, root branching, number and form of inflorescences, and other macroscopic characteristics, and the individual plants are not readily distinguishable based on morphological characteristics alone.

"Modulates" refers to a change in activity (biological, chemical, or immunological) or lifespan resulting from specific binding between a molecule and either a nucleic acid molecule or a protein.

The term "transcript profile" refers to the expression levels of a set of genes in a cell in a particular state, particularly by comparison with the expression levels of that same set of genes in a cell of the same type in a reference state. For example, the transcript profile of a particular polypeptide in a suspension cell is the expression levels of a set of genes in a cell knocking out or overexpressing that polypeptide compared with the expression levels of that same set of genes in a suspension cell that has normal levels of that polypeptide. The transcript profile can be presented as a list of those genes whose expression level is significantly different between the two treatments, and the difference ratios. Differences and similarities between expression levels may also be evaluated and calculated using statistical and clustering methods.

With regard to gene knockouts as used herein, the term "knockout" refers to a plant or plant cell having a mutation in at least one gene in the plant or cell, where the mutation results in reduced or altered expression or reduced or altered activity of the polypeptide encoded by that gene compared to a control cell. The knockout can be the result of, for example, genomic disruptions, including transposons, tilling, and homologous recombination, antisense constructs, sense constructs, RNA silencing constructs, RNA interference, or targeted engineering of a gene at an endogenous locus by means of a homology dependent DNA repair process. A T-DNA insertion within a gene is an example of a genotypic alteration that may abolish expression of that gene.

"Ectopic expression or altered expression" in reference to a polynucleotide indicates that the pattern of expression in, e.g., a transformed or transgenic plant or plant tissue, is different from the expression pattern in a wild-type plant or a reference plant of the same species. The pattern of expression may also be compared with a reference expression pattern in a wild-type plant of the same species. For example, the polynucleotide or polypeptide is expressed in a cell or tissue type other than a cell or tissue type in which the sequence is expressed in the wild-type plant, or by expression at a time other than at the time the sequence is expressed in the wild-type plant, or by a response to different inducible agents, such as hormones or environmental signals, or at different expression levels (either higher or lower) compared with those found in a wild-type plant. The term also refers to altered expression patterns that are produced by lowering the levels of expression to below the detection level or completely abolishing expression. The resulting expression pattern can be transient or stable, constitutive or inducible. In reference to a polypeptide, the terms "ectopic expression" or "altered expression" further may relate to altered activity levels resulting from the interactions of the polypeptides with exogenous or endogenous modulators or from interactions with factors or as a result of the chemical modification of the polypeptides.

The term "overexpression" as used herein refers to a greater expression level of a gene in a plant, plant cell or plant tissue, compared to expression in a wild-type plant, cell or tissue, at any developmental or temporal stage for the gene. Overexpression can occur when, for example, the genes encoding one or more polypeptides are under the control of a strong promoter (e.g., the cauliflower mosaic virus 35S transcription initiation region). Overexpression may also under the control of an inducible or tissue specific promoter. Thus, overexpression may occur throughout a plant, in specific tissues or cells of the plant, or in the presence or absence of particular environmental signals, depending on the promoter used.

Overexpression may take place in plant cells normally lacking expression of polypeptides functionally equivalent or identical to the present polypeptides. Overexpression may also occur in plant cells where endogenous expression of the present polypeptides or functionally equivalent molecules normally occurs, but such normal expression is at a lower level. Overexpression thus results in a greater than normal production, or "overproduction" of the polypeptide in the plant, cell or tissue.

The terms "transcription regulating region" or "cis regulatory element" refer to a DNA regulatory sequence that regulates expression of one or more genes in a plant when a transcription factor having one or more specific binding domains binds to the DNA regulatory sequence. Transcription factors typically possess a conserved DNA binding domain. The transcription factors also typically comprise an amino acid subsequence that forms a transcriptional activation or repression domain that regulates expression of one or more abiotic stress tolerance genes in a plant when the transcription factor binds to the regulating region.

"Yield" or "plant yield" refers to increased plant growth, increased crop growth, increased biomass, and/or increased plant product production, and is dependent to some extent on temperature, plant size, organ size, planting density, light, water and nutrient availability, and how the plant copes with various stresses, such as through temperature acclimation and water or nutrient use efficiency.

"Planting density" refers to the number of plants that can be grown per acre. For crop species, planting or population density varies from a crop to a crop, from one growing region to another, and from year to year. Using corn as an example, the average prevailing density in 2000 was in the range of 20,000-25,000 plants per acre in Missouri, USA. A desirable higher population density (a measure of yield) would be at least 22,000 plants per acre, and a more desirable higher population density would be at least 28,000 plants per acre, more preferably at least 34,000 plants per acre, and most preferably at least 40,000 plants per acre. The average prevailing densities per acre of a few other examples of crop plants in the USA in the year 2000 were: wheat 1,000,000-1,500,000; rice 650,000-900,000; soybean 150,000-200,000, canola 260,000-350,000, sunflower 17,000-23,000 and cotton 28,000-55,000 plants per acre (U.S. Pat. No. 7,208,652 to Cheikh et al., 2003). A desirable higher population density for each of these examples, as well as other valuable species of plants, would be at least 10% higher than the average prevailing density or yield.

DESCRIPTION OF THE SPECIFIC EMBODIMENTS

Transcription Factors Modify Expression of Endogenous Genes

A transcription factor may include, but is not limited to, any polypeptide that can activate or repress transcription of a single gene or a number of genes. As one of ordinary skill in the art recognizes, transcription factors can be identified by the presence of a region or domain of structural similarity or identity to a specific consensus sequence or the presence of a specific consensus DNA-binding motif (see, for example, Riechmann et al., 2000a). The plant transcription factors of the present invention are putative transcription factors.

Generally, transcription factors are involved in the control of gene expression which leads to changes in cellular processes including cell differentiation and proliferation and the regulation of growth. Accordingly, one skilled in the art would recognize that by expressing the present sequences in a plant, one may change the expression of autologous genes or induce the expression of introduced genes. By affecting the expression of similar autologous sequences in a plant that have the biological activity of the present sequences, or by introducing the present sequences into a plant, one may alter a plant's phenotype to one with improved traits related to osmotic stresses. The sequences of the invention may also be used to transform a plant and introduce desirable traits not found in the wild-type cultivar or strain. Plants may then be selected for those that produce the most desirable degree of over- or under-expression of target genes of interest and coincident trait improvement.

The sequences of the present invention may be from any species, particularly plant species, in a naturally occurring form or from any source whether natural, synthetic, semi-synthetic or recombinant. The sequences of the invention may also include fragments of the present amino acid sequences. Where "amino acid sequence" is recited to refer to an amino acid sequence of a naturally occurring protein molecule, "amino acid sequence" and like terms are not meant to limit the amino acid sequence to the complete native amino acid sequence associated with the recited protein molecule.

In addition to methods for modifying a plant phenotype by employing one or more polynucleotides and polypeptides of the invention described herein, the polynucleotides and polypeptides of the invention have a variety of additional uses. These uses include their use in the recombinant production (i.e., expression) of proteins; as regulators of plant gene expression, as diagnostic probes for the presence of complementary or partially complementary nucleic acids (including for detection of natural coding nucleic acids); as substrates for further reactions, e.g., mutation reactions, PCR reactions, or the like; as substrates for cloning e.g., including digestion or ligation reactions; and for identifying exogenous or endogenous modulators of the transcription factors. The polynucleotide can be, e.g., genomic DNA or RNA, a transcript (such as an mRNA), a cDNA, a PCR product, a cloned DNA, a synthetic DNA or RNA, or the like. The polynucleotide can comprise a sequence in either sense or antisense orientations.

Expression of genes that encode polypeptides that modify expression of endogenous genes, polynucleotides, and proteins are well known in the art. In addition, transformed or transgenic plants comprising isolated polynucleotides encoding transcription factors may also modify expression of endogenous genes, polynucleotides, and proteins. Examples include Peng et al., 1997, and Peng et al., 1999. In addition, many others have demonstrated that an *Arabidopsis* transcription factor expressed in an exogenous plant species elicits the same or very similar phenotypic response. See, for example, Fu et al., 2001; Nandi et al., 2000; Coupland, 1995; and Weigel and Nilsson, 1995.

In another example, Mandel et al., 1992b, and Suzuki et al., 2001, teach that a transcription factor expressed in another plant species elicits the same or very similar phenotypic response of the endogenous sequence, as often predicted in earlier studies of *Arabidopsis* transcription factors in *Arabidopsis* (see Mandel et al., 1992a; Suzuki et al., 2001). Other examples include Müller et al., 2001; Kim et al., 2001; Kyozuka and Shimamoto, 2002; Boss and Thomas, 2002; He et al., 2000; and Robson et al., 2001.

In yet another example, Gilmour et al., 1998, teach an *Arabidopsis* AP2 transcription factor, CBF1, which, when overexpressed in transgenic plants, increases plant freezing tolerance. Jaglo et al., 2001, further identified sequences in *Brassica napus* which encode CBF-like genes and that transcripts for these genes accumulated rapidly in response to low temperature. Transcripts encoding CBF-like proteins were also found to accumulate rapidly in response to low temperature in wheat, as well as in tomato. An alignment of the CBF proteins from *Arabidopsis, B. napus*, wheat, rye, and tomato revealed the presence of conserved consecutive amino acid residues, PKK/RPAGRxKFxETRHP (SEQ ID NO: 48) and DSAWR (SEQ ID NO: 49), which bracket the AP2/EREBP DNA binding domains of the proteins and distinguish them from other members of the AP2/EREBP protein family. (Jaglo et al., 2001)

Transcription factors mediate cellular responses and control traits through altered expression of genes containing cis-acting nucleotide sequences that are targets of the introduced transcription factor. It is well appreciated in the art that the effect of a transcription factor on cellular responses or a cellular trait is determined by the particular genes whose expression is either directly or indirectly (e.g., by a cascade of transcription factor binding events and transcriptional changes) altered by transcription factor binding. In a global analysis of transcription comparing a standard condition with one in which a transcription factor is overexpressed, the resulting transcript profile associated with transcription factor overexpression is related to the trait or cellular process controlled by that transcription factor. For example, the PAP2 gene and other genes in the MYB family have been shown to control anthocyanin biosynthesis through regulation of the expression of genes known to be involved in the anthocyanin biosynthetic pathway (Bruce et al., 2000; and Borevitz et al., 2000). Further, global transcript profiles have been used successfully as diagnostic tools for specific cellular states (e.g., cancerous vs. non-cancerous; Bhattacharjee et al., 2001; and Xu et al., 2001). Consequently, it is evident to one skilled in the art that similarity of transcript profile upon overexpression of different transcription factors would indicate similarity of transcription factor function.

Polypeptides and Polynucleotides of the Invention

The present invention includes putative transcription factors (TFs), and isolated or recombinant polynucleotides encoding the polypeptides, or novel sequence variant polypeptides or polynucleotides encoding novel variants of polypeptides derived from the specific sequences provided in the Sequence Listing; the recombinant polynucleotides of the invention may be incorporated in expression vectors for the purpose of producing transformed plants. Also provided are methods for modifying yield from a plant by modifying the mass, size or number of plant organs or seed of a plant by controlling a number of cellular processes, and for increasing a plant's resistance to abiotic stresses. These methods are based on the ability to alter the expression of critical regulatory molecules that may be conserved between diverse plant species. Related conserved regulatory molecules may be originally discovered in a model system such as *Arabidopsis* and homologous, functional molecules then discovered in other plant species. The latter may then be used to confer increased yield or abiotic stress tolerance in diverse plant species.

Exemplary polynucleotides encoding the polypeptides of the invention were identified in the *Arabidopsis thaliana* GenBank database using publicly available sequence analysis programs and parameters. Sequences initially identified were then further characterized to identify sequences comprising specified sequence strings corresponding to sequence motifs present in families of known polypeptides. In addition, further exemplary polynucleotides encoding the polypeptides of the invention were identified in the plant GenBank database using publicly available sequence analysis programs and parameters. Sequences initially identified were then further characterized to identify sequences comprising specified sequence strings corresponding to sequence motifs present in families of known polypeptides.

Additional polynucleotides of the invention were identified by screening *Arabidopsis thaliana* and/or other plant cDNA libraries with probes corresponding to known polypeptides under low stringency hybridization conditions. Additional sequences, including full length coding sequences, were subsequently recovered by the rapid amplification of cDNA ends (RACE) procedure using a commercially available kit according to the manufacturer's instructions. Where necessary, multiple rounds of RACE are performed to isolate 5' and 3' ends. The full-length cDNA was then recovered by a routine end-to-end polymerase chain reaction (PCR) using primers specific to the isolated 5' and 3' ends. Exemplary sequences are provided in the Sequence Listing.

Background Information for G1945, the G1945 Subclade and Related Sequences

G11945 is a member of the AT-hook family of transcription factors. Enhanced yield was observed in soybean lines expressing G3936 (SEQ ID NO: 6; the soy ortholog of G1945) from promoters that drive expression in seed.

At-Hook Protein Structure

An At-hook motif or domain, such as is found in a polypeptide member of At-hook transcription factor family, is an example of a conserved domain that are characteristic of a particular transcription factor family, clade or subclade. The AT-hook motif was first recognized in the non-histone chromosomal protein HMG-I(Y) and is a short, highly-conserved, DNA binding protein motif that comprises a conserved nine amino acid peptide, the seminal sequence of which is KRPRGRPKK (SEQ ID NO: 47); Reeves and Nissen, 1990) and is capable of binding to the minor groove of DNA (Reeves and Nissen, 1990). At the center of this AT-hook motif is a short, strongly conserved tripeptide comprised of glycine-arginine-proline (GRP; Aravind and Landsman, 1998). AT-hook proteins can have one or several copies of the motif. In general, it appears that it is an auxiliary protein motif cooperating with other DNA-binding activities, and that it facilitates changes in chromatin structure (Aravind and Landsman, 1998). In the sequences examined thus far, the At-hook domain of G1945 subclade members have generally been found to comprise the consensus sequence: X-R/K-P/R/K-R-G-R-P-P/R-G (SEQ ID NO: 21), where X is any amino acid.

The mammalian HMG-I(Y)/HMGA proteins participate in a wide variety of nuclear processes including chromosome and chromatin remodeling, acting as architectural transcription factors that regulate the expression of numerous genes in vivo. In particular, they are thought to facilitate formation of stereospecific complexes comprising the transcriptional machinery which associate on the promoter/enhancer regions of inducible genes. Such complexes have been dubbed "enhanceosomes" (Bianchi and Beltrame, 2000). The mammalian HMGA proteins have little, if any, secondary structure in solution but assume distinct conformations when bound to substrates such as DNA or other proteins. Their intrinsic flexibility allows the HMGA proteins to participate in specific protein-DNA and protein-protein interactions that induce both structural changes in chromatin substrates and "enhanceosome" formation (Reeves and Beckerbauer, 2001). It has been shown that HMGA proteins specifically interact with a large number of other proteins, most of which are transcription factors (Reeves, 2001). They are also subject to many types of post-translational modification. One example is phosphorylation, which markedly influences their ability to interact with DNA substrates, other proteins, and chromatin (Onate et al., 1994; Falvo et al., 1995; Reeves and Nissen, 1995; Huth et al., 1997).

*Arabidopsis* has 34 genes encoding AT-hook motif containing proteins. These 34 genes fall in to three distinct phylogenetic clades: "A", "B", and "C". Clade A contains 15 genes (including G1945), all of which have a single AT-hook motif followed by a conserved DUF296 domain. According to the National Center for Biotechnology Information (NCBI), DUF296 represents a "[d]omain of unknown function. This putative domain is found in proteins that contain AT-hook motifs pfam02178, which strongly suggests a DNA-binding function for the proteins as a whole, however the function of this domain is unknown" (ncbi.nlm.nih.gov/BLAST/Blast.cgi).

AT-hook proteins show clade-specific phenotypic and expression characteristics. We have shown that Clade A genes produced distinct phenotypes when they were constitutively expressed in *Arabidopsis*. Transgenic plants were typically late flowering with broad rounded or contorted leaves. Many of the plant lines overexpressing Clade A genes also showed signs of stress tolerance in plate and soil based assays. The native expression of Clade A genes generally appears to be tightly regulated, and focused in roots and reproductive organs.

Sequences found in *Arabidopsis* and other plant species that are closely-related to G1945 are listed in Table 1, which also lists G1073, which lies just outside of the G1945 subclade and is included in Table 1 for comparison purposes (as shown below, G1073 does confer some of the traits conferred by G1945 subclade members). Table 1 shows the SEQ ID NO. and the species from which the sequence was derived (Column 1); the Gene Identifier or Genbank accession number predicted sequence ("GID" or "Genbank", in Column 2); the percent identity of the polypeptide in Column 1 to the full length G1945 polypeptide, SEQ ID NO: 2, as determined by a BLASTp analysis with a wordlength (W) of 3, an expectation (E) of 10, and the BLOSUM62 scoring matrix Henikoff & Henikoff, 1989 (Column 3); the amino acid coordinates for the conserved AT-hook and DUF296 domains, beginning at the n-terminus of each of the sequences (Column 4), the SEQ ID NO: of each conserved DUF296 DNA binding domain (Column 5); the conserved At-hook and DUF296 domain sequences of the respective polypeptides (Column 6); and the percentage identity of the conserved domain in Column 6 to the conserved DUF296 domain of the G1945 sequence, SEQ ID NO: 13 (Column 7). Column 7 also includes the ratio of the number of identical residues over the total number of residues compared in the respective DUF296 domains (in parentheses). The sequences with accession numbers DY027620, BG543096, and DT508378 have not been tested in plants, but were discovered with database-mining analysis described identified in the plant GenBank database using publicly available sequence analysis programs and parameters. Sequences initially identified were then further characterized to identify sequences comprising specified sequence strings corresponding to sequence motifs present in families of known polypeptides.

TABLE 1

Sequences and conserved domains closely related within the G1945 subclade

| Col. 1 SEQ ID NO: and species from which sequence is derived | Col. 2 Gene ID (GID) or Genbank acc. no. | Col. 3 Percent ID of protein to G1945 | Col. 4 AT-hook and DUF296 domain amino acid coordinates | Col. 5 AT-hook and DUF296 domain SEQ ID NO: | Col. 6 AT-hook and DUF296 domains | Col. 7 Percent ID of DUF296 domain to G1945 DUF296 domain |
|---|---|---|---|---|---|---|
| 1,2 *Arabidopsis thaliana* | GID: G1945 | | At-hook: 56-64 DUF296: 83-207 | 9,13 | At-hook: RRPRGRPPG DUF296: MSPYILEVPSGNDVVEAINR FCRRKSIGVCVLSGSGSVAN VTLRQPSPAALGSTITFHGK FDLLSVSATFLPPPPRTSLS PPVSNFFTVSLAGPQGQIIG GFVAGPLISAGTVYVIAASF NNPSY | 100% (125/125) |
| *Brassica oleracea* | Genbank: DY 027620 | | At-hook: N/A DUF296: 21-144 | | At-hook: N/A DUF296: MSPYILEVPSGNDVVEAINR FCRRKSIGVCVLSGSGSVAN ITLRQPSPAAPGSTITFHGK FDLLSVSATFLPPPPRTSLS PPVANFFTVSLAGPQGQIIG GFVAGPLISAGTVYVIAASF NNPSY | 97.6% (122/125) |
| *Brassica rapa* subsp. *pekinensis* | Genbank: BG 543096 | | At-hook: 20-28 DUF296: 47-171 | | At-hook: RRPRGRPPG DUF296: MSPYILEVPSGNDVVEAINR FCRRKSIGVCVLSGSGSVAN | 97.6% (122/125) |

TABLE 1-continued

Sequences and conserved domains closely related within the G1945 subclade

| Col. 1 SEQ ID NO: and species from which sequence is derived | Col. 2 Gene ID (GID) or Genbank acc. no. | Col. 3 Percent ID of protein to G1945 | Col. 4 AT-hook and DUF296 domain amino acid coordinates | Col. 5 At-hook and DUF296 domain SEQ ID NO: | Col. 6 AT-hook and DUF296 domains | Col. 7 Percent ID of DUF296 domain to G1945 DUF296 domain |
|---|---|---|---|---|---|---|
| | | | | | ITLRQPSPAAPGSTITFHGK FDLLSVSATFLPPPPRTSLS PPVANFFTVSLAGPQGQIIG GFVAGPLISAGTVYVIAASF NNPSY | |
| 3,4 Arabidopsis thaliana | GID: G2155 | | At-hook: 24-32 DUF296: 49-173 | 10,14 | At-hook: GRPRGRPRG DUF296: MSPYILEVPSGNDVVEALN RFCRGKAIGFCVLSGSGSV ADVTLRQPSPAAPGSTITF HGKFDLLSVSATFLPPLPP TSLSPPVSNFFTVSLAGPQ GKVIGGFVAGPLVAAGTVY FVATSFKNPSY | 87.2% (109/125) |
| Populus trichocarpax Populus deltoides | Genbank: DT 508378 | | At-hook: 86-94 DUF296: 113-232 | | At-hook: RRPRGRPPG DUF296: MSPYILEVPGGNDVVEALS RFCRRKNMGICVLTGSGTV ANVTLRQPSATPGATITFH GRFDILSISATFLPQTASY PVPNSFTISLAGPQGQIVG GIVAGSLVAAGTVFVVAAS FNNPSY | 73.6% (92/125) |
| 5,6 Glycine max | GID G3936 | | At-hook: 69-77 DUF296: 97-217 | 11,15 | At-hook: RRPRGRPPG DUF296: MSPYILEVSGGNDVVEAIA QFSHRKNMGICVLTGSGTV ANVTLRQPSTTPGTTVTFH GRFDILSVSATFLPQQSGA SPAVPNGFAISLAGPQGQI VGGLVAGGLMAAGTVFVIA AGFNNPA | 69.6% (87/125) |
| 7,8 Oryza sativa | GID: G3408 | | At-hook: 82-90 DUF296: 111-240 | 12,16 | At-hook: KKRRGRPPG DUF296: MRPHVIEIPGGRDVAEALA RFSSRRNLGICVLAGTGAV ANVSLRHPSPGVPGSAPAA IVFHGRYEILSLSATFLPP AMSSVAPQAAVAAAGLSIS LAGPHGQIVGGAVAGPLYA ATTVVVVAAAFTNPTF | 51.9% (68/131) |
| 44 Arabidopsis thaliana | GID: G1073 | | At-hook: 63-71 DUF296: 90-209 | 45,46 | At-hook: RRPRGRPAG DUF296: LRSHVLEVTSGSDISEAVST YATRRGCGVCIISGTGAVTN VTIRQPAAPAGGGVITLHGR FDILSLTGTALPPPAPPGAG GLTVYLAGGQGQVVGGNVAG SLIASGPVVLMAASFANAVY | 50.8% (62/122) |

Thus, with respect to polynucleotides encoding presently disclosed polypeptides, a conserved domain is preferably at least nine base pairs (bp) in length. A conserved domain with respect to presently disclosed polypeptides refers to a domain within a polypeptide family that exhibits a higher degree of sequence homology. The full length polypeptides of the invention, as well as their conserved DUF296 domains that are characteristic of the AT-hook transcription factor family or G1945 subclade, are contemplated to have at least about 51%, at least about 51.9%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 69.6%, at least about 70%, at least about 71%, at least about 72%, at least about 73%, at least about 73.6%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 87.2%, at least about 88%, at least about 89%, at least about 90%, at least about 91%, at least about 92%, at least about 93%, at least about 94%, at least about 95%, at least about 96%, at least about 97%, at least about 97.6%, at least about 98%, at least about 99%, and about 100% amino acid residue sequence identity, to a polypeptide of the invention (e.g., SEQ ID NO: 2, 4, 6, 8) or a conserved domain of a polypeptide of the invention (e.g., SEQ ID NOs: 13-16), or to one or more of the listed full-length sequences, or to a listed sequence but excluding or outside of the known consensus sequence or consensus DNA-binding site.

Sequences that possess or encode for conserved domains that meet these criteria of percentage identity, and that have comparable biological activity to the present polypeptide sequences, thus being members of the G1945 subclade polypeptides, are encompassed by the invention. The At-hook domains are required for conferring similar functions in the transcription factors of the invention. Overexpression in a transformed plant of a polypeptide that comprises AT-hook and DUF296 conserved domains encompassed by the present invention results in the transformed plant having greater size, greater biomass, increased yield, curlier leaves, darker coloration, greater tolerance to water deprivation, delayed flowering, more delayed development, more delayed senescence, greater tolerance to cold, and/or increased tolerance to hyperosmotic stress than the control plant, as compared to a control plant.

Residues within a highly conserved region of a protein may be so conserved because of their importance to the function of that protein. Alignments of the sequences in the G1945 subclade (FIGS. 4A-4B, Tables 2 and 3) indicate a high degree of conservation of the At-hook and DUF296 domains, and particular residues, in subclade members. Tables 2 and 3 show the high degree of conservation found with the DUF296 domain (Table 3) and a putative activation domain near the C-termini of the G1945 subclade proteins. The row below the amino acid alignments of Tables 2 and 3 show identical residues represented by asterisks, and similar residues represented by periods) within the DUF296 domains and in the putative activation domains near the C-termini of the G1945 subclade.

TABLE 2

Highly conserved residues within DUF296 domains of the G1945 subclade

| GID or acc. no. | DUF296 SEQ ID NO: | DUF296 domain |
|---|---|---|
| G1945 | 13 | MSPYILEVPSGNDVVEAINRFCRRKSIGVCVLSGSGSVANVTLRQPSPAA |
| G2155 | 14 | MSPYILEVPSGNDVVEALNRFCRGKAIGFCVLSGSGSVADVTLRQPSPAA |
| G3936 | 15 | MSPYILEVSGGNDVVEAIAQFSHRKNMGICVLTGSGTVANVTLRQPS-TT |
| G3408 | 16 | MRPHVIEIPGGRDVAEALARFSSRRNLGICVLAGTGAVANVSLRHPSPGV |
| DY027620 | | MSPYILEVPSGNDVVEAINRFCRRKSIGVCVLSGSGSVANITLRQPSPAA |
| EG666921 | | MSPYILEVCGGSDVVEAISRFCRRKNIGICVLTGSGTVANVTLRQPS-TT |
| DY264181 | | MSPYILEVPGGNDVVETISNFCRRKNIGICVLTGSGTVANVTLRQPS-AT |
| Identical or similar residues | | * * ..*.  * **   . *.  . .* ***.*.*. ...** |
| G1945 | 13 | LGST---ITFHGKFDLLSVSATFLPPPPR--TSLSPPVSNFFTVSLAGPQ |
| G2155 | 14 | PGST---ITFHGKFDLLSVSATFLPPLPP--TSLSPPVSNFFTVSLAGPQ |
| G3936 | 15 | PGTT---VTFHGRFDILSVSATFLPQQSGAS----PAVPNGFAISLAGPQ |
| G3408 | 16 | PGSAPAATVFHGRYETLSLSATFLPPAMSSVAPQAAVAAAGLSISLAGPH |
| DY027620 | | PGST---ITFHGKFDLLSVSATFLPPPPR--TSLSPPVANFFTVSLAGPQ |
| EG666921 | | PGST---ITFHGRFDILSISATFMPQT-----VSYP-VPNTFTISLAGPQ |
| DY264181 | | PGST---ITFHGRFDILSISATFLPQN-----AAYPPLPNIFAISLAGPQ |
| Identical or similar residues | | *..    *......***.*          .  . ...*****. |
| G1945 | 13 | GQIIGGFVAGPLISAGTVYVIAASFNNPSY |
| G2155 | 14 | GKVIGGFVAGPLVAAGTVYFVATSFKNPSY |
| G3936 | 15 | GQIVGGLVAGGLMAAGTVFVIAASFNNPAY |
| G3408 | 16 | GQIVGGAVAGPLYAATTVVVVAAAFTNPTF |
| DY027620 | | GQIIGGFVAGPLISAGTVYVIAASFNNPSY |
| EG666921 | | GQIVCGLVAGSLIAAGTVYIMAATFNNPSY |
| DY264181 | | GQIVGGSVVGPLLAVGTVFVVAATFNNPSY |
| Identical or similar residues | | *...** *.* * .. ** .*..* **.. |

The DUF296 domain of G1945 subclade members, another example of a characteristic conserved domain of the G1945 subclade, has generally been found, in the sequences examined thus far, to comprise the consensus sequence:

M-X-P-X-I/V-L/I-E-V/I-X-S/A/G-G-X-D-V-X-E/Q-A/T-I/L/V-X$_2$-F-C/S-X$_2$-K/R-X-I/M/L-G-X-C-V-L-S/T/A-G-S/T-G-S/T/A-V-A-N/D-V/I-T/S-L-R-Q/H-P-S-X$_{1-2}$-A/T/V-X-

G-S/T-T/A-$X_{0-3}$-I/V-T/V-F-H-G-R/K-F/Y-D/E-L/I-L-S-V/I/L-S/T-A-T-F-L/M-P-$X_{11-16}$-F/L-S/A/T-V/I-S-L-A-G-P-Q/H-G-Q/K-I/V-I/V-G-G-X-V-AN-G-X-L-X-A/S-A/V-X-T-V-$X_2$-I/V/M-A-A/T-S/T/A-F-X-N-P-S/A/T-Y/F (SEQ ID NO: 22), where slashes indicate one of two to three residues shown may be present at that position, and X can be any amino acid residue. Within the DUF296 domains of the G1945 subclade sequences examined thus far are contained the smaller highly conserved subsequences L-S-V/I/L-S/T-A-T-F-L/M-P (SEQ ID NO: 23) and S-L-A-G-P-Q/H-G (SEQ ID NO: 24).

TABLE 3

Highly conserved residues within putative C-terminal activation domains of the G1945 subclade

| Polypeptide Gene ID (GID) | GID SEQ ID NO: | Putative C-terminal activation domain found in polypeptide |
|---|---|---|
| G1945 | 2 | DVIWAPTAR----APPP-Y |
| G2155 | 4 | DVIWDPNAK----APSP-Y |
| G3936 | 6 | DVIWAPTAR----PPPPPY |
| G3408 | 8 | EVMWPPPARTPHPPPPPPY |
| Identical or similar residues | | .*.* * *.     * * * |

Many of the sequences in the Sequence Listing, derived from diverse plant species, have been ectopically expressed in overexpressor plants. The changes in the characteristic(s) or trait(s) of the plants were then observed and found to confer increased yield and/or increased abiotic stress tolerance. Therefore, the polynucleotides and polypeptides can be used to improve desirable characteristics of plants.

The polynucleotides of the invention were also ectopically expressed in overexpressor plant cells and the changes in the expression levels of a number of genes, polynucleotides, and/or proteins of the plant cells observed. Therefore, the polynucleotides and polypeptides can be used to change expression levels of genes, polynucleotides, and/or proteins of plants or plant cells.

The data presented herein represent the results obtained in experiments with polynucleotides and polypeptides that may be expressed in plants for the purpose of reducing yield losses that arise from biotic and abiotic stress.

Orthologs and Paralogs

Homologous sequences as described above can comprise orthologous or paralogous sequences. Several different methods are known by those of skill in the art for identifying and defining these functionally homologous sequences. General methods for identifying orthologs and paralogs, including phylogenetic methods, sequence similarity and hybridization methods, are described herein; an ortholog or paralog, including equivalogs, may be identified by one or more of the methods described below.

As described by Eisen, 1998, evolutionary information may be used to predict gene function. It is common for groups of genes that are homologous in sequence to have diverse, although usually related, functions. However, in many cases, the identification of homologs is not sufficient to make specific predictions because not all homologs have the same function. Thus, an initial analysis of functional relatedness based on sequence similarity alone may not provide one with a means to determine where similarity ends and functional relatedness begins. Fortunately, it is well known in the art that protein function can be classified using phylogenetic analysis of gene trees combined with the corresponding species. Functional predictions can be greatly improved by focusing on how the genes became similar in sequence (i.e., by evolutionary processes) rather than on the sequence similarity itself (Eisen, 1998). In fact, many specific examples exist in which gene function has been shown to correlate well with gene phylogeny (Eisen, 1998). Thus, "[t]he first step in making functional predictions is the generation of a phylogenetic tree representing the evolutionary history of the gene of interest and its homologs. Such trees are distinct from clusters and other means of characterizing sequence similarity because they are inferred by techniques that help convert patterns of similarity into evolutionary relationships .... After the gene tree is inferred, biologically determined functions of the various homologs are overlaid onto the tree. Finally, the structure of the tree and the relative phylogenetic positions of genes of different functions are used to trace the history of functional changes, which is then used to predict functions of [as yet] uncharacterized genes" (Eisen, 1998).

Within a single plant species, gene duplication may cause two copies of a particular gene, giving rise to two or more genes with similar sequence and often similar function known as paralogs. A paralog is therefore a similar gene formed by duplication within the same species. Paralogs typically cluster together or in the same clade (a group of similar genes) when a gene family phylogeny is analyzed using programs such as CLUSTAL (Thompson et al., 1994; Higgins et al., 1996). Groups of similar genes can also be identified with pair-wise BLAST analysis (Feng and Doolittle, 1987). For example, a clade of very similar MADS domain transcription factors from *Arabidopsis* all share a common function in flowering time (Ratcliffe et al., 2001), and a group of very similar AP2 domain transcription factors from *Arabidopsis* are involved in tolerance of plants to freezing (Gilmour et al., 1998). Analysis of groups of similar genes with similar function that fall within one clade can yield sub-sequences that are particular to the clade. These sub-sequences, known as consensus sequences, can not only be used to define the sequences within each clade, but define the functions of these genes; genes within a clade may contain paralogous sequences, or orthologous sequences that share the same function (see also, for example, Mount, 2001).

Transcription factor gene sequences are conserved across diverse eukaryotic species lines (Goodrich et al., 1993; Lin et al., 1991; Sadowski et al., 1988). Plants are no exception to this observation; diverse plant species possess transcription factors that have similar sequences and functions. Speciation, the production of new species from a parental species, gives rise to two or more genes with similar sequence and similar function. These genes, termed orthologs, often have an identical function within their host plants and are often interchangeable between species without losing function. Because plants have common ancestors, many genes in any plant species will have a corresponding orthologous gene in another plant species. Once a phylogenic tree for a gene family of one species has been constructed using a program such as CLUSTAL (Thompson et al., 1994); Higgins et al., 1996) potential orthologous sequences can be placed into the phylogenetic tree and their relationship to genes from the species of interest can be determined. Orthologous sequences can also be identified by a reciprocal BLAST strategy. Once an orthologous sequence has been identified, the function of the ortholog can be deduced from the identified function of the reference sequence.

By using a phylogenetic analysis, one skilled in the art would recognize that the ability to predict similar functions conferred by closely-related polypeptides is predictable. This predictability has been confirmed by our own many studies in which we have found that a wide variety of polypeptides have orthologous or closely-related homologous sequences that function as does the first, closely-related reference sequence. For example, distinct transcription factors, including:

(i) AP2 family *Arabidopsis* G47 (found in U.S. Pat. No. 7,135,616 to Heard), a phylogenetically-related sequence from soybean, and two phylogenetically-related homologs from rice all can confer greater tolerance to drought, hyperosmotic stress, or delayed flowering as compared to control plants;

(ii) CAAT family *Arabidopsis* G481 (found in PCT patent publication WO2004076638), and numerous phylogenetically-related sequences from eudicots and monocots can confer greater tolerance to drought-related stress as compared to control plants;

(iii) Myb-related *Arabidopsis* G682 (found in U.S. Pat. No. 7,223,904 to Heard) and numerous phylogenetically-related sequences from eudicots and monocots can confer greater tolerance to heat, drought-related stress, cold, and salt as compared to control plants;

(iv) WRKY family *Arabidopsis* G1274 (found in U.S. Pat. No. 7,196,245 to Jiang) and numerous closely-related sequences from eudicots and monocots have been shown to confer increased water deprivation tolerance, and (v) AT-hook family soy sequence G3456 (found in US patent publication 20040128712A1) and numerous phylogenetically-related sequences from eudicots and monocots, increased biomass compared to control plants when these sequences are overexpressed in plants.

The polypeptides sequences belong to a distinct subclade of polypeptides that include members from diverse species. In each case, most or all of the subclade member sequences derived from both eudicots and monocots have been shown to confer increased size, biomass, yield or tolerance to one or more abiotic stresses when the sequences were overexpressed. These studies each demonstrate that evolutionarily conserved genes from diverse species are likely to function similarly (i.e., by regulating similar target sequences and controlling the same traits), and that polynucleotides from one species may be transformed into closely-related or distantly-related plant species to confer or improve traits.

At the nucleotide level, the sequences of the invention will typically share at least about 30% or 40% nucleotide sequence identity, preferably at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100% sequence identity to one or more of the listed full-length sequences, or to a region of a listed sequence excluding or outside of the region(s) encoding a known consensus sequence or consensus DNA-binding site, or outside of the region(s) encoding one or all conserved domains. The degeneracy of the genetic code enables major variations in the nucleotide sequence of a polynucleotide while maintaining the amino acid sequence of the encoded polypeptide.

Percent identity can be determined electronically, e.g., by using the MEGALIGN program (DNASTAR, Inc. Madison, Wis.). The MEGALIGN program can create alignments between two or more sequences according to different methods, for example, the clustal method (see, for example, Higgins and Sharp, 1988). The clustal algorithm groups sequences into clusters by examining the distances between all pairs. The clusters are aligned pairwise and then in groups. Other alignment algorithms or programs may be used, including FASTA, BLAST, or ENTREZ, FASTA and BLAST, and which may be used to calculate percent similarity. These are available as a part of the GCG sequence analysis package (University of Wisconsin, Madison, Wis.), and can be used with or without default settings. ENTREZ is available through the National Center for Biotechnology Information. In one embodiment, the percent identity of two sequences can be determined by the GCG program with a gap weight of 1, e.g., each amino acid gap is weighted as if it were a single amino acid or nucleotide mismatch between the two sequences (see U.S. Pat. No. 6,262,333).

Software for performing BLAST analyses is publicly available, e.g., through the National Center for Biotechnology Information (see internet website at www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul, 1990; Altschul et al., 1993). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, n=−4, and a comparison of both strands. For amino acid sequences, the BLASTP program uses as defaults a wordlength (W) of 3, an expectation (E) of 10, and the BLOSUM62 scoring matrix (see Henikoff and Henikoff, 1989). Unless otherwise indicated for comparisons of predicted polynucleotides, "sequence identity" refers to the % sequence identity generated from a tblastx using the NCBI version of the algorithm at the default settings using gapped alignments with the filter "off" (see, for example, internet website at www.ncbi.nlm.nih.gov/).

Other techniques for alignment are described by Doolittle, 1996. Preferably, an alignment program that permits gaps in the sequence is utilized to align the sequences. The Smith-Waterman is one type of algorithm that permits gaps in sequence alignments (see Shpaer, 1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

The percentage similarity between two polypeptide sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between polynucleotide sequences can also be counted or calculated by other methods known in the art, e.g., the Jotun Hein method (see, for example, Hein, 1990) Identity between sequences can also be determined by other methods known in the art, e.g., by varying hybridization conditions (see US Patent Application No. 20010010913).

Thus, the invention provides methods for identifying a sequence similar or paralogous or orthologous or homologous to one or more polynucleotides as noted herein, or one or more target polypeptides encoded by the polynucleotides, or otherwise noted herein and may include linking or associating a given plant phenotype or gene function with a sequence. In the methods, a sequence database is provided (locally or across an internet or intranet) and a query is made against the sequence database using the relevant sequences herein and associated plant phenotypes or gene functions.

In addition, one or more polynucleotide sequences or one or more polypeptides encoded by the polynucleotide sequences may be used to search against a BLOCKS (Bairoch et al., 1997), PFAM, and other databases which contain previously identified and annotated motifs, sequences and gene functions. Methods that search for primary sequence patterns with secondary structure gap penalties (Smith et al., 1992) as well as algorithms such as Basic Local Alignment Search Tool (BLAST; Altschul, 1990; Altschul et al., 1993), BLOCKS (Henikoff and Henikoff, 1991), Hidden Markov Models (HMM; Eddy, 1996; Sonnhammer et al., 1997), and the like, can be used to manipulate and analyze polynucleotide and polypeptide sequences encoded by polynucleotides. These databases, algorithms and other methods are well known in the art and are described in Ausubel et al., 1997, and in Meyers, 1995.

A further method for identifying or confirming that specific homologous sequences control the same function is by comparison of the transcript profile(s) obtained upon overexpression or knockout of two or more related polypeptides. Since transcript profiles are diagnostic for specific cellular states, one skilled in the art will appreciate that genes that have a highly similar transcript profile (e.g., with greater than 50% regulated transcripts in common, or with greater than 70% regulated transcripts in common, or with greater than 90% regulated transcripts in common) will have highly similar functions. Fowler and Thomashow, 2002, have shown that three paralogous AP2 family genes (CBF1, CBF2 and CBF3) are induced upon cold treatment, and each of which can condition improved freezing tolerance, and all have highly similar transcript profiles. Once a polypeptide has been shown to provide a specific function, its transcript profile becomes a diagnostic tool to determine whether paralogs or orthologs have the same function.

Furthermore, methods using manual alignment of sequences similar or homologous to one or more polynucleotide sequences or one or more polypeptides encoded by the polynucleotide sequences may be used to identify regions of similarity and conserved domains characteristic of a particular transcription factor family. Such manual methods are well-known of those of skill in the art and can include, for example, comparisons of tertiary structure between a polypeptide sequence encoded by a polynucleotide that comprises a known function and a polypeptide sequence encoded by a polynucleotide sequence that has a function not yet determined. Such examples of tertiary structure may comprise predicted alpha helices, beta-sheets, amphipathic helices, leucine zipper motifs, zinc finger motifs, proline-rich regions, cysteine repeat motifs, and the like.

Orthologs and paralogs of presently disclosed polypeptides may be cloned using compositions provided by the present invention according to methods well known in the art. cDNAs can be cloned using mRNA from a plant cell or tissue that expresses one of the present sequences. Appropriate mRNA sources may be identified by interrogating Northern blots with probes designed from the present sequences, after which a library is prepared from the mRNA obtained from a positive cell or tissue. Polypeptide-encoding cDNA is then isolated using, for example, PCR, using primers designed from a presently disclosed gene sequence, or by probing with a partial or complete cDNA or with one or more sets of degenerate probes based on the disclosed sequences. The cDNA library may be used to transform plant cells. Expression of the cDNAs of interest is detected using, for example, microarrays, Northern blots, quantitative PCR, or any other technique for monitoring changes in expression. Genomic clones may be isolated using similar techniques to those.

Examples of orthologs of the *Arabidopsis* polypeptide sequences and their functionally similar orthologs are listed in Table 1 and the Sequence Listing. In addition to the sequences in Table 1 and the Sequence Listing, the invention encompasses isolated nucleotide sequences that are phylogenetically and structurally similar to sequences listed in the Sequence Listing) and can function in a plant by increasing yield and/or and abiotic stress tolerance when ectopically expressed in a plant.

Since a significant number of these sequences are phylogenetically and sequentially related to each other and have been shown to increase yield from a plant and/or abiotic stress tolerance, one skilled in the art would predict that other similar, phylogenetically related sequences falling within the present subclade of polypeptides would also perform similar functions when ectopically expressed.

Identifying Polynucleotides or Nucleic Acids by Hybridization

Polynucleotides homologous to the sequences illustrated in the Sequence Listing and tables can be identified, e.g., by hybridization to each other under stringent or under highly stringent conditions. Single stranded polynucleotides hybridize when they associate based on a variety of well characterized physical-chemical forces, such as hydrogen bonding, solvent exclusion, base stacking and the like. The stringency of a hybridization reflects the degree of sequence identity of the nucleic acids involved, such that the higher the stringency, the more similar are the two polynucleotide strands. Stringency is influenced by a variety of factors, including temperature, salt concentration and composition, organic and non-organic additives, solvents, etc. present in both the hybridization and wash solutions and incubations (and number thereof), as described in more detail in the references cited below (e.g., Sambrook et al., 1989; Berger and Kimmel, 1987; and Anderson and Young, 1985).

Encompassed by the invention are polynucleotide sequences that are capable of hybridizing to the claimed polynucleotide sequences, including any of the polynucleotides within the Sequence Listing, and fragments thereof under various conditions of stringency (see, for example, Wahl and Berger, 1987; and Kimmel, 1987). In addition to the nucleotide sequences listed in the Sequence Listing, full length cDNA, orthologs, and paralogs of the present nucleotide sequences may be identified and isolated using well-known methods. The cDNA libraries, orthologs, and paralogs of the present nucleotide sequences may be screened using hybridization methods to determine their utility as hybridization target or amplification probes.

With regard to hybridization, conditions that are highly stringent, and means for achieving them, are well known in the art. See, for example, Sambrook et al., 1989; Berger and Kimmel, 1987, pages 467-469; and Anderson and Young, 1985.

Stability of DNA duplexes is affected by such factors as base composition, length, and degree of base pair mismatch. Hybridization conditions may be adjusted to allow DNAs of different sequence relatedness to hybridize. The melting temperature ($T_m$) is defined as the temperature when 50% of the duplex molecules have dissociated into their constituent single strands. The melting temperature of a perfectly matched duplex, where the hybridization buffer contains formamide as a denaturing agent, may be estimated by the following equations:

(I) DNA-DNA:

$T_m(° C.)=81.5+16.6(\log [Na+])+0.41(\% G+C)-0.62(\% \text{ formamide})-500/L$ (II) DNA-RNA:

$T_m(° C.)=79.8+18.5(\log [Na+])+0.58(\% G+C)+0.12(\% G+C)^2-0.5(\% \text{ formamide})-820/L$ (III) RNA-RNA:

$T_m(° C.)=79.8+18.5(\log [Na+])+0.58(\% G+C)+0.12(\% G+C)^2-0.35(\% \text{ formamide})-820/L$ where L is the length of the duplex formed, [Na+] is the molar concentration of the sodium ion in the hybridization or washing solution, and % G+C is the percentage of (guanine+cytosine) bases in the hybrid. For imperfectly matched hybrids, approximately 1° C. is required to reduce the melting temperature for each 1% mismatch.

Hybridization experiments are generally conducted in a buffer of pH between 6.8 to 7.4, although the rate of hybridization is nearly independent of pH at ionic strengths likely to be used in the hybridization buffer (Anderson and Young, 1985). In addition, one or more of the following may be used to reduce non-specific hybridization: sonicated salmon sperm DNA or another non-complementary DNA, bovine serum albumin, sodium pyrophosphate, sodium dodecylsulfate (SDS), polyvinyl-pyrrolidone, ficoll and Denhardt's solution. Dextran sulfate and polyethylene glycol 6000 act to exclude DNA from solution, thus raising the effective probe DNA concentration and the hybridization signal within a given unit of time. In some instances, conditions of even greater stringency may be desirable or required to reduce non-specific and/or background hybridization. These conditions may be created with the use of higher temperature, lower ionic strength and higher concentration of a denaturing agent such as formamide.

Stringency conditions can be adjusted to screen for moderately similar fragments such as homologous sequences from distantly related organisms, or to highly similar fragments such as genes that duplicate functional enzymes from closely related organisms. The stringency can be adjusted either during the hybridization step or in the post-hybridization washes. Salt concentration, formamide concentration, hybridization temperature and probe lengths are variables that can be used to alter stringency (as described by the formula above). As a general guideline, high stringency is typically performed at $T_m-5°$ C. to $T_m-20°$ C., moderate stringency at $T_m-20°$ C. to $T_m-35°$ C. and low stringency at $T_m-35°$ C. to $T_m-50°$ C. for duplex >150 base pairs. Hybridization may be performed at low to moderate stringency (25-50° C. below $T_m$), followed by post-hybridization washes at increasing stringencies. Maximum rates of hybridization in solution are determined empirically to occur at $T_m-25°$ C. for DNA-DNA duplex and $T_m-15°$ C. for RNA-DNA duplex. Optionally, the degree of dissociation may be assessed after each wash step to determine the need for subsequent, higher stringency wash steps.

High stringency conditions may be used to select for nucleic acid sequences with high degrees of identity to the disclosed sequences. An example of stringent hybridization conditions obtained in a filter-based method such as a Southern or Northern blot for hybridization of complementary nucleic acids that have more than 100 complementary residues is about 5° C. to 20° C. lower than the thermal melting point ($T_m$) for the specific sequence at a defined ionic strength and pH. Conditions used for hybridization may include about 0.02 M to about 0.15 M sodium chloride, about 0.5% to about 5% casein, about 0.02% SDS or about 0.1% N-laurylsarcosine, about 0.001 M to about 0.03 M sodium citrate, at hybridization temperatures between about 50° C. and about 70° C. More preferably, high stringency conditions are about 0.02 M sodium chloride, about 0.5% casein, about 0.02% SDS, about 0.001 M sodium citrate, at a temperature of about 50° C. Nucleic acid molecules that hybridize under stringent conditions will typically hybridize to a probe based on either the entire DNA molecule or selected portions, e.g., to a unique subsequence, of the DNA.

Stringent salt concentration will ordinarily be less than about 750 mM NaCl and 75 mM trisodium citrate. Increasingly stringent conditions may be obtained with less than about 500 mM NaCl and 50 mM trisodium citrate, to even greater stringency with less than about 250 mM NaCl and 25 mM trisodium citrate. Low stringency hybridization can be obtained in the absence of organic solvent, e.g., formamide, whereas high stringency hybridization may be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. with formamide present. Varying additional parameters, such as hybridization time, the concentration of detergent, e.g., sodium dodecyl sulfate (SDS) and ionic strength, are well known to those skilled in the art. Various levels of stringency are accomplished by combining these various conditions as needed.

The washing steps that follow hybridization may also vary in stringency; the post-hybridization wash steps primarily determine hybridization specificity, with the most critical factors being temperature and the ionic strength of the final wash solution. Wash stringency can be increased by decreasing salt concentration or by increasing temperature. Stringent salt concentration for the wash steps will preferably be less than about 30 mM NaCl and 3 mM trisodium citrate, and most preferably less than about 15 mM NaCl and 1.5 mM trisodium citrate.

Thus, hybridization and wash conditions that may be used to bind and remove polynucleotides with less than the desired homology to the nucleic acid sequences or their complements that encode the present polypeptides include, for example:

0.5×SSC, 1×SSC, or 1.5×SSC, 0.2× to 2×SSC, with 0.1% SDS, at a temperature of any of 50° C., 55° C., 60° C., 65° C., or 50° C. to 65° C.;

6×SSC at 65° C.;

50% formamide, 4×SSC at 42° C.; or with, for example, two wash steps of 10-30 minutes each. Useful variations on these conditions will be readily apparent to those skilled in the art. A formula for "SSC, 20×" may be found, for example, in Ausubel et al., 1997, in Appendix A1.

A person of skill in the art would not expect substantial variation among polynucleotide species encompassed within the scope of the present invention because the highly stringent conditions set forth in the above formulae yield structurally similar polynucleotides.

If desired, one may employ wash steps of even greater stringency, including about 0.2×SSC, 0.1% SDS at 65° C. and washing twice, each wash step being about 30 minutes, or about 0.1×SSC, 0.1% SDS at 65° C. and washing twice for 30 minutes. The temperature for the wash solutions will ordinarily be at least about 25° C., and for greater stringency at least about 42° C. Hybridization stringency may be increased further by using the same conditions as in the hybridization steps, with the wash temperature raised about 3° C. to about 5° C., and stringency may be increased even further by using the same conditions except the wash temperature is raised about 6° C. to about 9° C. For identification of less closely related homologs, wash steps may be performed at a lower temperature, e.g., 50° C.

An example of a low stringency wash step employs a solution and conditions of at least 25° C. in 30 mM NaCl, 3 mM trisodium citrate, and 0.1% SDS over 30 minutes. Greater stringency may be obtained at 42° C. in 15 mM NaCl, with 1.5 mM trisodium citrate, and 0.1% SDS over 30 minutes. Even higher stringency wash conditions are obtained at 65° C.-68° C. in a solution of 15 mM NaCl, 1.5 mM trisodium citrate, and 0.1% SDS. Wash procedures will generally employ at least two final wash steps. Additional variations on these conditions will be readily apparent to those skilled in the art (see, for example, US Patent Application No. 20010010913).

Stringency conditions can be selected such that an oligonucleotide that is perfectly complementary to the coding oligonucleotide hybridizes to the coding oligonucleotide with at least about a 5-10× higher signal to noise ratio than the ratio for hybridization of the perfectly complementary oligonucleotide to a nucleic acid encoding a polypeptide known as of the filing date of the application. It may be desirable to select conditions for a particular assay such that a higher signal to noise ratio, that is, about 15× or more, is obtained. Accordingly, a subject nucleic acid will hybridize to a unique coding oligonucleotide with at least a 2× or greater signal to noise ratio as compared to hybridization of the coding oligonucleotide to a nucleic acid encoding known polypeptide. The particular signal will depend on the label used in the relevant assay, e.g., a fluorescent label, a colorimetric label, a radioactive label, or the like. Labeled hybridization or PCR probes for detecting related polynucleotide sequences may be produced by oligolabeling, nick translation, end-labeling, or PCR amplification using a labeled nucleotide.

Encompassed by the invention are polynucleotide sequences capable of hybridizing to the claimed polynucleotide sequences, including any of the polynucleotides within the Sequence Listing, and fragments thereof under various conditions of stringency (see, for example, Wahl and Berger, 1987, pages 399-407; and Kimmel, 1987). In addition to the nucleotide sequences in the Sequence Listing, full length cDNA, orthologs, and paralogs of the present nucleotide sequences may be identified and isolated using well-known methods. The cDNA libraries, orthologs, and paralogs of the present nucleotide sequences may be screened using hybridization methods to determine their utility as hybridization target or amplification probes.

EXAMPLES

It is to be understood that this invention is not limited to the particular devices, machines, materials and methods described. Although particular embodiments are described, equivalent embodiments may be used to practice the invention.

The invention, now being generally described, will be more readily understood by reference to the following examples, which are included merely for purposes of illustration of certain aspects and embodiments of the present invention and are not intended to limit the invention. It will be recognized by one of skill in the art that a polypeptide that is associated with a particular first trait may also be associated with at least one other, unrelated and inherent second trait which was not predicted by the first trait.

Example I

Project Types

Nucleic Acid Construct and Cloning Information

A number of nucleic acid constructs were used to modulate the activity of sequences of the invention. An individual project was defined as the analysis of lines for a particular construct (for example, this might include G1945 lines that constitutively overexpressed a sequence of the invention). Generally, a full-length wild-type version of a gene was directly fused to a promoter that drove its expression in transformed or transgenic plants. Such a promoter could be a constitutive promoter such as the CaMV 35S promoter, or the native promoter of that gene. Alternatively, as noted below, a promoter that drives tissue specific or conditional expression could be used in similar studies.

Expression of a given polynucleotide from a particular promoter was achieved by a direct-promoter fusion construct in which that sequence was cloned directly behind the promoter of interest. A direct fusion approach has the advantage of allowing for simple genetic analysis if a given promoter-polynucleotide line is to be crossed into different genetic backgrounds at a later date. For analysis of G1945-overexpressing plants, transgenic lines were created with the expression vector P2085 (SEQ ID NO: 27), which contained a G1945 cDNA clone. This nucleic acid construct constituted a 35S::G1945 direct promoter-fusion carrying a kanamycin resistance marker and was introduced into *Arabidopsis* plants.

As an alternative to direct promoter fusion, a two-component expression system could be used to drive transcription factor expression as noted below. For the two-component system, two separate constructs are used: 35S::LexA-GAL4TA (P6506, SEQ ID NO: 26) and opLexA::TF (where TF encodes the G1945 subclade member polypeptide, for example, SEQ ID NOs: 28 or 30). The first of these (Promoter::LexA-GAL4TA) comprises a desired promoter cloned in front of a LexA DNA binding domain fused to a GAL4 activation domain. The construct vector backbone also carries a kanamycin resistance marker, along with an opLexA::GFP reporter. Transgenic lines have been obtained containing the first component, and a "driver" line selected that shows reproducible expression of the in-cis reporter gene in the desired pattern through a number of generations. A homozygous population was established for that line, and the population can be supertransformed with the second construct (opLexA::TF) carrying the transcription factor sequence of interest cloned behind a LexA operator site. This second construct vector backbone also contains a sulfonamide resistance marker.

Each of the above methods offers a number of pros and cons. A direct fusion approach allows for much simpler genetic analysis if a given promoter-transcription factor line was to be crossed into different genetic backgrounds at a later date. The two-component method, on the other hand, potentially allows for stronger expression to be obtained via an amplification of transcription.

A list of other constructs (PIDs) included in this report, indicating the promoter fragment that was used to drive the transgene, along with the cloning vector backbone, is provided in Table 4. Compilations of the sequences of promoter fragments and the expressed transgene sequences within the PIDs are provided in the Sequence Listing.

direct fusions, respectively) to one of the polynucleotide sequences provided in SEQ ID NOs: 27-31 or 33.

Example II

Transformation Methods

Transformation of *Arabidopsis* was performed by an *Agrobacterium*-mediated protocol based on the method of Bechtold and Pelletier, 1998. Unless otherwise specified, all experimental work was done using the Columbia ecotype.

Plant preparation. *Arabidopsis* seeds were sown on mesh covered pots. The seedlings were thinned so that 6-10 evenly spaced plants remained on each pot 10 days after planting. The primary bolts were cut off a week before transformation to break apical dominance and encourage auxiliary shoots to form. Transformation was typically performed at 4-5 weeks after sowing.

Bacterial culture preparation. *Agrobacterium* stocks were inoculated from single colony plates or from glycerol stocks and grown with the appropriate antibiotics and grown until saturation. On the morning of transformation, the saturated cultures were centrifuged and bacterial pellets were re-suspended in Infiltration Media (0.5×MS, 1×B5 Vitamins, 5% sucrose, 1 mg/ml benzylaminopurine riboside, 200 μl/L Silwet L77) until an A600 reading of 0.8 was reached.

Transformation and seed harvest. The *Agrobacterium* solution was poured into dipping containers. All flower buds and rosette leaves of the plants were immersed in this solution for 30 seconds. The plants were laid on their side and wrapped to keep the humidity high. The plants were kept this way over-

TABLE 4

Sequences of promoter fragments and the expressed transgene sequences

| Gene or Construct Identifier | Construct (PID) carrying TF DNA | SEQ ID NO: of PID | Promoter used to express sequence | Project type |
|---|---|---|---|---|
| 35S CaMV promoter | — | 25 | | Promoter sequence included in direct promoter-fusion constructs |
| 35S::LexA-GAL4TA | P6506 | 26 | | Promoter sequence included in plant line for two-component supertransformation experiments |
| G1945 | P2085 | 27 | 35S | Direct promoter-fusion |
| G1945 | P28914 | 28 | 35S | With P6506, two-component supertransformation |
| G2155 | P1742 | 29 | 35S | Direct promoter-fusion |
| G2155 | P28915 | 30 | 35S | With P6506, two-component supertransformation |
| G3408 | P21246 | 31 | 35S | Direct promoter-fusion |
| G3936 | pMON93672 | | pGmSphas1 | Direct promoter-fusion |
| pGmSphas1 | | 32 | | Promoter sequence used in combination with G3936 |

The PIDs ("Plasmid IDentifiers") listed in the Sequence Listing (SEQ ID NOs: 27-31 or 33) provide the DNA sequences that each encode one of the listed transcription factors. The complete construct may be prepared by fusing a promoter (e.g., the CaMV 35S or pGmSphas1 promoters, found in SEQ ID NOs: 25, 26 or 31, for CaMV 35S direct fusions, CaMV 35S 2-component expression, or pGmSphas1 night at 4° C. and then the pots were turned upright, unwrapped, and moved to the growth racks.

The plants were maintained on the growth rack under 24-hour light until seeds were ready to be harvested. Seeds were harvested when 80% of the siliques of the transformed plants were ripe (approximately 5 weeks after the initial transformation). This transformed seed was deemed T0 seed, since it was obtained from the T0 generation, and was later plated on selection plates (either kanamycin or sulfonamide). Resistant plants that were identified on such selection plates comprised the T1 generation.

Example III

Morphology Analysis

Morphological analysis was performed to determine whether changes in polypeptide levels affect plant growth and development. This was primarily carried out on the T1 generation, when at least 10-20 independent lines were examined. However, in cases where a phenotype required confirmation or detailed characterization, plants from subsequent generations were also analyzed.

Primary transformants were selected on MS medium with 0.3% sucrose and 50 mg/l kanamycin. T2 and later generation plants were selected in the same manner, except that kanamycin was used at 35 mg/l. In cases where lines carry a sulfonamide marker (as in all lines generated by super-transformation), Transformed seeds were selected on MS medium with 0.3% sucrose and 1.5 mg/l sulfonamide. KO lines were usually germinated on plates without a selection. Seeds were cold-treated (stratified) on plates for three days in the dark (in order to increase germination efficiency) prior to transfer to growth cabinets. Initially, plates were incubated at 22° C. under a light intensity of approximately 100 microEinsteins for 7 days. At this stage, transformants were green, possessed the first two true leaves, and were easily distinguished from bleached kanamycin or sulfonamide-susceptible seedlings. Resistant seedlings were then transferred onto soil (Sunshine potting mix, Sun Gro Horticulture, Bellevue, Wash.). Following transfer to soil, trays of seedlings were covered with plastic lids for 2-3 days to maintain humidity while they became established. Plants were grown on soil under fluorescent light at an intensity of 70-95 microEinsteins and a temperature of 18-23° C. Light conditions consisted of a 24-hour photoperiod unless otherwise stated. In instances where alterations in flowering time were apparent, flowering time was re-examined under both 12-hour and 24-hour light to assess whether the phenotype was photoperiod dependent. Under our 24-hour light growth conditions, the typical generation time (seed to seed) was approximately 14 weeks.

Because many aspects of *Arabidopsis* development are dependent on localized environmental conditions, in all cases, plants were evaluated in comparison to controls in the same flat. As noted below, controls for transformed lines were wild-type plants or transformed plants harboring an empty transformation vector selected on kanamycin or sulfonamide. Careful examination was made at the following stages: seedling (1 week), rosette (2-3 weeks), flowering (4-7 weeks), and late seed set (8-12 weeks). Seed was also inspected. Seedling morphology was assessed on selection plates. At all other stages, plants were macroscopically evaluated while growing on soil. All significant differences (including alterations in growth rate, size, leaf and flower morphology, coloration, and flowering time) were recorded, but routine measurements were not taken if no differences were apparent.

Note that for a given project (gene-promoter combination), up to ten lines were typically examined in subsequent plate based physiology assays.

Flowering time: plants were grown in soil and flowering time was determined based on either or both of (i) number to days after planting to the first visible flower bud and (ii) the total number of leaves (rosette or rosette plus cauline) produced by the primary shoot meristem. Experimental lines were concluded to be late flowering or late developing if, by visual inspection, they either clearly possessed a larger number of leaves derived from the primary apical meristem relative to controls, or at a time when control plants already exhibited open flowers or seed-pods, such structures had not yet been produced by the transgenic lines.

Example IV

Physiology Experimental Methods

In subsequent Examples, unless otherwise indicated, morphological and physiological traits are disclosed in comparison to wild-type control plants. That is, a transformed plant that is described as large and/or drought tolerant was large and/or more tolerant to drought with respect to a control plant, the latter including wild-type plants, parental lines or lines transformed with an "empty" vector that does not contain a transcription factor polynucleotide sequence of interest. When a plant is said to have a better performance than controls, it generally was larger, had greater yield, and/or showed less stress symptoms than control plants. The better performing lines may, for example, have produced less anthocyanin, or were larger, greener, or remained more vigorous than controls when challenged with a particular stress, as noted below. Better performance generally implies greater size or yield, or tolerance to a particular biotic or abiotic stress, less sensitivity to ABA, or better recovery from a stress (as in the case of a soil-based drought treatment) than controls.

Plate Assays. Different plate-based physiological assays (shown below), representing a variety of abiotic and water-deprivation-stress related conditions, were used as a pre-screen to identify top performing lines (i.e. lines from transformation with a particular construct), that in some cases were tested in subsequent soil based assays. Typically, ten lines were subjected to plate assays, from which the best three lines were selected for subsequent soil based assays.

Germination assays. The following germination assays were conducted with *Arabidopsis* overexpressors of G1945 and closely-related sequences: NaCl (150 mM), mannitol (300 mM), sucrose (9.4%), ABA (0.3 µM), cold (8° C.), or polyethylene glycol (10%, with Phytogel as gelling agent), All germination assays were performed in aseptic conditions. Growing the plants under controlled temperature and humidity on sterile medium produces uniform plant material that has not been exposed to additional stresses (such as water stress) which could cause variability in the results obtained. All assays were designed to detect plants that were more tolerant or less tolerant to the particular stress condition and were developed with reference to the following publications: Jang et al., 1997, Smeekens, 1998, Liu and Zhu, 1997, Saleki et al., 1993, Wu et al., 1996, Zhu et al., 1998, Alia et al., 1998, Xin and Browse, 1998, Leon-Kloosterziel et al., 1996. Where possible, assay conditions were originally tested in a blind experiment with controls that had phenotypes related to the condition tested.

Prior to plating, seed for all experiments were surface sterilized in the following manner: (1) 5 minute incubation with mixing in 70% ethanol, (2) 20 minute incubation with mixing in 30% bleach, 0.01% triton-X 100, (3) 5× rinses with sterile water, (4) Seeds were re-suspended in 0.1% sterile agarose and stratified at 4° C. for 3-4 days.

All germination assays follow modifications of the same basic protocol. Sterile seeds were sown on the conditional media that has a basal composition of 80% MS+Vitamins. Plates were incubated at 22° C. under 24-hour light (120-130 $\mu m^{-2} s^{-1}$) in a growth chamber. Evaluation of germination and seedling vigor was performed five days after planting.

Growth assays. The following growth assays were conducted with *Arabidopsis* overexpressors of G1945 and closely-related sequences: severe desiccation (a type of water deprivation assay), growth in cold conditions at 8° C., root development (visual assessment of lateral and primary roots, root hairs and overall growth), and phosphate limitation.

Unless otherwise stated, all experiments were performed with the *Arabidopsis thaliana* ecotype Columbia (col-0) or soybean plants. Assays were usually conducted on non-selected segregating T2 populations (in order to avoid the extra stress of selection). Control plants for assays on lines containing direct promoter-fusion constructs were Col-0 plants transformed an empty transformation vector (pMEN65). Controls for 2-component lines (generated by supertransformation) were the background promoter-driver lines (i.e. promoter::LexA-GAL4TA lines), into which the supertransformations were initially performed.

Procedures

For chilling growth assays, seeds were germinated and grown for seven days on MS+Vitamins+1% sucrose at 22° C. and then transferred to chilling conditions at 8° C. and evaluated after another 10 days and 17 days.

For severe desiccation (plate-based water deficit) assays, seedlings were grown for 14 days on MS+Vitamins+1% Sucrose at 22° C. Plates were opened in a sterile laminar flow hood for 3 hr for hardening and then seedlings were removed from the media and let dry for two hours in the hood. After this time the plants were transferred back to plates and incubated at 22° C. for recovery. The plants were then evaluated after five days.

For the polyethylene glycol (PEG) hyperosmotic stress tolerance screen, plant seeds were gas sterilized with chlorine gas for 2 hrs. The seeds were plated on each plate containing 3% PEG ½×MS salts, 1% phytagel, and 10 μg/ml glufosinate-ammonium (BASTA). Two replicate plates per seed line were planted. The plates were placed at 4° C. for 3 days to stratify seeds. The plates were held vertically for 11 additional days at temperatures of 22° C. (day) and 20° C. (night). The photoperiod was 16 hours with an average light intensity of about 120 μmol/m2/s. The racks holding the plates were rotated daily within the shelves of the growth chamber carts. At 11 days, root length measurements are made. At 14 days, seedling status was determined, root length was measured, growth stage was recorded, the visual color was assessed, pooled seedling fresh weight was measured, and a whole plate photograph was taken.

Wilt screen assay. Transformed and wild-type soybean plants were grown in 5" pots in growth chambers. After the seedlings reached the VI stage (the VI stage occurs when the plants have one trifoliolate, and the unifoliolate and first trifoliolate leaves are unrolled), water was withheld and the drought treatment thus started. A drought injury phenotype score was recorded, in increasing severity of effect, as 1 to 4, with 1 designated no obvious effect and 4 indicating a dead plant. Drought scoring was initiated as soon as one plant in one growth chamber had a drought score of 1.5. Scoring continued every day until at least 90% of the wild type plants had achieved scores of 3.5 or more. At the end of the experiment the scores for both transgenic and wild type soybean seedlings were statistically analyzed using Risk Score and Survival analysis methods (Glantz, 2001; Hosmer and Lemeshow, 1999).

Data Interpretation from Plate Based Physiology Assays

At the time of evaluation, plants were given one of the following scores:

(++) Substantially enhanced performance compared to controls. The phenotype was very consistent and growth was significantly above the normal levels of variability observed for that assay.

(+) Enhanced performance compared to controls. The response was consistent but was only moderately above the normal levels of variability observed for that assay.

(wt) No detectable difference from wild-type controls.

(−) Impaired performance compared to controls. The response was consistent but was only moderately above the normal levels of variability observed for that assay.

(−−) Substantially impaired performance compared to controls. The phenotype was consistent and growth was significantly above the normal levels of variability observed for that assay.

(n/d) Experiment failed, data not obtained, or assay not performed.

Example V

Soil Drought

Clay Pot

The *Arabidopsis* soil drought assay (water deficit assays performed in clay pots) was based on that described by Haake et al., 2002.

Experimental Procedure.

Previously, we have performed clay-pot assays on segregating T2 populations, sown directly to soil. However, in the current procedure, seedlings were first germinated on selection plates containing either kanamycin or sulfonamide.

Seeds were sterilized by a 2 minute ethanol treatment followed by 20 minutes in 30% bleach/0.01% Tween and five washes in distilled water. Seeds were sown to MS agar in 0.1% agarose and stratified for three days at 4° C., before transfer to growth cabinets with a temperature of 22° C. After seven days of growth on selection plates, seedlings were transplanted to 3.5 inch diameter clay pots containing 80 g of a 50:50 mix of vermiculite:perlite topped with 80 g of Pro-Mix. Typically, each pot contained 14 seedlings, and plants of the transformed line being tested were in separate pots to the wild-type controls. Pots containing the transgenic line versus control pots were interspersed in the growth room, maintained under 24-hour light conditions (18-23° C., and 90-100 $\mu E\ m^{-2}\ s^{-1}$) and watered for a period of 14 days. Water was then withheld and pots were placed on absorbent paper for a period of 8-10 days to apply a drought treatment. After this period, a visual qualitative "drought score" from 0-6 was assigned to record the extent of visible drought stress symptoms. A score of "6" corresponded to no visible symptoms whereas a score of "0" corresponded to extreme wilting and the leaves having a "crispy" texture. At the end of the drought period, pots were re-watered and scored after 5-6 days; the number of surviving plants in each pot was counted, and the proportion of the total plants in the pot that survived was calculated.

A variation of the above method was sometimes used, whereby plants for a given transgenic line were compared to wild-type controls in the same pot. For those studies, seven wild-type seedlings were transplanted into one half of a 3.5 inch pot and seven seedlings of the line being tested were transplanted into the other half of the pot.

Analysis of results. In a given experiment, five or more pots of a transformed line were typically compared with five or more pots of the appropriate control. The mean drought score and mean proportion of plants surviving (survival rate) were calculated for both the transformed line and the wild-type pots. In each case a p-value* was calculated, which indicated the significance of the difference between the two mean values. The results for each transformed line across each planting for a particular project were then presented in a results table.

Calculation of p-values. For the assays where control and experimental plants were in separate pots, survival was analyzed with a logistic regression to account for the fact that the random variable is a proportion between 0 and 1. The reported p-value was the significance of the experimental proportion contrasted to the control, based upon regressing the logit-transformed data.

Drought score, being an ordered factor with no real numeric meaning, was analyzed with a non-parametric test between the experimental and control groups. The p-value was calculated with a Mann-Whitney rank-sum test. For the split-pot assays, matched control and experimental measurements were available for both variables. In lieu of a direct transformed regression technique for these data, the logit-transformed proportions were analyzed by parametric methods. The p-value was derived from a paired-t-test on the transformed data. For the paired score data, the p-value from a Wilcoxon test was reported.

Example VI

Experimental Results

Morphological Observations and Physiology Assay Results

All observations are made with respect to control plants, including wild-type and/or non-transformed plant lines (i.e., lines that were not overexpressing a G1945 subclade member).

Figure 3:
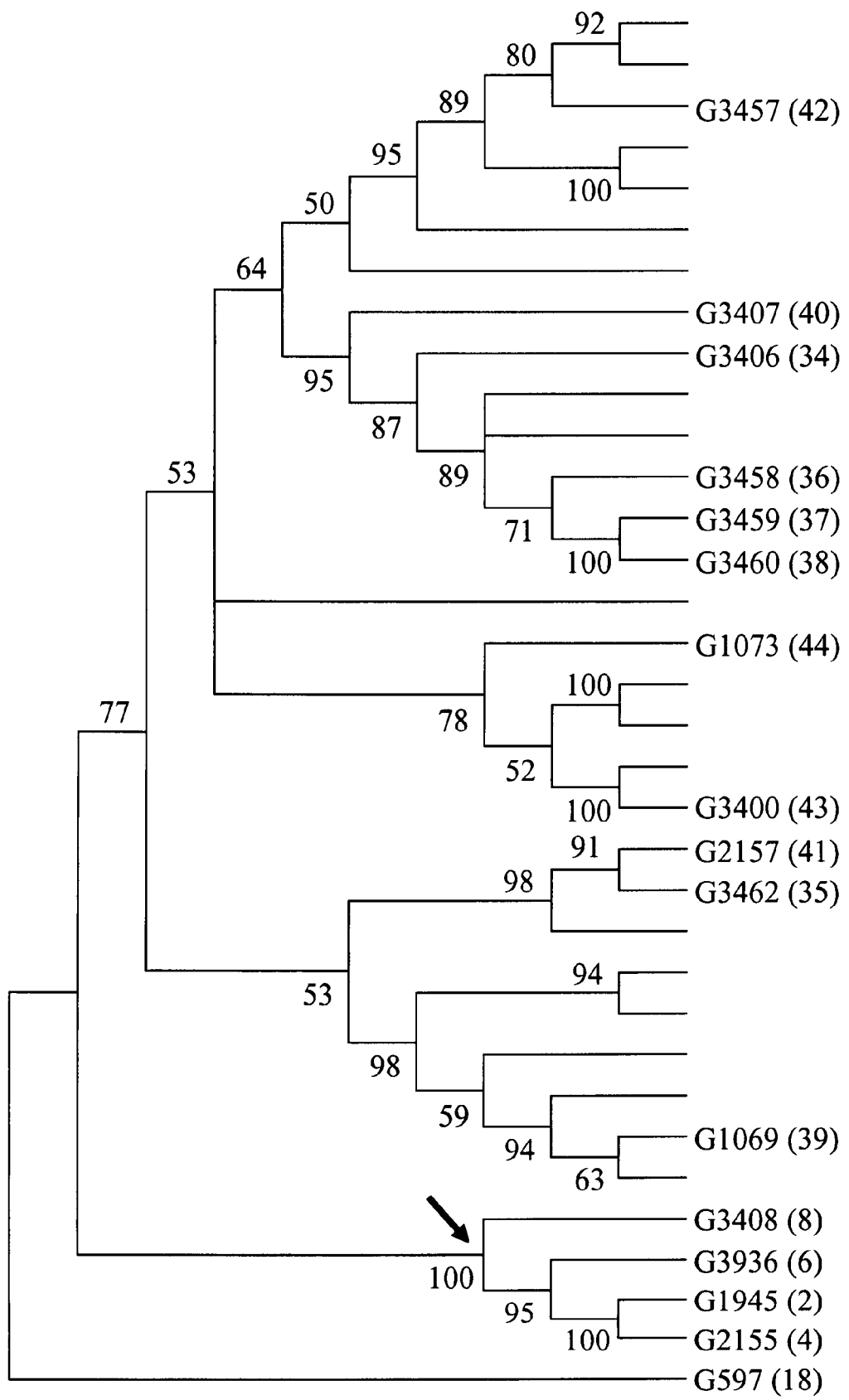
FIG. 3 shows a phylogenetic tree and multiple sequence alignments of G1945 and related full length proteins were constructed using MEGA3 (www.megasoftware.net) software. ClustalW multiple alignment parameters were as follows.

Summary: when overexpressed in plants, G1945 subclade sequences generally conferred several useful traits in *Arabidopsis* or soy plants, including late flowering and late development. In a sizeable number of species, it is advantageous to delay or prevent flowering. In crops where vegetative portions of the plant constitute the useful crop, it may be advantageous to prevent resources being diverted too early into reproductive development. In crops where the seed constitutes the useful crop, extending vegetative development late in the growing season lengthens the time available for growth and photosynthetic output and could thus bring about large increases in yields. A number of the presently disclosed transcription factors did delay and/or extend flowering time. Additional many of the presently disclosed transcription factors enhanced the growth of plant organs leading to the observed larger plants, broader leaves, and/or greater biomass than control plants. Transgenic lines comprising G1945 subclade members also had greater curling of leaves, dark coloration, greater cold tolerance, greater water deprivation tolerance, and produced greater yield in crop plants, as compared to various control plants. Data obtained with plant lines overexpressing individual G1945 subclade polypeptides are summarized in Table 5; the first four sequences listed in Table 3, G1945, G2155, G3408 and G3936 are considered to be within the G1945 subclade. Table 5 also includes data obtained for plants overexpressing G1073 (SEQ ID NO: 44) and other sequences that are closely related to the G1945 subclade but are outside of this subclade, as evidenced by the phylogenetic analysis that appears in FIG. 3. However, overexpression of the closely related sequences that fall outside of the G1945 subclade generally conferred a G1945-like appearance and often conferred similar stress tolerance, confirming that similar morphological characteristics and function can be conferred by sequences within the G1945 subclade and bracketed by the G1945 subclade. Not all assays were performed with every sequence and plant combination, but in general these results do demonstrate the ability of a significant percentage of subclade sequences to confer the improved traits listed in Table 5. Closely related sequences that fall a bit outside of the G1945 subclade also conferred some of these traits to plants, underscoring the ability of the more closely related sequences to confer the listed improved traits.

TABLE 5

Trait conferred by overexpressing G1945 subclade proteins in plants

| | | | Trait(s) conferred | | | | | |
|---|---|---|---|---|---|---|---|---|
| Polypeptide GID (SEQ ID NO:) | Percent ID to G1945 DUF296 domain | Species | Late flowering and/or development | Larger plants and/or larger organs and/or greater biomass | Greater leaf curling | Greater tolerance to water deprivation | Greater yield | Greater cold tolerance |
| G1945 (2) | 100 | At | + | + | + | + | n/d | $+^5$ |
| G2155 (4) | 87.2 | At | + | + | + | ** | n/d | ** |
| G3936* (6) | 69.6 | Gm | n/a | n/a | n/a | + | + | n/d |
| G3408 (8) | 51.9 | Os | + | + | + | + | n/d | + |
| G3406 (34) | 54.9 | Os | $+^1$ | $+^2$ | | | n/d | + |
| G3462 (35) | 54.1 | Gm | + | | + | n/d | n/d | n/d |
| G3458 (36) | 53.3 | Gm | + | | + | n/d | n/d | n/d |

TABLE 5-continued

Trait conferred by overexpressing G1945 subclade proteins in plants

| Polypeptide GID (SEQ ID NO:) | Percent ID to G1945 DUF296 domain | Species | Late flowering and/or development | Larger plants and/or larger organs and/or greater biomass | Greater leaf curling | Greater tolerance to water deprivation | Greater yield | Greater cold tolerance |
|---|---|---|---|---|---|---|---|---|
| G3459 (37) | 53.3 | Gm | + | + | + | + | n/d | + |
| G3460 (38) | 52.5 | Gm | + | + | + | + | n/d | + |
| G1069 (39) | 52.5 | At | + | + | + | + | n/d | ** |
| G3407 (40) | 51.6 | Os | + | | | | n/d | + |
| G2157 (41) | 51.2 | At | + | + | + | + | n/d | |
| G3457 (42) | 50.4 | Gm | + | +³ | + | | n/d | + |
| G3400 (43) | 50.4 | Os | + | + | + | + | n/d | + |
| G1073 (44) | 50.8 | At | + | + | + | + | +⁴ | |

+ denotes that plants from one or more overexpression lines comprising the sequence exhibited the trait
*G3936 was overexpressed in soy plants under the regulatory control or a promoter that drives expression in seeds (SEQ ID NO: 32); as such, expression of the transcription factor in this tissue was not necessarily expected to contribute to altered developmental traits. Hence, late development, increased size or biomass, and leaf curling are scored as "n/a" (not applicable). However, two G3936 soy lines did produce greater yield than control lines, and three soy lines comprising G3936 under regulatory control of SEQ ID NO: 32 were more tolerant to water deprivation in a seedling wilt assay.
**a total only three overexpression lines were tested in physiology assays, thus insufficient lines were tested to reach a firm conclusion that the experimental results were negative.
[1] two of eleven primary transformants were noted to have a slight delay in the onset of flowering versus controls.
[2] plate-germinated seedlings from one of eight lines appeared larger than control seedlings
[3] plate-germinated seedlings from one of nine lines appeared larger than control seedlings
[4] observed in soybean lines in which G1073 was regulated by a promoter that drives expression in seeds
[5] observed in maize seedlings in an early seedling growth assay In Table 5, increased tolerance to water deprivation, relative to control plants was indicated from a positive result in salt, mannitol, sucrose, desiccation, seedling wilt, or drought assays. Physiological assays indicated with a double asterisk (**) were performed with only three lines of overexpressing plants for each GID, and thus negative findings in Table 5 may reflect the fact that an insufficient number of lines were tested to date in order to observe a particular increased tolerance to water deprivation.

*Arabidopsis* plants overexpressing G3936 under the control of the promoter that drives seed expression also showed a 30% increase in total seed tocopherols, relative to controls.

Improved traits coupled with a phenotype that is morphologically similar to wild-type or other control plants may be obtained with the use of inducible or tissue-specific expression, as was the case when a promoter that drives seed-expression was used to overexpress G3936 (polynucleotide SEQ ID NO: 5, construct SEQ ID NO: 32) in soy plants. These lines were grossly similar to control plants in visual appearance but were also found to be more tolerant to water deprivation than the control plants. Other expression systems that may be envisioned include other tissue-specific promoters or stress-inducible promoters.

Considering the phylogenetic relationship and other similar traits conferred by G1945 subclade members, it is expected that subclade member sequences may confer increased total seed tocopherols and the traits listed in Table 5 when the subclade member sequences are expressed at appropriate levels and at appropriate times during plant development.

Example VII

Transformation of Eudicots to Produce Increased Yield and/or Abiotic Stress Tolerance Crop species that overexpress polypeptides of the invention may produce plants with increased water deprivation tolerance, cold and/or low nutrient tolerance and/or yield under stressed or non-stressed conditions. Thus, polynucleotide sequences listed in the Sequence Listing recombined into, for example, one of the nucleic acid constructs of the invention, or another suitable expression construct or delivery system, may be introduced into a plant for the purpose of modifying plant traits for the purpose of improving yield and/or quality. The nucleic acid construct may contain a constitutive, tissue-specific or inducible promoter operably linked to the polynucleotide. The nucleic acid construct may be introduced into a variety of plants by means well known in the art such as, for example, direct DNA transfer or *Agrobacterium tumefaciens*-mediated transformation. It is now routine to produce transgenic plants using most eudicot plants (see Weissbach and Weissbach, 1989; Gelvin et al., 1990; Herrera-Estrella et al., 1983; Bevan, 1984; and Klee, 1985). Methods for analysis of traits are routine in the art and examples are disclosed above.

Numerous protocols for the transformation of eudicots, for example, tomato, cotton and soy plants, have been previously described, and are well known in the art. Gruber et al., 1993, in Glick and Thompson, 1993, describe several expression vectors and culture methods that may be used for cell or tissue transformation and subsequent regeneration. For soybean transformation, methods are described by Miki et al., 1993; and U.S. Pat. No. 5,563,055 to Townsend and Thomas. See also U.S. Pat. No. 6,624,344 to Rangan et al., U.S. Pat. No. 6,620,990 to Rangan et al., U.S. Pat. No. 6,573,437 to Anderson et al., U.S. Pat. No. 6,479,287 to Reichert et al., and U.S. Pat. No. 6,483,013 to Reynaerts et al., which all describe cotton transformation.

There are a substantial number of alternatives to *Agrobacterium*-mediated transformation protocols, other methods for the purpose of transferring exogenous genes into soybeans or tomatoes. One such method is microprojectile-mediated transformation, in which DNA on the surface of microprojectile particles is driven into plant tissues with a biolistic device (see, for example, Sanford et al., 1987; Christou et al., 1992; Sanford, 1993; Klein et al., 1987; U.S. Pat. No. 5,015,580 (Christou et al), issued May 14, 1991; and U.S. Pat. No. 5,322,783 (Tomes et al.), issued Jun. 21, 1994).

Alternatively, sonication methods (see, for example, Zhang et al., 1991); direct uptake of DNA into protoplasts using $CaCl_2$ precipitation, polyvinyl alcohol or poly-L-ornithine (see, for example, Hain et al., 1985; Draper et al., 1982); liposome or spheroplast fusion (see, for example, Deshayes et al., 1985; Christou et al., 1987; and electroporation of protoplasts and whole cells and tissues (see, for example, Donn et al., 1990; D'Halluin et al., 1992; and Spencer et al., 1994) have been used to introduce foreign DNA and expression vectors into plants.

After a plant or plant cell is transformed (and the latter regenerated into a plant), the transformed plant may be crossed with itself or a plant from the same line, a non-transformed or wild-type plant, or another transformed plant from a different transgenic line of plants. Crossing provides the advantages of producing new and often stable transgenic varieties. Genes and the traits they confer that have been introduced into a tomato or soybean line may be moved into distinct line of plants using traditional backcrossing techniques well known in the art. Transformation of tomato plants may be conducted using the protocols of Koornneef et al., 1986, and in U.S. Pat. No. 6,613,962 to Vos et al., the latter method described in brief here. Eight day old cotyledon explants are precultured for 24 hours in Petri dishes containing a feeder layer of suspension cells plated on MS medium with 2% (w/v) sucrose and 0.8% agar supplemented with 10 μM α-naphthalene acetic acid and 4.4 μM 6-benzylaminopurine. The explants are then infected with a diluted overnight culture of *Agrobacterium tumefaciens* containing a nucleic acid construct comprising a polynucleotide of the invention for 5-10 minutes, blotted dry on sterile filter paper and cocultured for 48 hours on the original feeder layer plates. Culture conditions are as described above. Overnight cultures of *Agrobacterium tumefaciens* are diluted in liquid MS medium with 2% (w/v/) sucrose, pH 5.7) to an $OD_{600}$ of 0.8.

Following cocultivation, the cotyledon explants are transferred to Petri dishes with selective medium comprising MS medium with 4.56 μM zeatin, 67.3 μM vancomycin, 418.9 μM cefotaxime and 171.6 μM kanamycin sulfate, and cultured under the culture conditions described above. The explants are subcultured every three weeks onto fresh medium. Emerging shoots are dissected from the underlying callus and transferred to glass jars with selective medium without zeatin to form roots. The formation of roots in a kanamycin sulfate-containing medium is a positive indication of a successful transformation.

Transformation of soybean plants may be conducted using the methods found in, for example, Townsend et al., U.S. Pat. No. 5,563,055, described in brief here. In this method soybean seed is surface sterilized by exposure to chlorine gas evolved in a glass bell jar. Seeds are germinated by plating on 1/10 strength agar solidified medium without plant growth regulators and culturing at 28° C. with a 16 hour day length. After three or four days, seed may be prepared for cocultivation. The seedcoat is removed and the elongating radicle removed 3-4 mm below the cotyledons.

Overnight cultures of *Agrobacterium tumefaciens* harboring the nucleic acid construct comprising a polynucleotide of the invention are grown to log phase, pooled, and concentrated by centrifugation. Inoculations are conducted in batches such that each plate of seed was treated with a newly resuspended pellet of *Agrobacterium*. The pellets are resuspended in 20 ml inoculation medium. The inoculum is poured into a Petri dish containing prepared seed and the cotyledonary nodes are macerated with a surgical blade. After 30 minutes the explants are transferred to plates of the same medium that has been solidified. Explants are embedded with the adaxial side up and level with the surface of the medium and cultured at 22° C. for three days under white fluorescent light. These plants may then be regenerated according to methods well established in the art, such as by moving the explants after three days to a liquid counter-selection medium (see Townsend et al., U.S. Pat. No. 5,563,055).

The explants may then be picked, embedded and cultured in solidified selection medium. After one month on selective media transformed tissue becomes visible as green sectors of regenerating tissue against a background of bleached, less healthy tissue. Explants with green sectors are transferred to an elongation medium. Culture is continued on this medium with transfers to fresh plates every two weeks. When shoots are 0.5 cm in length they may be excised at the base and placed in a rooting medium.

Example VIII

Transformation of Monocots to Produce Increased Yield or Abiotic Stress Tolerance Cereal plants such as, but not limited to, corn, wheat, rice, sorghum, or barley, or grasses such as switchgrass or *Miscanthus*, may be transformed with the present polynucleotide sequences, including monocot or eudicot-derived sequences such as those presented in the present Tables, cloned into a nucleic acid construct, and expressed constitutively under, for example, the rice actin, tubulin or rab17 promoters, or with tissue-specific or inducible promoters. The expression constructs may be one found in the Sequence Listing, or any other suitable construct may be similarly used. For example, pMEN020 may be modified to replace the NptII coding region with the BAR gene of *Streptomyces hygroscopicus* that confers resistance to phosphinothricin. The KpnI and BglII sites of the Bar gene are removed by site-directed mutagenesis with silent codon changes.

The nucleic acid construct may be introduced into a variety of cereal plants by means well known in the art including direct DNA transfer or *Agrobacterium tumefaciens*-mediated transformation. The latter approach may be accomplished by a variety of means, including, for example, that of Hiei, U.S. Pat. No. 5,591,616, in which monocotyledon callus is transformed by contacting dedifferentiating tissue with the *Agrobacterium* containing the nucleic acid construct.

The sample tissues are immersed in a suspension of $3 \times 10^{-9}$ cells of *Agrobacterium* containing the nucleic acid construct for 3-10 minutes. The callus material is cultured on solid medium at 25° C. in the dark for several days. The calli grown on this medium are transferred to Regeneration medium. Transfers are continued every 2-3 weeks (2 or 3 times) until shoots develop. Shoots are then transferred to Shoot-Elongation medium every 2-3 weeks. Healthy looking shoots are transferred to rooting medium and after roots have developed, the plants are placed into moist potting soil.

The transformed plants are then analyzed for the presence of the NPTII gene/kanamycin resistance by ELISA, using the ELISA NPTII kit from 5Prime-3Prime Inc. (Boulder, Colo.).

It is also routine to use other methods to produce transgenic plants of most cereal crops (Vasil, 1994) such as corn, wheat, rice, sorghum (Cassas et al., 1993), and barley (Wan and Lemeaux, 1994). DNA transfer methods such as the microprojectile method can be used for corn (Fromm et al., 1990; Gordon-Kamm et al., 1990; Ishida, 1990, wheat, Vasil et al., 1992; Vasil et al., 1993; Weeks et al., 1993), and rice (Christou, 1991; Hiei et al., 1994; Aldemita and Hodges, 1996; and Hiei et al., 1997). For most cereal plants, embryogenic cells derived from immature scutellum tissues are the preferred cellular targets for transformation (Hiei et al., 1997; Vasil, 1994). For transforming corn embryogenic cells derived from immature scutellar tissue using microprojectile bombardment, the A188XB73 genotype is the preferred genotype (Fromm et al., 1990; Gordon-Kamm et al., 1990). After microprojectile bombardment the tissues are selected on phosphinothricin to identify the transgenic embryogenic cells (Gordon-Kamm et al., 1990). Transgenic plants are regenerated by standard corn regeneration techniques (Fromm et al., 1990; Gordon-Kamm et al., 1990).

Example IX

Expression and Analysis of Increased Yield or Abiotic Stress Tolerance in Non-Arabidopsis Species It is expected that structurally similar orthologs of the G1945 subclade of polypeptide sequences, including those found in the Sequence Listing, can confer more delayed flowering, more delayed development, more delayed senescence, darker coloration, more curled leaves, greater yield, greater size, greater biomass, or greater tolerance to a number of abiotic stresses, including water deprivation, hyperosmotic stress, or cold, relative to control plants. As sequences of the invention have been shown to increase yield, reduce stress symptoms and/or improve abiotic stress tolerance in several diverse plant species, it is also expected that these sequences will increase yield of crop or other commercially important plant species.

Northern blot analysis, RT-PCR or microarray analysis of the regenerated, transformed plants may be used to show expression of a polypeptide or the invention and related genes that are capable of inducing abiotic stress tolerance, and/or larger size.

After a eudicot plant, monocot plant or plant cell has been transformed (and the latter regenerated into a plant) with a G1945 subclade member sequence, such as SEQ ID NOs: 1, 3, 5, or 7 or a nucleotide sequence encoding SEQ ID NOs: 2, 4, 6, 8, or a nucleotide sequence encoding a polypeptide comprising a DUF296 domain of SEQ ID NOs: 13, 14, 15 or 16, or a sequence that is phylogenetically-related and closely-related to one of these sequences, may be shown to confer increased tolerance to abiotic stress, or produce greater yield relative to a control plant under the stress conditions, or produce greater yield that the control plant under non-stressed conditions. The transformed monocot plant may also be crossed with itself or a plant from the same line, a non-transformed or wild-type monocot plant, or another transformed monocot plant from a different transgenic line of plants.

The functions of specific polypeptides of the invention, including closely-related orthologs, have been analyzed and may be further characterized and incorporated into crop plants. The ectopic overexpression of these sequences may be regulated using constitutive, inducible, or tissue specific regulatory elements. Genes that have been examined and have been shown to modify plant traits (including increasing yield and/or abiotic stress tolerance) encode polypeptides found in the Sequence Listing. In addition to these sequences, it is expected that newly discovered polynucleotide and polypeptide sequences closely related to polynucleotide and polypeptide sequences found in the Sequence Listing can also confer alteration of traits in a similar manner to the sequences found in the Sequence Listing, when transformed into any of a considerable variety of plants of different species, and including eudicots and monocots. The polynucleotide and polypeptide sequences derived from monocots (e.g., the rice sequences) may be used to transform both monocot and eudicot plants, and those derived from eudicots (e.g., the *Arabidopsis* and soy genes) may be used to transform either group, although it is expected that some of these sequences will function best if the gene is transformed into a plant from the same group as that from which the sequence is derived.

As an example of a first step to determine water deprivation-related tolerance, seeds of these transgenic plants may be subjected to germination assays to measure sucrose sensing or tolerance to salt, mannitol, severe desiccation or drought, or to screen for late flowering, late development, or increased size or biomass. Sequences of the invention, that is, members of the G1945 subclade, may also be used to generate transgenic plants that are more tolerant to cold than control plants. As an example of a first step to determine increased cold tolerance, seeds of these transgenic plants may be subjected to germination assays to measure tolerance to, for example, 8° C., as described above. Plants overexpressing sequences of the invention may be found to be more tolerant to cold by having better germination, superior growth characteristics, or reduced stress, as measured by anthocyanin accumulation, as compared to control plants. Plants that are more tolerant than controls to water deprivation assays or cold are greener, more vigorous will have better survival rates than controls, or will recover better from these treatments than control plants. Examples of methods for sucrose sensing, salt tolerance, mannitol tolerance, severe desiccation or drought assays are described above.

Plants overexpressing sequences of the invention may be found to be more tolerant to high sucrose by having better germination, longer radicles, and more cotyledon expansion.

It is expected that the same methods may be applied to identify other useful and valuable sequences of the present polypeptide subclade, and the sequences may be derived from a diverse range of species.

REFERENCES CITED

Aldemita and Hodges (1996) *Planta* 199: 612-617
Alia et al. (1998) *Plant J.* 16: 155-161
Altschul (1990) *J. Mol. Biol.* 215: 403-410
Altschul (1993) *J. Mol. Evol.* 36: 290-300
Alvarez-Buylla et al. (2000) *Plant J.* 24:457-466
Anderson and Young (1985) "Quantitative Filter Hybridisation", In: Hames and Higgins, ed., *Nucleic Acid Hybridisation, A Practical Approach*. Oxford, IRL Press, 73-111
Aravind and Landsman (1998) *Nucleic Acids Res.* 26: 4413-4421
Ausubel et al. (1997) Short Protocols in Molecular Biology, John Wiley & Sons, New York, N.Y., unit 7.7

Bairoch et al. (1997) *Nucleic Acids Res.* 25: 217-221
Bates et al. (1973) *Plant Soil* 39: 205-207
Battaglia et al. (2006) Mech. Dev. 123: 267-276
Bechtold and Pelletier (1998) *Methods Mol. Biol.* 82: 259-266
Berger and Kimmel (1987), "Guide to Molecular Cloning Techniques", in Methods in Enzymology, vol. 152, Academic Press, Inc., San Diego, Calif.
Bevan (1984) *Nucleic Acids Res.* 12: 8711-8721
Bhattacharjee et al. (2001) *Proc. Natl. Acad. Sci. USA* 98: 13790-13795
Bianchi and Beltrame (2000) *EMBO Rep* 1, 109-114
Borevitz et al. (2000) *Plant Cell* 12: 2383-2393
Boss and Thomas (2002) *Nature,* 416: 847-850
Bruce et al. (2000) *Plant Cell* 12: 65-79
Cassas et al. (1993) *Proc. Natl. Acad. Sci. USA* 90: 11212-11216
Chase et al. (1993) *Ann. Missouri Bot. Gard.* 80: 528-580
Cheikh et al. (2003) U.S. Patent Application No. 20030101479
Christou et al. (1987) *Proc. Natl. Acad. Sci. USA* 84: 3962-3966
Christou (1991) *Bio/Technol.* 9:957-962
Christou et al. U.S. Pat. No. 5,015,580, issued May 14, 1991
Christou et al. (1992) *Plant. J.* 2: 275-281
Coruzzi et al. (2001) *Plant Physiol.* 125: 61-64
Coupland (1995) *Nature* 377: 482-483
Daly et al. (2001) *Plant Physiol.* 127: 1328-1333
Davies et al. (1996) (1998) *Methods Mol. Biol.* 82: 259-266
De Blaere et al. (1987) *Meth. Enzymol.* 143:277)
Deshayes et al. (1985) *EMBO J.,* 4: 2731-2737
D'Halluin et al. (1992) *Plant Cell* 4: 1495-1505
Donn et al. (1990) in *Abstracts of VIIth International Congress on Plant Cell and Tissue Culture IAPTC,* A2-38: 53
Doolittle, ed. (1996) *Methods in Enzymology,* vol. 266: "Computer Methods for Macromolecular Sequence Analysis" Academic Press, Inc., San Diego, Calif., USA
Draper et al. (1982) *Plant Cell Physiol.* 23: 451-458
Eddy (1996) *Curr. Opin. Str. Biol.* 6: 361-365
Eisen (1998) *Genome Res.* 8: 163-167
Falvo et al. (1995) *Cell* 83: 1101-1111
Feng and Doolittle (1987) *J. Mol. Evol.* 25: 351-360
Fernandez et al. (2000) *Plant Cell* 12: 183-198
Filleur et al. (2005) *Biochem. Soc. Trans.* 33: 283-286
Fowler and Thomashow (2002) *Plant Cell* 14: 1675-1690
Fromm et al. (1990) *Bio/Technol.* 8: 833-839
Fu et al. (2001) *Plant Cell* 13: 1791-1802
Gan et al. (2005) *Planta* 222: 730-742
Glick and Thompson, eds. (1993) *Methods in Plant Molecular Biology and Biotechnology.* CRC Press., Boca Raton, Fla.
Gelvin et al. (1990) *Plant Molecular Biology Manual,* Kluwer Academic Publishers
Glantz (2001) Relative risk and risk score, in Primer of Biostatistics. 5$^{th}$ ed., McGraw Hill/Appleton and Lange, publisher.
Gilmour et al. (1998) *Plant J.* 16: 433-442
Gruber et al., in Glick and Thompson (1993) *Methods in Plant Molecular Biology and Biotechnology.* eds., CRC Press, Inc., Boca Raton
Goodrich et al. (1993) Cell 75: 519-530
Gordon-Kamm et al. (1990) *Plant Cell* 2: 603-618
Haake et al. (2002) *Plant Physiol.* 130: 639-648
Hain et al. (1985) *Mol. Gen. Genet.* 199: 161-168
Haymes et al. (1985) *Nucleic Acid Hybridization: A Practical Approach,* IRL Press, Washington, D.C.
He et al. (2000) *Transgenic Res.* 9: 223-227
Hein (1990) *Methods Enzymol.* 183: 626-645
Henikoff and Henikoff (1989) *Proc. Natl. Acad. Sci. USA* 89:10915
Henikoff and Henikoff (1991) Nucleic Acids Res. 19: 6565-6572
Hepworth et al. (2002). *EMBO J.* 21: 4327-4337
Herrera-Estrella et al. (1983) *Nature* 303: 209
Hiei et al. (1994) *Plant J.* 6:271-282
Hiei, U.S. Pat. No. 5,591,616, issued 7 Jan. 1997
Hiei et al. (1997) *Plant Mol. Biol.* 35:205-218
Higgins and Sharp (1988) *Gene* 73: 237-244
Higgins et al. (1996) *Methods Enzymol.* 266: 383-402
Honma and Goto (2001) *Nature* 409: 525-529
Hosmer and Lemeshow (1999) Applied Survival Analysis: regression Modeling of Time to Event Data. John Wiley & Sons, Inc. Publisher.
Huang et al. (1996) Plant Cell 8: 81-94
Huth et al. (1997) *Nat. Struct. Biol.* 4: 657-665
Immink et al. (2002) *Proc. Natl. Acad. Sci. U.S.A.* 99: 2416-2421
Ishida (1990) *Nature Biotechnol.* 14:745-750
Jaglo et al. (2001) *Plant Physiol.* 127: 910-917
Jang et al. (1997) *Plant Cell* 9: 5-19
Kashima et al. (1985) *Nature* 313: 402-404
Kim et al. (2001) *Plant J.* 25: 247-259
Kimmel (1987) *Methods Enzymol.* 152: 507-511
Klee (1985) *Bio/Technology* 3: 637-642
Klein et al. (1987) *Nature* 327: 70-73
Klein et al. (1987); U.S. Pat. No. 4,945,050
Koornneef et al. (1986) In *Tomato Biotechnology*: Alan R. Liss, Inc., 169-178
Ku et al. (2000) *Proc. Natl. Acad. Sci. USA* 97: 9121-9126
Kyozuka and Shimamoto (2002) *Plant Cell Physiol.* 43: 130-135
Leon-Kloosterziel et al. (1996) *Plant Physiol.* 110: 233-240
Lim et al. (2000) Plant Mol. Biol. 44: 513-527
Lin et al. (1991) Nature 353: 569-571
Liu and Zhu (1997) *Proc. Natl. Acad. Sci. USA* 94: 14960-14964
Mandel (1992a) Nature 360: 273-277
Mandel et al. (1992b) *Cell* 71-133-143
Meyers (1995) Molecular Biology and Biotechnology, Wiley VCH, New York, N.Y., p 856-853
Miki et al. (1993) in *Methods in Plant Molecular Biology and Biotechnology,* p. 67-88, Glick and Thompson, eds., CRC Press, Inc., Boca Raton
Mount (2001), in *Bioinformatics: Sequence and Genome Analysis,* Cold Spring Harbor Laboratory Press, Cold Spring Harbor, N.Y., p. 543
Müller et al. (2001) *Plant J.* 28: 169-179
Nandi et al. (2000) *Curr. Biol.* 10: 215-218
Onate et al. (1994) *Mol. Cell. Biol.* 14: 3376-3391
Peng et al. (1997) *Genes Development* 11: 3194-3205)
Peng et al. (1999) *Nature* 400: 256-261
Porra et al. (1989) Biochim. Biophys. Acta: 975, 384-394
Pourtau et al., (2004) *Planta* 219: 765-772
Ratcliffe et al. (2001) *Plant Physiol.* 126: 122-132
Ratcliffe, et al. (2003) *Plant Cell* 15: 1159-1169
Reeves and Nissen (1990) *J. Biol. Chem.* 265: 8573-8582
Reeves and Nissen (1995) *Prog. Cell Cycle Res.* 1: 339-349
Reeves (2001) *Gene* 277: 63-81
Reeves and Beckerbauer (2001) *Biochim. Biophys. Acta* 1519: 13-29
Remans et al. (2006) *Proc. Natl. Acad. Sci. U.S.A.* 103: 19206-19211
Riechmann et al. (1996) *Proc. Natl. Acad. Sci. U.S.A.* 93, 4793-4798

Riechmann and Meyerowitz (1997) *Biol. Chem.* 378: 1079-1101
Riechmann et al. (2000a) *Science* 290, 2105-2110
Riechmann and Ratcliffe (2000b) *Curr. Opin. Plant Biol.* 3, 423-434
Rieger et al. (1976) *Glossary of Genetics and Cytogenetics: Classical and Molecular,* 4th ed., Springer Verlag, Berlin
Robson et al. (2001) *Plant J.* 28: 619-631
Sadowski et al. (1988) *Nature* 335: 563-564
Saleki et al. (1993) *Plant Physiol.* 101: 839-845
Sambrook et al. (1989) *Molecular Cloning: A Laboratory Manual,* 2nd Ed., Cold Spring Harbor Laboratory, Cold Spring Harbor, N.Y.
Sanford et al. (1987) *Part. Sci. Technol.* 5:27-37
Sanford (1993) *Methods Enzymol.* 217: 483-509
Shpaer (1997) *Methods Mol. Biol.* 70: 173-187
Smeekens (1998) *Curr. Opin. Plant Biol.* 1: 230-234
Smith et al. (1992) *Protein Engineering* 5: 35-51
Sonnhammer et al. (1997) *Proteins* 28: 405-420
Soltis et al. (1997) *Ann. Missouri Bot. Gard.* 84: 1-49
Spencer et al. (1994) *Plant Mol. Biol.* 24: 51-61
Stitt (1999) *Curr. Opin. Plant. Biol.* 2: 178-186
Suzuki et al. (2001) *Plant J.* 28: 409-418
Tang and Perry (2003) J. Biol. Chem. 278: 28154-28159
Thompson et al. (1994) *Nucleic Acids Res.* 22: 4673-4680
Tomes et al., U.S. Pat. No. 5,322,783, issued Jun. 21, 1994
Townsend and Thomas, U.S. Pat. No. 5,563,055, issued Oct. 8, 1996
Tudge (2000) in *The Variety of Life,* Oxford University Press, New York, N.Y. pp. 547-606
Vasil et al. (1992) *Bio/Technol.* 10:667-674
Vasil et al. (1993) *Bio/Technol.* 11:1553-1558
Vasil (1994) *Plant Mol. Biol.* 25: 925-937
Vos et al. U.S. Pat. No. 6,613,962, issued Sep. 2, 2003
Wahl and Berger (1987) *Methods Enzymol.* 152: 399-407
Wan and Lemeaux (1994) *Plant Physiol.* 104: 37-48
Weeks et al. (1993) *Plant Physiol.* 102:1077-1084
Weigel and Nilsson (1995) *Nature* 377: 482-500
Weissbach and Weissbach (1989) *Methods for Plant Molecular Biology,* Academic Press
Wu et al. (1996) *Plant Cell* 8: 617-627
Xin and Browse (1998) *Proc. Natl. Acad. Sci. USA* 95: 7799-7804
Xu et al. (2001) *Proc. Natl. Acad. Sci. USA* 98: 15089-15094
Yang et al. (2003) *Plant J.* 33: 47-59
Zhang et al. (1991) *Bio/Technology* 9: 996-997
Zhang and Forde (2000) *J. Exp. Bot.* 51: 51-59
Zhu et al. (1998) *Plant Cell* 10: 1181-1191

All publications and patent applications mentioned in this specification are herein incorporated by reference to the same extent as if each individual publication or patent application was specifically and individually indicated to be incorporated by reference.

The present invention is not limited by the specific embodiments described herein. The invention now being fully described, it will be apparent to one of ordinary skill in the art that many changes and modifications can be made thereto without departing from the spirit or scope of the appended claims. Modifications that become apparent from the foregoing description and accompanying figures fall within the scope of the claims.

What is claimed is:

1. A transgenic plant having an altered trait of greater size, greater organ size, greater biomass, darker coloration, more delayed flowering, more delayed development, more delayed senescence, or increased total seed tocopherols, as compared to a control plant, wherein the transgenic plant has been transformed with:
a nucleic acid construct comprising a recombinant nucleic acid sequence encoding a polypeptide, wherein:
the polypeptide has an AT-hook domain and the polypeptide has at least 51% amino acid identity with SEQ ID NO: 6;
wherein when the polypeptide is overexpressed in a plant, the polypeptide confers the altered trait in the plant as compared to a control plant, wherein the control plant does not contain the recombinant nucleic acid sequence.

2. The transgenic plant of claim 1, wherein the polypeptide has at least 85% amino acid identity with SEQ ID NO: 6.

3. The transgenic plant of claim 1, wherein the polypeptide has at least 95% amino acid identity with SEQ ID NO: 6.

4. The transgenic plant of claim 1, wherein the transformed plant is a eudicot.

5. The transgenic plant of claim 1, wherein the transformed plant is a legume.

6. The transformed plant of claim 1, wherein the transformed plant produces a transformed seed comprising the nucleic acid construct.

7. A method for conferring to a plant an altered trait of greater size, greater organ size, greater biomass, darker coloration, more delayed flowering, more delayed development, more delayed senescence, or increased total seed tocopherols, as compared to a control plant, the method comprising:
(a) providing a nucleic acid construct comprising a recombinant nucleic acid sequence encoding a polypeptide, wherein:
the polypeptide wherein the polypeptide has an AT-hook domain and the polypeptide has at least 95% amino acid identity with SEQ ID NO: 22;
wherein when the polypeptide is overexpressed in a plant, the polypeptide regulates transcription and confers at least one regulatory activity resulting in the altered trait in the plant as compared to a control plant; and
(b) transforming a target plant with the nucleic acid construct to produce a transformed plant having the altered trait as compared to the control plant, wherein the control plant does not contain the recombinant nucleic acid sequence.

8. The method of claim 7, wherein the methods further comprises the step of:
(c) selecting a transgenic plant that ectopically expresses the polypeptide, and/or has greater size, greater biomass, curlier leaves, darker coloration, greater tolerance to water deprivation, more delayed flowering, more delayed development, more delayed senescence, or increased seed tocopherols as compared to the control plant.

9. The method of claim 7, wherein the plant is more tolerant than the control plant to 8° C. during germination or growth, or to removal of water from the soil or growth medium in which the plant is growing, or removal of the plant at the seedling stage from its growth medium and drying for two hours.

10. The method of claim 7, wherein the method steps further comprise selfing or crossing the transformed plant with itself or another plant, respectively, to produce transformed seed.

11. A recombinant host cell derived from the transgenic plant of claim 1, wherein the recombinant host cell comprises the nucleic acid construct.

12. A transgenic seed derived from the transgenic plant of claim 1, wherein the transgenic seed comprises the recombinant nucleic acid.

13. A transgenic plant transformed with a nucleic acid construct encoding a polypeptide that has an AT-hook domain and has at least 95% amino acid identity with SEQ ID NO: 22, wherein the transgenic plant has an altered trait of greater size, greater organ size, greater biomass, darker coloration, more delayed flowering, more delayed development, more delayed senescence, or increased total seed tocopherols, as compared to a control plant, wherein the transgenic plant has been transformed with a nucleic acid construct comprising a recombinant nucleic acid sequence encoding a polypeptide; and
wherein when the polypeptide is overexpressed in a plant, the polypeptide confers the altered trait in the plant as compared to a control plant, wherein the control plant does not contain the recombinant nucleic acid sequence.

14. The transgenic plant of claim 13, wherein the polypeptide comprises SEQ ID NO: 22.

15. The transgenic plant of claim 1, wherein the polypeptide has at least 60% amino acid identity with SEQ ID NO: 6.

16. The transgenic plant of claim 1, wherein the polypeptide has at least 65% amino acid identity with SEQ ID NO: 6.

17. The transgenic plant of claim 1, wherein the transgenic plant having an altered trait of greater size, greater organ size, greater biomass, or increased total seed tocopherols as compared to a control plant.

18. The transgenic plant of claim 1, wherein the transgenic plant having an altered trait of darker coloration, more delayed flowering, more delayed development, or more delayed senescence as compared to a control plant.

19. A transgenic plant having an altered trait of greater size, greater organ size, greater biomass, greater yield, darker coloration, more delayed flowering, more delayed development, more delayed senescence, increased total seed tocopherols, as compared to a control plant, wherein the transgenic plant has been transformed with:
    a nucleic acid construct comprising a recombinant nucleic acid sequence encoding a polypeptide, wherein:
    the polypeptide has at least 90% amino acid identity with SEQ ID NO: 6;
    wherein when the polypeptide is overexpressed in a plant, the polypeptide confers the altered trait in the plant as compared to a control plant, wherein the control plant does not contain the recombinant nucleic acid sequence.

\* \* \* \* \*